US012779040B2

(12) United States Patent
Varghese et al.

(10) Patent No.: US 12,779,040 B2
(45) Date of Patent: Nov. 3, 2026

(54) SELF-REPAIRING BIOMIMETIC LUBRICANTS AND METHODS OF MAKING AND USING SAME

(71) Applicant: Duke University, Durham, NC (US)

(72) Inventors: Shyni Varghese, Durham, NC (US); Anna Gilpin, Durham, NC (US); Jiaul Hoque, Durham, NC (US)

(73) Assignee: Duke University, Durham, NC (US)

( * ) Notice: Subject to any disclaimer, the term of this patent is extended or adjusted under 35 U.S.C. 154(b) by 762 days.

(21) Appl. No.: 18/251,950

(22) PCT Filed: Nov. 5, 2021

(86) PCT No.: PCT/US2021/058319
§ 371 (c)(1),
(2) Date: May 5, 2023

(87) PCT Pub. No.: WO2022/099059
PCT Pub. Date: May 12, 2022

(65) Prior Publication Data
US 2024/0024487 A1 Jan. 25, 2024

Related U.S. Application Data

(60) Provisional application No. 63/109,900, filed on Nov. 5, 2020.

(51) Int. Cl.

| | |
|---|---|
| ***A61K 47/54*** | (2017.01) |
| ***A61K 8/73*** | (2006.01) |
| ***A61K 45/06*** | (2006.01) |
| ***A61P 19/02*** | (2006.01) |
| ***A61Q 19/08*** | (2006.01) |
| ***C08B 37/08*** | (2006.01) |

(52) U.S. Cl.
CPC ............ *A61K 47/545* (2017.08); *A61K 8/735* (2013.01); *A61K 45/06* (2013.01); *A61P 19/02* (2018.01); *A61Q 19/08* (2013.01); *C08B 37/0072* (2013.01)

(58) Field of Classification Search
None
See application file for complete search history.

(56) References Cited

U.S. PATENT DOCUMENTS

| | | | |
|---|---|---|---|
| 9,095,551 B2 * | 8/2015 | Ushida ................. A61K 31/728 | |
| 2008/0050335 A1 * | 2/2008 | Faour ...................... A61P 27/04 424/78.04 | |
| 2013/0017164 A1 | 1/2013 | Chodorowski-Kimmes et al. | |
| 2016/0051458 A1 | 2/2016 | Dublanchet et al. | |
| 2017/0233745 A1 * | 8/2017 | Dankers ............. A61K 49/0073 424/9.6 | |
| 2018/0015202 A1 | 1/2018 | Dankers et al. | |
| 2018/0094106 A1 | 4/2018 | Ma et al. | |

FOREIGN PATENT DOCUMENTS

| | | |
|---|---|---|
| CN | 110483804 A | 11/2019 |
| CN | 111892719 | 11/2020 |

OTHER PUBLICATIONS

Extended European Search Report & Opinion dated Sep. 2, 2024, European Application No. 21890184.1, 8 pages.
International Search Report and Written Opinion for PCT/US21/58319. Mailed Feb. 2, 2022. 8 pages.
Anthamatten et al., Tunability of Free vol. and Viscoelastic Damping of Thiol-Ene Networks Deep in the Glassy State. Macromolecules. 2018, 51, 2564-2571.
Brown et al., Photopolymerized dynamic hydrogels with tunable viscoelastic properties through thioester exchange. Biomaterials. Sep. 2018:178:496-503.
Dankers et al., Chemical and biological properties of supramolecular polymer systems based on oligocaprolactones. Biomaterials. Nov. 2006;27(32):5490-501.
Dankers et al., Hierarchical formation of supramolecular transient networks in water: a modular injectable delivery system. Adv Mater. May 22, 2012;24(20):2703-9.
Gerwin et al., The OARSI histopathology initiative—recommendations for histological assessments of osteoarthritis in the rat. Osteoarthritis Cartilage. Oct. 2010:18 Suppl 3:S24-34.
Glasson et al., The OARSI histopathology initiative—recommendations for histological assessments of osteoarthritis in the mouse. Osteoarthritis Cartilage. Oct. 2010:18 Suppl 3:S17-23.
Hoque et al., Stimuli-Responsive Supramolecular Hydrogels and Their Applications in Regenerative Medicine. Macromol Biosci. Jan. 2019;19(1):e1800259.
Hou et al., Rapid Self-Integrating, Injectable Hydrogel for Tissue Complex Regeneration. Adv Healthc Mater. Jul. 15, 2015;4(10):1491-5, 1423.
Ierna et al., Supplementation of diet with drill oil protects against experimental rheumatoid arthritis. BMC Muscoloskelatal Disorders. 2010, 11:136. 1-11.
Lewis et al., Acute joint pathology and synovial inflammation is associated with increased intra-articular fracture severity in the mouse knee. Osteoarthritis Cartilage. Jul. 2011;19(7):864-73.
Mantooth et al., Dynamic Hydrogels from Host-Guest Supramolecular Interactions. Macromol Biosci. Jan. 2019;19(1):e1800281.
Rodell et al., Rational design of network properties in guest-host assembled and shear-thinning hyaluronic acid hydrogels. Biomacromolecules. Nov. 11, 2013;14(11):4125-34.
Schotman et al., In Vivo Retention Quantification of Supramolecular Hydrogels Engineered for Cardiac Delivery. Adv Healthc Mater. May 2021;10(10):e2001987. 11 pages.
Sijbesma et al., Reversible polymers formed from self-complementary monomers using quadruple hydrogen bonding. Science. Nov. 28, 1997;278(5343):1601-4.

(Continued)

*Primary Examiner* — Dale R Miller
(74) *Attorney, Agent, or Firm* — Casimir Jones, S.C.; Anne M. Reynolds

(57) ABSTRACT

Disclosed herein are self-repairing biomimetic lubricant compounds, compositions comprising the same, and methods of making and using the same.

9 Claims, 33 Drawing Sheets

(56) References Cited

OTHER PUBLICATIONS

Uman et al., Recent advances in shear-thinning and self-healing hydrogels for biomedical applications. J. Appl. Polym. Sci. 2020. 48668, 1-20.
Varghese et al., Rapid Communication. Metal-Ion-Mediated Healing of Gels. Journal of Polymer Science Part A: Polymer Chemistry 2005, 44, 666-670.
Wu et al., Self-healing skupramolecular bioelastomers with shape memory property as a multifuncional platform for biomedical applications via modular assembly. Biomaterials, 2016, 104, 18-31.

* cited by examiner

SELF-REPAIRING BIOMIMETIC LUBRICANTS AND METHODS OF MAKING AND USING SAME

CROSS-REFERENCE TO RELATED APPLICATIONS

The present application claims priority to and the benefit of U.S. Provisional Patent Application No. 63/109,900, filed on Nov. 5, 2020, which is incorporated herein by reference in its entirety.

STATEMENT REGARDING FEDERALLY SPONSORED RESEARCH

This invention was made with government support under AR063184 awarded by the National Institutes of Health. The government has certain rights in the invention.

TECHNICAL FIELD

Disclosed herein are self-repairing biomimetic lubricant compounds, compositions comprising the same, and methods of making and using the same.

BACKGROUND

Biolubrication is key for the efficient function of a number of organs such as diarthrodial joints, eyes, lungs and other visceral organs. For instance, the lubricating molecules present at the articular cartilage interfaces of the diarthrodial joints promote tribological functions and facilitate smooth movements. Enabling inter-surface lubrication is also important for the seamless function of medical devices such as knee implants. Based on its unique viscoelastic properties and hydration potential, high molecular weight hyaluronic acid (HA) plays a key role in the lubrication of various organs and tissues in vivo and its alteration has been identified in diseases like osteoarthritis. Besides promoting lubrication, HA also exhibits various biological functions relevant to tissue health, such as reducing inflammation and free radical damage, as well as alleviating pain. Because of these unique functions, high molecular weight HA and its derivatives have been extensively utilized, including in clinics (e.g., viscosupplements), to mitigate diseases associated with compromised lubrication such as dry eye diseases and osteoarthritis. The primary outcome measurements of patients treated with HA-based viscosupplements vary significantly and the short residence time of HA molecules within the synovial joint is considered as one of the contributing factors to this variable efficacy. Hence, strategies that ensure long-term retention and function of HA molecules have been thought to improve the clinical outcome of viscosupplements. One of the most widely used approaches to enhance the longevity includes introducing chemical crosslinks between the HA polymer chains, however, this strategy can severely limit its function and handling. Albeit at low incidence, introduction of chemical crosslinks can also result in pseudoseptic reactions.

SUMMARY

In one aspect, the disclosure provides a functionalized hyaluronic acid compound, comprising a hyaluronic acid backbone with one or more side chains attached thereto, wherein at least one side chain comprises a ureidopyrimidinone moiety.

In some embodiments, the side chain comprising the ureidopyrimidinone moiety further comprises a linker. In some embodiments, the compound comprises repeat units of formula (I):

(I)

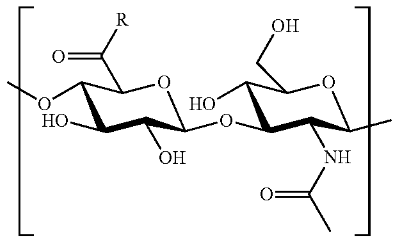

wherein each R is independently selected from —OH, —$O^-M^+$, and a moiety of formula (II):

(II)

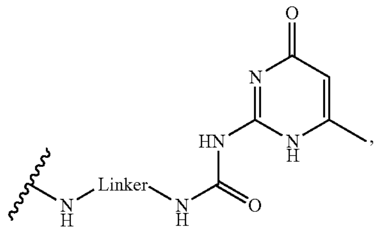

wherein each M is independently a monovalent cation, and wherein at least one R is a moiety of formula (II).

In some embodiments, the linker comprises one or more methylene (—$CH_2$—), ether (—O—), amine (—NH—), thioether (—S—), or carbonyl (—C(O)—) moieties, or any combination thereof. In some embodiments, the linker comprises a combination of urea (—NH—C(O)—NH—) and $C_1$-$C_8$ alkylene moieties. In some embodiments, the linker has formula:

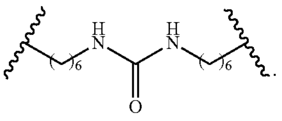

In some embodiments, about 10% to about 30% of the R groups are a moiety of formula (II). In some embodiments, about 15% to about 25% of the R groups are a moiety of formula (II). In some embodiments, the hyaluronic acid backbone has a molecular weight of about 40 kDa to about 2000 kDa. In some embodiments, the hyaluronic acid backbone has a molecular weight of about 100 kDa to about 1000 kDa.

In another aspect, the disclosure provides a pharmaceutical composition comprising a functionalized hyaluronic acid compound disclosed herein, and a pharmaceutically acceptable excipient. In some embodiments, the composition further comprises an additional therapeutic agent. In some embodiments, the additional therapeutic agent is selected from corticosteroids, growth factors, platelet-rich plasma, and stem cells, or any combination thereof.

In another aspect, the disclosure provides a method of making functionalized hyaluronic acid compound (e.g., a compound disclosed herein), comprising reacting a compound of formula (Ha) with hyaluronic acid or a salt thereof in the presence of a crosslinking reagent (IIa)

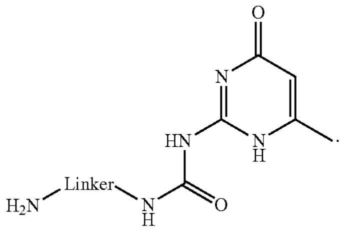

In some embodiments, the crosslinking reagent comprises a carbodiimide compound selected from 1-ethyl-3-(3-dimethylaminopropyl)carbodiimide and dicyclohexylcarbodiimide, wherein optionally the crosslinking reagent further comprises a succinimide compound selected from N-hydroxysuccinimide and N-hydroxysulfosuccinimide. In some embodiments, the method further comprises a step of providing a compound of formula (IIb):

(IIb)

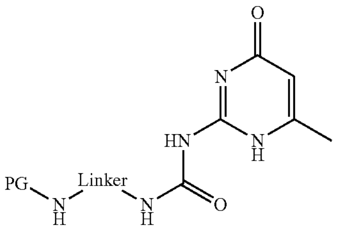

wherein PG is a protecting group; and deprotecting the compound of formula (IIb) to provide the compound of formula (IIa). In some embodiments, PG is a tert-butyloxycarbonyl protecting group.

In another aspect, the disclosure provides a method of promoting and/or improving chondroprotection in a joint of a subject, the method comprising administering to the joint a therapeutically effective amount of a functionalized hyaluronic acid compound (e.g., a compound disclosed herein), or a composition comprising the compound. In some embodiments, the joint is a knee joint.

In another aspect, the disclosure provides a method of removing and/or reducing wrinkles, restoring lost volume, smoothing lines, softening creases, and/or enhancing contours of the skin of a subject, the method comprising administering to the skin of the subject a therapeutically effective amount of a functionalized hyaluronic acid compound (e.g., a compound disclosed herein), or a composition comprising the compound.

In another aspect, the disclosure provides a method of treating an injury in a subject, the method comprising administering to the subject a therapeutically effective amount of a functionalized hyaluronic acid compound (e.g., a compound disclosed herein), or a composition comprising the compound. In some embodiments, the injury comprises an injury to a joint, tendon or ligament. In some embodiments, the injury comprises a torn or ruptured anterior cruciate ligament or medial collateral ligament.

In another aspect, the disclosure provides a method of delivering a therapeutic agent to a subject, the method comprising administering a pharmaceutical composition comprising the therapeutic agent and a functionalized hyaluronic acid compound (e.g., a compound disclosed herein) to the subject. In some embodiments, the pharmaceutical composition is administered to a joint of the subject.

In another aspect, the disclosure provides a method of providing lubrication to a joint of a subject, the method comprising administering to the joint of the subject a therapeutically effective of a functionalized hyaluronic acid compound (e.g., a compound disclosed herein), or a composition comprising the compound.

In another aspect, the disclosure provides a method of providing lubrication to an eye of a subject, the method comprising administering to the eye of the subject a therapeutically effective of a functionalized hyaluronic acid compound (e.g., a compound disclosed herein), or a composition comprising the compound.

In another aspect, the disclosure provides a method of treating dry eye disease in a subject in need thereof, the method comprising administering to the subject a therapeutically effective of a functionalized hyaluronic acid compound (e.g., a compound disclosed herein), or a composition comprising the compound.

In another aspect, the disclosure provides a method of treating osteoarthritis in a subject in need thereof, the method comprising administering to the subject a therapeutically effective of a functionalized hyaluronic acid compound (e.g., a compound disclosed herein), or a composition comprising the compound.

In another aspect, the disclosure provides a method of alleviating pain in a joint of a subject, the method comprising administering to the joint of the subject a therapeutically effective amount of a functionalized hyaluronic acid compound (e.g., a compound disclosed herein), or a composition comprising the compound.

Another aspect of the present disclosure provides all that is described and illustrated herein.

BRIEF DESCRIPTION OF THE DRAWINGS

FIG. 19A: representative IVIS images of rat knee joints following intra-articular injection of Cy7-tagged HA or HA-UPy as a function of time; dashed circles demarcate the joint region of interest (ROI) that was used for fluorescence intensity quantification, and color map reflects the epi-fluorescence intensity with red being the strongest; FIG. 19B: quantification of fluorescence intensity of ROI as a percentage of initial intensity, HA: n=2, HA-UPy: n=3, HA-UPy (mi-ACLT): n=2.

FIG. 20A: experimental timeline showing schedule of injections of saline, HA, or HA-UPy; FIG. 20B: histology of mouse joints at week 5 post-ACLT, contralateral joints without injury were used as positive control, scale bars: 200 μm; FIG. 20C: OARSI scores of mouse joints based on the Safranin-O staining results. One-way ANOVA with Tukey's multiple comparisons test was used for statistical analysis. Significance is determined as *P<0.05, ****P<0.0001.

FIG. 21A: the rat mi-ACLT procedure was performed on the left hind knee joint while the knee was flexed. ACLT was confirmed using anterior drawer test, whereby the tibia protrudes from the joint when ruptured. FIG. 21B: dissected knee joints with intact ACL and transected ACL. FIG. 21C: safranin knee joint from mi-ACLT group following 8 weeks of saline injections show severe cartilage degeneration and an osteophyte of the tibia (arrow). Contralateral joints without injury were used as positive control. Scale bar: 1 mm. The unoperated contralateral joint has a smooth cartilage surface and no osteophytes. FIG. 21D: OARSI scoring of the knee joints shows that the mi-ACLT group has a significantly higher degree of cartilage degeneration than the contralateral group. A two-tailed (unpaired) t-test was used to analyze statistical significance between groups. FIG. 21E: the cartilage of the mi-ACLT group shows more cells positive for ADAMTS-5 and MMP-13 expression, as well as clustering of chondrocytes (inset). FIGS. 21F-21I: quantitative measures of (FIG. 21F) total cartilage degeneration, (FIG. 21G) significant cartilage degeneration, (FIG. 21H) cartilage surface matrix loss, and (FIG. 21I) thickness of cartilage lesions; all of which were greater in the mi-ACLT group than the contralateral measures for both the tibia and femur. A two-way repeated measures ANOVA was used to analyze statistical significance. The significance of treatment effect is shown above the graphs.

FIG. 22A: experimental timeline showing schedule of injections. FIG. 22B: safranin O-stained mi-ACLT joint treated with HA showed severe cartilage degeneration with an osteophyte in the tibia (arrow). HA-UPy-injected joints showed strong proteoglycan staining while exhibiting some cartilage fibrillation and osteophyte formation (arrow). Contralateral joints without injury were used as a positive control. Scale bar: 1 mm. FIG. 22C: OARSI scoring indicates that the HA-UPy group had significantly less degeneration than the unmodified HA group. Data are presented as means (±s.e.m.) and statistical significance was analyzed using one-way ANOVA with Tukey's multiple comparisons test. FIG. 22D: ADAMTS-5 and MMP-13 IHC staining of tibial cartilage. Greater positive staining and chondrocyte clustering (inset) is observed in the HA group compared to the HA-UPy group. Scale bar: 100 μm. FIGS. 22E-22H: quantitative measures of (FIG. 22E) total cartilage degeneration, (FIG. 22F) significant cartilage degeneration, (FIG. 22G) cartilage surface matrix loss, and (FIG. 22H) thickness of cartilage lesions for both the tibia and femur. A two-way repeated measures ANOVA was used to analyze statistical significance with Tukey's multiple comparisons used to analyze the differences between treatments. The significance in the legend shows the Tukey's multiple comparisons between treatments. Significance is determined as *P<0.05, P<0.01, and *P<0.001.

Figure 1:
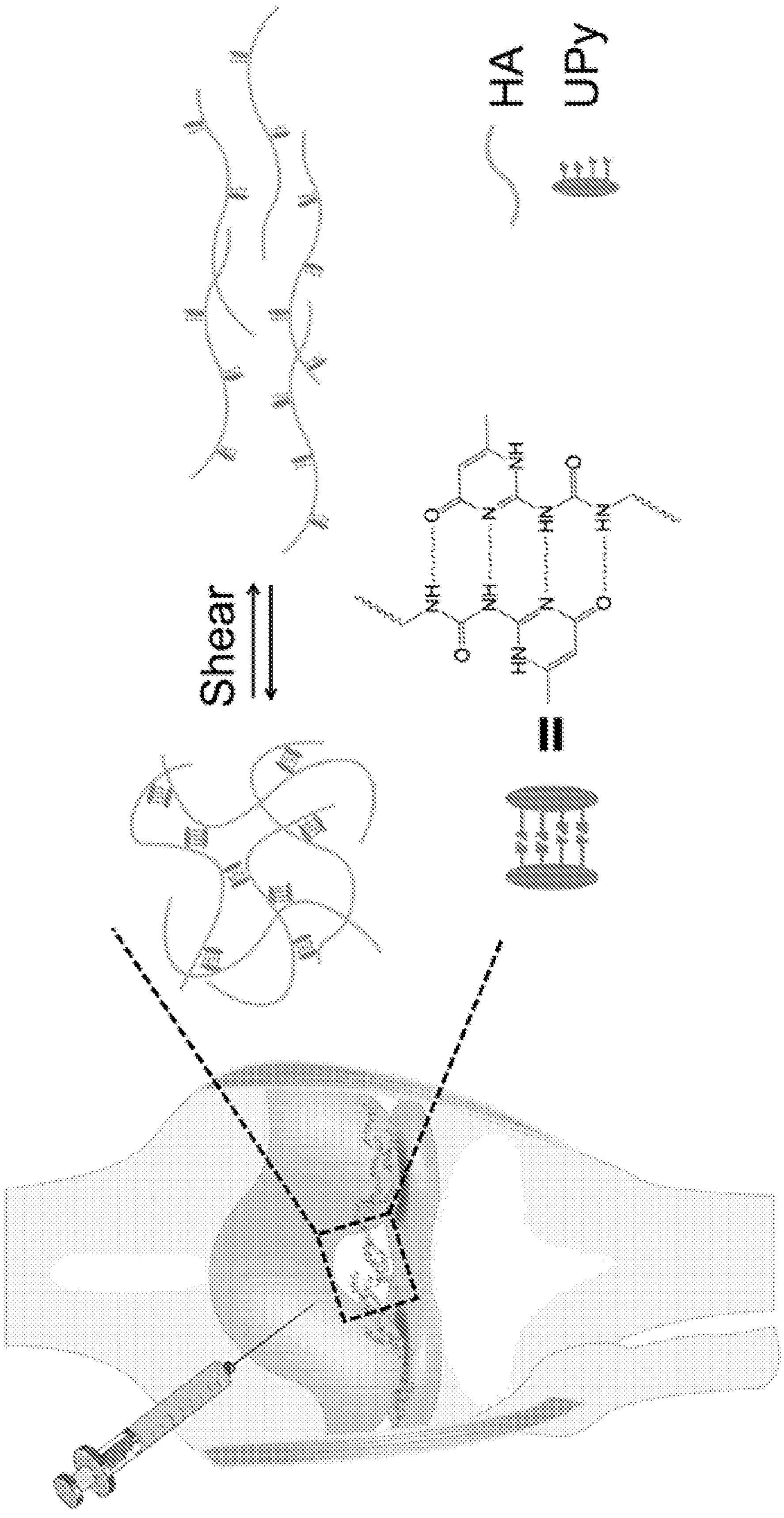
FIG. 1 is a schematic of intra-articular injection of a self-healing HA lubricant disclosed herein.

Data in the drawings are presented as means (±s.e.m.).

DETAILED DESCRIPTION

Disclosed herein are functionalized hyaluronic acid (HA) molecules, with improved physical and biological functions compared to unfunctionalized HA, without compromising its injectability. Although other chemistries and interactions have been used to create polymer networks with dynamic crosslinking to vary the viscoelastic properties and impart functions like self-healing, disclosed herein are HA molecules functionalized with ureidopyrimidinone (UPy) to enable self-healing of HA polymer chains under physiological conditions, via reversible secondary interactions (see, e.g., Sijbesma et al., *Science* 1997, 278, 1601). UPy molecules rapidly dimerize through quadruple hydrogen bonding resulting in dynamic supramolecular structures under physiological conditions. HA molecules endowed with UPy moieties can form a dynamic network through hydrogen bonding while exhibiting shear-thinning behavior (via reorganization of the polymer chains in response to shear forces), thus enabling easy injection and efficient lubrication. At rest, the rapid UPy dimerization re-establishes the stable supramolecular network, and these "self-generating" networks can resist rapid clearance from the synovial space (FIG. 1). Thus, the self-healing HA molecules may offer the benefits of both high molecular weight HA (shear thinning, mechanical adaptability, and enhanced lubrication), as well as chemically crosslinked HA (improved in vivo retention and reduced enzymatic degradation).

A. Definitions

Unless otherwise defined, all technical terms used herein have the same meaning as commonly understood by one of ordinary skill in the art to which this disclosure belongs.

Definitions of specific terms, including certain functional groups and chemical terms, are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Sorrell, Organic Chemistry, 2nd edition, University Science Books, Sausalito, 2006; Smith, March's Advanced Organic Chemistry: Reactions, Mechanism, and Structure, 7th Edition, John Wiley & Sons, Inc., New York, 2013; Larock, Comprehensive Organic Transformations, 3rd Edition, John Wiley & Sons, Inc., New York, 2018; and Carruthers, Some Modern Methods of Organic Synthesis, 3rd Edition, Cambridge University Press, Cambridge, 1987; the entire contents of each of which are incorporated herein by reference.

As used herein, the term "alkylene" refers to a divalent group derived from a straight or branched chain hydrocarbon of 1 to 12 carbon atoms ($C_1$-$C_{12}$ alkylene), for example, of 1 to 6 carbon atoms ($C_1$-$C_6$ alkylene). Representative examples of alkylene include, but are not limited to, $—CH_2—$, $—CH_2CH_2—$, $—CH(CH_3)—$, $—CH_2CH_2CH_2—$, $—CH_2CH(CH_3)—$, $—CH_2CH_2CH_2CH_2—$, $—CH_2CH(CH_3)CH_2—$, $—CH_2CH_2CH(CH_3)—$, $—CH_2CH_2CH_2CH_2CH_2—$, $—CH_2CH(CH_3)CH_2CH_2—$, $—CH(CH_3)CH_2CH_2CH_2—$, $—CH_2CH_2CH_2CH_2CH_2CH_2—$, $—CH_2CH_2CH(CH_3)CH_2CH_2—$, $—CH_2CH(CH_3)CH_2CH_2CH_2—$, and $—CH(CH_3)CH_2CH_2CH_2CH_2—$.

As used herein, the term "ureidopyrimidinone" or "ureidopyrimidinone moiety" refers to a group of formula:

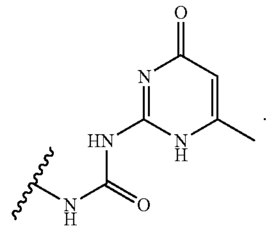 [SMILES: *NC(=O)Nc1nc(=O)cc(C)[nH]1]

As used herein, in chemical structures the indication:

represents a point of attachment of one moiety to another moiety (e.g., a ureidopyrimidinone moiety or a linker to a hyaluronic acid backbone).

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or physiological condition and/or the remission of the disease, disorder or physiological condition. As used herein, the terms "prevent," "preventing," "prevention," "prophylactic treatment" and the like refer to reducing the probability of developing a disease, disorder or physiological condition in a subject, who does not have, but is at risk of or susceptible to developing a disease, disorder or physiological condition. The term "effective amount" or "therapeutically effective amount" refers to an amount sufficient to effect beneficial or desirable biological and/or clinical results.

As used herein, the term "administering" an agent, such as a therapeutic entity to an animal or cell, is intended to refer to dispensing, delivering or applying the substance to the intended target. In terms of the therapeutic agent, the term "administering" is intended to refer to contacting or dispensing, delivering or applying the therapeutic agent to a subject by any suitable route for delivery of the therapeutic agent (e.g., lubricant) to the desired location in the animal, including delivery by either the parenteral or oral route, intramuscular injection, subcutaneous/intradermal injection, intravenous or intraarticular injection, intrathecal administration, buccal administration, transdermal delivery, topical administration, and administration by the intranasal or respiratory tract route.

As used herein, the term "subject" and "patient" are used interchangeably and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. The compounds, compositions, and methods disclosed herein can be used on a sample either in vitro (for example, on isolated cells or tissues) or in vivo in a subject (i.e. living organism, such as a patient).

Articles “a” and “an” are used herein to refer to one or to more than one (i.e. at least one) of the grammatical object of the article. By way of example, “an element” means at least one element and can include more than one element.

“About” is used to provide flexibility to a numerical range endpoint by providing that a given value may be “slightly above” or “slightly below” the endpoint without affecting the desired result.

The use herein of the terms “including,” “comprising,” or “having,” and variations thereof, is meant to encompass the elements listed thereafter and equivalents thereof as well as additional elements. As used herein, “and/or” refers to and encompasses any and all possible combinations of one or more of the associated listed items, as well as the lack of combinations where interpreted in the alternative (“or”).

As used herein, the transitional phrase “consisting essentially of” (and grammatical variants) is to be interpreted as encompassing the recited materials or steps “and those that do not materially affect the basic and novel characteristic(s)” of the claimed invention. Thus, the term “consisting essentially of” as used herein should not be interpreted as equivalent to “comprising.”

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

B. Compounds

The present disclosure is based, in part, on the discovery by the inventor of an injectable, self-healing/self-repairing hyaluronic acid based lubricant that exhibits multiple functionalities.

Accordingly, one aspect of the present disclosure provides a functionalized hyaluronic acid compound, comprising a hyaluronic acid backbone with one or more side chains attached thereto, wherein at least one side chain comprises a ureidopyrimidinone moiety.

Hyaluronic acid (HA) is an anionic, non-sulfated glycosaminoglycan that is naturally found throughout connective, epithelial, and neural tissues. It is one of the chief components of the extracellular matrix. It is a polymer of disaccharide subunits, wherein the disaccharide is composed of D-glucuronic acid and N-acetyl-D-glucosamine units, linked by alternating β-(1→4) and β-(1→3) glycosidic bonds. The structure of the repeating unit is shown below in brackets:

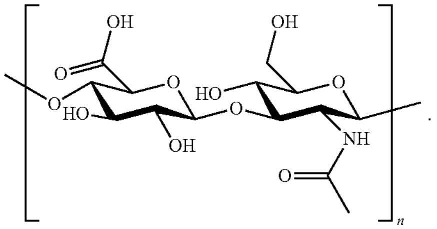

Illustrated above is the neutral form of hyaluronic acid. The acidic —COOH groups on the glucuronic acid moieties are often ionized, and hyaluronic acid is accordingly often in a hyaluronate salt form, the most common of which is sodium hyaluronate. Another well-known salt form is potassium hyaluronate. When “hyaluronic acid” is mentioned herein, it should be expressly understood that this term includes salt forms thereof, such as sodium hyaluronate and potassium hyaluronate.

The functionalized hyaluronic acid compounds disclosed herein include side chains that comprise a ureidopyrimidinone (UPy) moiety. As discussed above, UPy molecules rapidly dimerize through quadruple hydrogen bonding, which can result in formation of dynamic supramolecular structures under physiological conditions, and can exhibit shear-thinning behavior (via reorganization of the polymer chains in response to shear forces). This allows for easy injection of UPy-modified HA compounds, and efficient lubrication.

The UPy moieties can be attached to the HA backbone either directly or via one or more linking atoms. In other words, the side chains attached to the HA backbone can include the UPy moiety and a linker. HA has a plurality of carboxylic acid moieties, with one on each of the glucuronic acid subunits of the disaccharide repeating unit. This provides a convenient handle for attachment of the UPy moieties, e.g., via amide bond formation, as further discussed below.

In some embodiments, the functionalized hyaluronic acid compound comprises repeat units of formula (I):

(I)

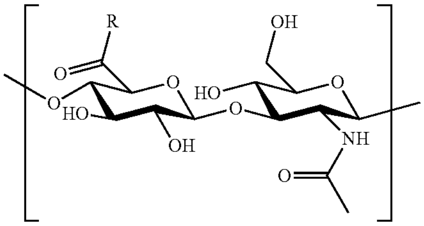

wherein each R is independently selected from —OH, —$O^-M^+$, and a moiety of formula (II):

(II)

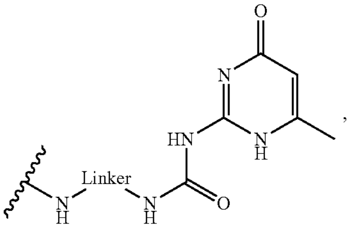

wherein each M is independently a monovalent cation, and wherein at least one R is a moiety of formula (II). In some embodiments, the functionalized hyaluronic acid compound consists essentially of repeat units of formula (I). In some embodiments, the functionalized hyaluronic acid compound consists of repeat units of formula (I) and suitable end groups (e.g., hydroxy groups). In some embodiments, $M^+$ is sodium. In some embodiments, $M^+$ is potassium.

The Linker moiety in the functionalized hyaluronic acid compounds, including the linker group in the moiety of formula (II), can be any suitable linking group that connects the UPy moiety to the HA backbone. In some embodiments, the linker comprises one or more methylene (—$CH_2$—), ether (—O—), amine (—NH—), thioether (—S—), or carbonyl (—C(O)—) moieties, or any combination thereof. For example, a carbonyl group and an ether group can together provide an ester moiety (—C(O)O—), a carbonyl group and two ether groups can together provide a carbonate moiety (—OC(O)O—), a carbonyl group and an amine group can together provide an amide moiety (—C(O)NH—), a carbonyl group and two amine groups can together provide a urea moiety (—NHC(O)NH—), a carbonyl group together with an amine group and an ester group can provide a carbamate moiety (—OC(O)NH—), multiple methylene groups can together form an alkylene chain, etc. In some embodiments, the linker comprises a combination of $C_1$-$C_8$ alkylene moieties and one or more ether, amine, carbonyl, ester, amide, carbonate, urea, or carbamate moieties. In some embodiments, the linker has formula:

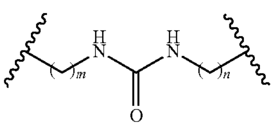

wherein m and n are each independently selected from 1, 2, 3, 4, 5, 6, 7, and 8. In some embodiments, the linker has formula:

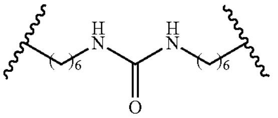

The degree of functionalization of the HA can be varied by adjusting the synthesis parameters (discussed further below), such as the amount of the UPy-containing compound (e.g., compound of formula (IIa)), the reaction time, and the like. In some embodiments, in the functionalized hyaluronic acid compound, about 10% to about 30%, or about 15% to about 25%, or about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% of the —COOH groups of the HA can be functionalized with a UPy-containing side chain. For example, in some embodiments, when the functionalized hyaluronic acid compound comprises repeat units of formula (I), about 10% to about 30%, or about 15% to about 25%, or about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% of the R groups in the compound are a moiety of formula (II). The degree of functionalization can be determined, e.g., using nuclear magnetic resonance (NMR) spectroscopy (e.g., by comparing the integrated peak area of the pyrimidinone protons in the UPy unit to that of the acetyl protons in the N-acetylglucosamine unit of the HA).

The starting hyaluronic acid compound can have a variety of molecular weights. For example, the starting hyaluronic acid compound can have an average molecular weight of about 40 kDa to about 2000 kDa, or about 100 kDa to about 1000 kDa, e.g., about 40 kDa, about 50 kDa, about 60 kDa, about 70 kDa, about 80 kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa, about 210 kDa, about 220 kDa, about 230 kDa, about 240 kDa, about 250 kDa, about 260 kDa, about 270 kDa, about 280 kDa, about 290 kDa, about 300 kDa, about 350 kDa, about 400 kDa, about 450 kDa, about 500 kDa, about 550 kDa, about 600 kDa, about 650 kDa, about 700 kDa, about 750 kDa, about 800 kDa, about 850 kDa, about 900 kDa, about 950 kDa, about 1000 kDa, about 1100 kDa, about 1200 kDa, about 1300 kDa, about 1400 kDa, about 1500 kDa, about 1600 kDa, about 1700 kDa, about 1800 kDa, about 1900 kDa, or about 2000 kDa. In some embodiments, the hyaluronic acid compound has an average molecular weight of about 200 kDa. In some embodiments, the hyaluronic acid compound has an average molecular weight of about 1000 kDa.

The present disclosure also includes isotopically-labeled compounds, which are identical to those described above but for the fact that one or more atoms are replaced by an atom having an atomic mass or mass number different from the atomic mass or mass number usually found in nature. Examples of isotopes suitable for inclusion in the compounds of the disclosure are hydrogen, carbon, nitrogen, oxygen, and chlorine, such as, but not limited to $^2H$, $^3H$, $^{13}C$, $^{14}C$, $^{15}N$, $^{18}O$, and $^{36}Cl$.

The functionalized hyaluronic acid compounds can be prepared by a variety of methods. As discussed above, the carboxylic acid groups of the HA provide a convenient reactive handle for attachment of the side chains comprising the UPy moieties. Accordingly, the functionalized hyaluronic acid compounds can be prepared by a method comprising reacting a compound of formula (IIa) with hyaluronic acid or a salt thereof in the presence of a crosslinking reagent (IIa)

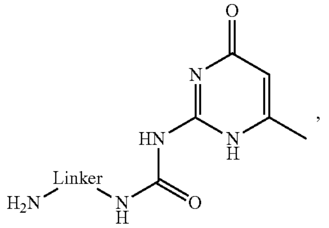

where the Linker in the compound of formula (IIa) can be any linker described herein.

Crosslinking reagents are well-known in the art, particularly in the realm of amide bond formation in peptide synthesis. For example, carbodiimide compounds are commonly used for labeling or crosslinking to carboxylic acids. Among the most readily available and commonly used carbodiimides are 1-ethyl-3-(3-dimethylaminopropyl) carbodiimide (EDC) and dicyclohexylcarbodiimide (DCC), the former of which is water-soluble and the latter of which is water-insoluble. Given the water-soluble nature of HA, EDC may be particularly useful in the context of the disclosed methods. Carbodiimides are commonly used in conjunction with succinimidyl-ester forming compounds, such as N-hydroxysuccinimide or N-hydroxysulfosuccinimide, to improve coupling efficiency. Accordingly, in some embodiments, the crosslinking reagent comprises a carbodiimide compound selected from 1-ethyl-3-(3-dimethylaminopropyl)carbodiimide and dicyclohexylcarbodiimide (or a salt of either thereof), wherein optionally the crosslinking reagent further comprises a succinimide compound selected from N-hydroxysuccinimide and N-hydroxysulfosuccinimide. Other coupling agents can also be used; examples include benzotriazol-1-yloxytris(dimethylamino)phosphonium hexafluorophosphate (BOP), 7-(azabenzotriazol-1-yl)oxy tris(dimethylamino)phosphonium hexafluorophosphate (AOP), benzotriazol-1-yloxytripyrrolidinophosphonium hexafluorophosphate (PyBOP), (7-azabenzotriazol-1-yloxy) tripyrrolidinophosphonium hexafluorophosphate (PyAOP), 2-(1H-benzotriazol-1-yl)-1,1,3,3-tetramethyluronium hexafluorophosphate (HBTU), 1-[bis(dimethylamino)methylene]-1H-1,2,3-triazolo[4,5-b]pyridinium 3-oxide hexafluorophosphate (HATU), and the like.

The compound of formula (IIa) can be prepared by first synthesizing a compound of formula (IIb):

(IIb)

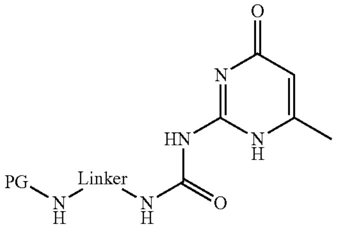

wherein PG is a protecting group. The protecting group can then be deprotected to provide the compound of formula (IIa). Suitable protecting groups, and the methods for protecting and deprotecting different substituents using such suitable protecting groups, are well known to those skilled in the art; examples of which can be found in the treatise by P G M Wuts entitled "Greene's Protective Groups in Organic Synthesis" (5th ed.), John Wiley & Sons, Inc. (2014), which is incorporated herein by reference in its entirety. For example, in some embodiments, the protecting group is a tert-butyloxycarbonyl (Boc) group. Other common protecting groups for amines include carbobenzyloxy (Cbz) groups, 9-fluorenylmethyloxycarbonyl (Fmoc) groups, benzyl (Bn) groups (including p-methoxybenzyl and 2,4-dimethoxybenzyl groups), carbamate groups, and the like.

Reaction conditions and reaction times for each individual step can vary depending on the particular reactants employed and substituents present in the reactants used. Reactions can be worked up in a conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Standard experimentation, including appropriate manipulation of the reaction conditions, reagents and sequence of the synthetic route, protection of any chemical functionality that cannot be compatible with the reaction conditions, and deprotection at a suitable point in the reaction sequence of the method, are included in the scope of the disclosure.

C. Pharmaceutical Compositions and Modes of Administration

In another aspect, the present disclosure further provides compositions comprising a compound as described herein and a pharmaceutically acceptable carrier. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols such as propylene glycol; esters such as, but not limited to, ethyl oleate and ethyl laurate; agar; buffering agents such as, but not limited to, phosphate buffers (e.g., monobasic sodium phosphate and/or dibasic sodium phosphate), magnesium hydroxide and aluminum hydroxide; alginic acid; pyrogen-free water; isotonic saline; Ringer's solution; ethyl alcohol, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator. The exact nature of the carrier will depend upon the desired use for the composition, and may range from being suitable or acceptable for veterinary uses to being suitable or acceptable for human use. Techniques and formulations may generally be found in "Remington's Pharmaceutical Sciences," (Meade Publishing Co., Easton, Pa.).

For topical administration, the compounds and/or pharmaceutical compositions thereof as provided herein may be formulated as solutions, gels, ointments, creams, suspensions, etc. as are well-known in the art. Systemic formulations include those designed for administration by injection, e.g., subcutaneous, intravenous, intramuscular, intraarterial, intrathecal or intraperitoneal injection, as well as those designed for subdermal (e.g., below the skin), transdermal, transmucosal, oral or pulmonary administration.

In some embodiments, useful injectable preparations include sterile suspensions, solutions or emulsions of the active compound(s) in aqueous or oily vehicles. The compounds and/or pharmaceutical compositions thereof as provided herein may also contain formulating agents, such as a suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer (e.g., phosphate-buffered saline), dextrose solution, etc., before use.

For transmucosal administration, penetrants appropriate to the barrier to be permeated are used in the formulation. Such penetrants are known in the art.

For ocular administration, the compounds and/or pharmaceutical compositions thereof as provided herein may be formulated as a solution, emulsion, suspension, etc. suitable for administration to the eye. A variety of vehicles suitable for administering compounds to the eye are known in the art.

For prolonged delivery, the compounds and/or pharmaceutical compositions thereof as provided herein can be formulated as a depot preparation for administration by implantation or intramuscular injection. The lubricants and/or pharmaceutical compositions thereof as provided herein may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compounds and/or pharmaceutical compositions thereof as provided herein for percutaneous absorption may be used. To this end, permeation enhancers may be used to facilitate transdermal penetration of the lubricants and/or pharmaceutical compositions thereof as provided herein.

Alternatively, other pharmaceutical delivery systems may be employed. Liposomes and emulsions are well-known examples of delivery vehicles that may be used to deliver lubricants and/or pharmaceutical compositions thereof as provided herein. Certain organic solvents such as dimethyl sulfoxide (DMSO) may also be employed, although usually at the cost of greater toxicity.

Pharmaceutical compositions comprising the compound(s) may be manufactured by means of conventional mixing, dissolving, granulating, dragee-making, levigating, emulsifying, encapsulating, entrapping or lyophilization processes as well as according to the methods provided herein. The compositions may be formulated in conventional manner using one or more physiologically acceptable carriers, which facilitate processing of the compounds into preparations which can be used pharmaceutically.

When used to treat or prevent a disease, disorder, or physiological condition, the compositions described herein may be administered singly, or as mixtures of one or more compounds with other agents (e.g., therapeutic agents) useful for treating such diseases, disorders and/or physiological conditions as well as the symptoms associated therewith. Such agents may include, but are not limited to, platelet-rich plasma, corticosteroids (e.g., betamethasone, methylprednisolone, or triamcinolone), growth factors (e.g., platelet-derived growth factor (PDGF), epidermal growth factor (EGF), vascular endothelial growth factor (VEGF), transforming growth factor β (TGFβ), connective tissue growth factor (CTGF), or basic fibroblast growth factor (bFGF)), stem cells (e.g., adipose-derived or bone marrow-derived stem cells), and other therapeutic agents such as small molecule drugs, biologic drugs, and drug candidates. The compounds disclosed herein have lubricant properties, as discussed above, and may be administered in the form of lubricants per se, or as pharmaceutical compositions comprising a lubricant.

The compounds and/or pharmaceutical compositions thereof as provided herein may, if desired, be presented in a pack or dispenser device which may contain one or more unit dosage forms containing the compounds and/or pharmaceutical compositions thereof as provided herein. The pack may, for example, comprise metal or plastic foil, such as a blister pack. The compounds and/or pharmaceutical compositions may also be provided in a dispenser device such as a syringe, e.g., a syringe pre-loaded with suitable dose of the compound or composition. The pack or dispenser device may be accompanied by instructions for administration.

The compounds and/or pharmaceutical compositions thereof as provided herein described herein, will generally be used in an amount effective to achieve the intended result, for example in an amount effective to treat or prevent the particular disease, disorder or physiological condition being treated. By therapeutic benefit is meant eradication or amelioration of the underlying disease, disorder or physiological condition being treated and/or eradication or amelioration of one or more of the symptoms associated with the underlying disease, disorder or physiological condition such that the patient reports an improvement in feeling or condition, notwithstanding that the patient may still be afflicted with the underlying disease, disorder or physiological disorder. Therapeutic benefit also generally includes halting or slowing the progression of the disease, disorder or physiological condition regardless of whether improvement is realized.

The amount of compounds and/or pharmaceutical compositions thereof as provided herein administered will depend upon a variety of factors, including, for example, the particular indication being treated, the mode of administration, whether the desired benefit is prophylactic or therapeutic, the severity of the indication being treated and the age and weight of the patient, the bioavailability of the particular compounds and/or pharmaceutical compositions thereof as provided herein, the conversation rate and efficiency into active drug compounds and/or pharmaceutical compositions thereof as provided herein under the selected route of administration, etc.

Determination of an effective dosage of compounds and/or pharmaceutical compositions thereof as provided herein for a particular use and mode of administration is well within the capabilities of those skilled in the art. Effective dosages may be estimated initially from in vitro activity and metabolism assays. For example, an initial dosage of compounds and/or pharmaceutical compositions thereof as provided herein for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compounds and/or pharmaceutical compositions thereof as provided herein via the desired route of administration is well within the capabilities of skilled artisans. Initial dosages of compounds and/or pharmaceutical compositions thereof as provided herein can also be estimated from in vivo data, such as animal models. Animal models useful for testing the efficacy of the active metabolites to treat or prevent the various diseases, disorders or physiological conditions described above are well-known in the art. Animal models suitable for testing the bioavailability and/or metabolism of compounds and/or pharmaceutical compositions thereof as provided herein into active metabolites are also well-known. Ordinarily skilled artisans can routinely adapt such information to determine dosages of particular compounds suitable for human administration.

Dosage amounts will typically be in the range of from about 1 µL, 2 µL, 3 µL, 4 µL, 5 µL, 6 µL, 7 µL, 8 µL, 9 µL, 10 µL, 15 µL, 20 µL, 25 µL, 30 µL, 35 µL, 40 µL, 45 µL, 50 µL, 55 µL, 60 µL, 65 µL, 70 µL, 75 µL, 80 µL, 85 µL, 90 µL, 95 µL, 100 µL, of a compound or pharmaceutical composition thereof, having a concentration of 1%, 2%, 3%, 4%, 5%, 6%, 7%, 8%, 9%, 10%, 15%, 20%, 25%, 30% of compound in a solution such as saline, but may be higher or lower, depending upon, among other factors, the activity of the active compound, the bioavailability of the compound, its metabolism kinetics and other pharmacokinetic properties, the mode of administration and various other factors, discussed above. Dosage amount and interval may be adjusted individually to provide physiological levels of the compounds and/or pharmaceutical compositions thereof as provided herein which are sufficient to maintain therapeutic or prophylactic effect. For example, the compounds and/or pharmaceutical compositions thereof as provided herein may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compounds and/or pharmaceutical compositions thereof as provided herein may not be related to plasma concentration. Skilled artisans will be able to optimize effective dosages without undue experimentation.

E. Methods of Use

The compounds and pharmaceutical compositions disclosed herein have many features and uses, including but not limited to, self-healing or self-repairing (e.g., long-term retention within the joint), shear-thinning (e.g., dynamic response to joint biomechanics and injectability), and network formation (e.g., shock absorbance). The compounds and compositions can be used in applications in which HA is currently used. When used for cartilage/joint injuries, the intraarticular injection of self-healing HA materials can significantly reduce cartilage damage. Accordingly, the compounds and compositions provided herein can serve as a replacement for current viscosupplements, and can be used as point of care to treat joint injuries to prevent post-traumatic osteoarthritis, to treat osteoarthritis, to alleviate pain (e.g., pain associated with osteoarthritis), and the like. The compounds and compositions can also be used to provide lubrication to an eye, to treat dry eye diseases, and the like. Furthermore, the compounds and compositions can be used as dermal fillers to remove and/or reduce wrinkles, restore lost volume, smooth lines, soften creases, and/or enhance contours of the skin.

In an aspect, the disclosure provides a method of promoting and/or improving chondroprotection in a joint of a subject, the method comprising administering to the joint a therapeutically effective amount of a functionalized hyaluronic acid compound (e.g., a compound disclosed herein), or a composition comprising the compound. In some embodiments, the joint is a knee joint.

In another aspect, the disclosure provides a method of removing and/or reducing wrinkles, restoring lost volume, smoothing lines, softening creases, and/or enhancing contours of the skin of a subject, the method comprising administering to the skin of the subject a therapeutically effective amount of a functionalized hyaluronic acid compound (e.g., a compound disclosed herein), or a composition comprising the compound.

In another aspect, the disclosure provides a method of treating an injury in a subject, the method comprising administering to the subject a therapeutically effective amount of a functionalized hyaluronic acid compound (e.g., a compound disclosed herein), or a composition comprising the compound. In some embodiments, the injury comprises an injury to a joint, tendon or ligament. In some embodiments, the injury comprises a torn or ruptured anterior cruciate ligament or medial collateral ligament.

In another aspect, the disclosure provides a method of delivering a therapeutic agent to a subject, the method comprising administering a pharmaceutical composition comprising the therapeutic agent and a functionalized hyaluronic acid compound (e.g., a compound disclosed herein) to the subject. In some embodiments, the pharmaceutical composition is administered to a joint of the subject.

In another aspect, the disclosure provides a method of providing lubrication to a joint of a subject, the method comprising administering to the joint of the subject a therapeutically effective of a functionalized hyaluronic acid compound (e.g., a compound disclosed herein), or a composition comprising the compound.

In another aspect, the disclosure provides a method of providing lubrication to an eye of a subject, the method comprising administering to the eye of the subject a therapeutically effective of a functionalized hyaluronic acid compound (e.g., a compound disclosed herein), or a composition comprising the compound.

In another aspect, the disclosure provides a method of treating dry eye disease in a subject in need thereof, the method comprising administering to the subject a therapeutically effective of a functionalized hyaluronic acid compound (e.g., a compound disclosed herein), or a composition comprising the compound.

In another aspect, the disclosure provides a method of treating osteoarthritis in a subject in need thereof, the method comprising administering to the subject a therapeutically effective of a functionalized hyaluronic acid compound (e.g., a compound disclosed herein), or a composition comprising the compound.

In another aspect, the disclosure provides a method of alleviating pain in a joint of a subject, the method comprising administering to the joint of the subject a therapeutically effective amount of a functionalized hyaluronic acid compound (e.g., a compound disclosed herein), or a composition comprising the compound. In some embodiments, the pain is a result of osteoarthritis.

The following Examples are provided by way of illustration and not by way of limitation.

F. Examples

Abbreviations used in the Examples include the following: Boc is tert-butyloxycarbonyl; DCM is dichloromethane;

DMF is N,N-dimethylformamide; DMSO is dimethylsulfoxide; EDC is 1-ethyl-3-(3-dimethylaminopropyl) carbodiimide hydrochloride; NHS is N-hydroxysuccinimide; NMR is nuclear magnetic resonance; and RT is room temperature. Unless otherwise indicated, a Fourier transform infrared (FTIR) spectrometer (Nicolet 8700) with an attenuated total reflection (ATR) range of 4000 to 650 $cm^{-1}$ was used for all FTIR characterizations. Unless otherwise indicated, $^{1}H$ NMR were recorded by using a 500 MHz Agilent/Varian VNMRS spectrometer at room temperature.

Example 1

Synthesis of HA-UPy

Scheme 1.

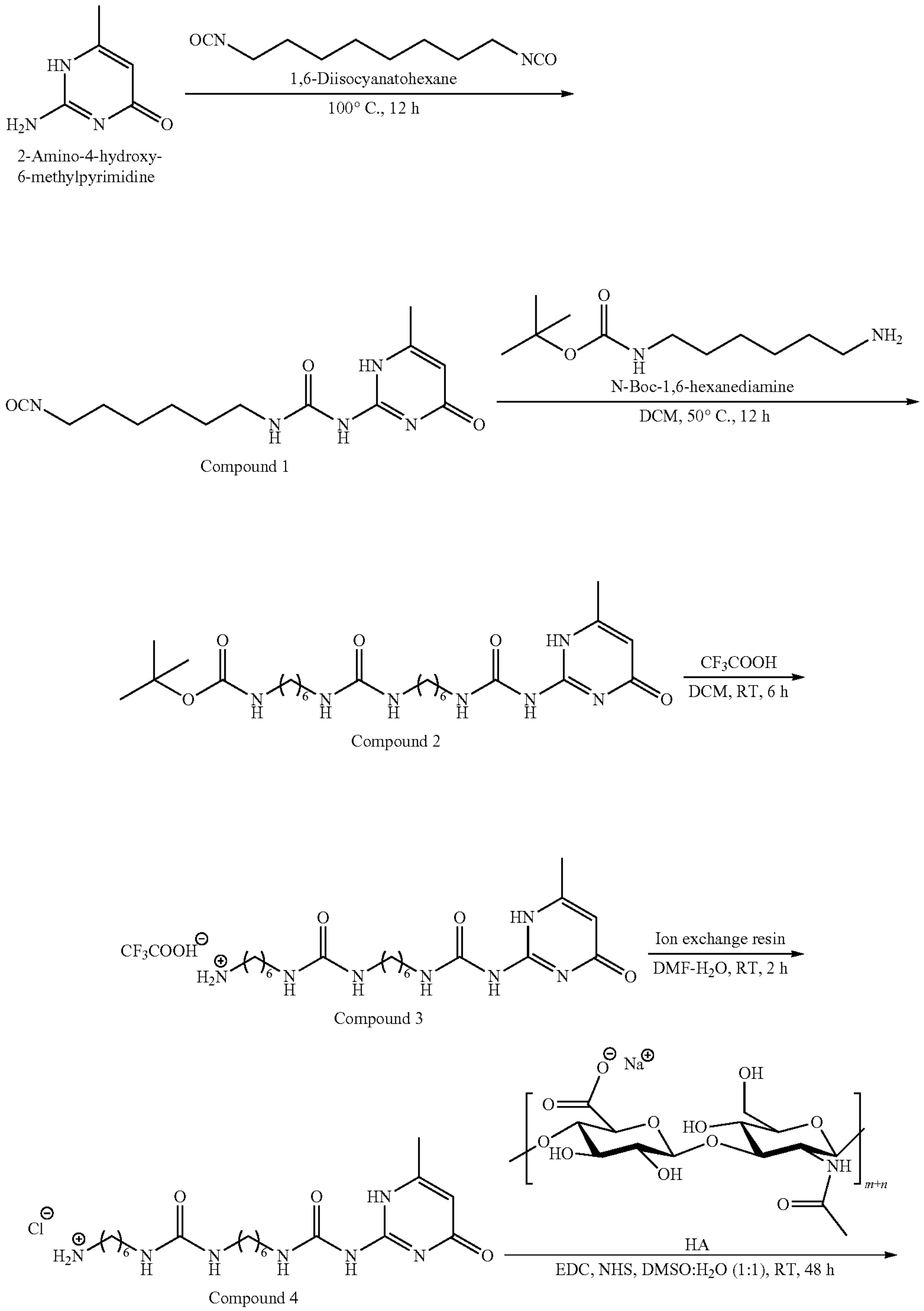

2-Amino-4-hydroxy-6-methylpyrimidine

Compound 1

Compound 2

Compound 3

Compound 4

-continued

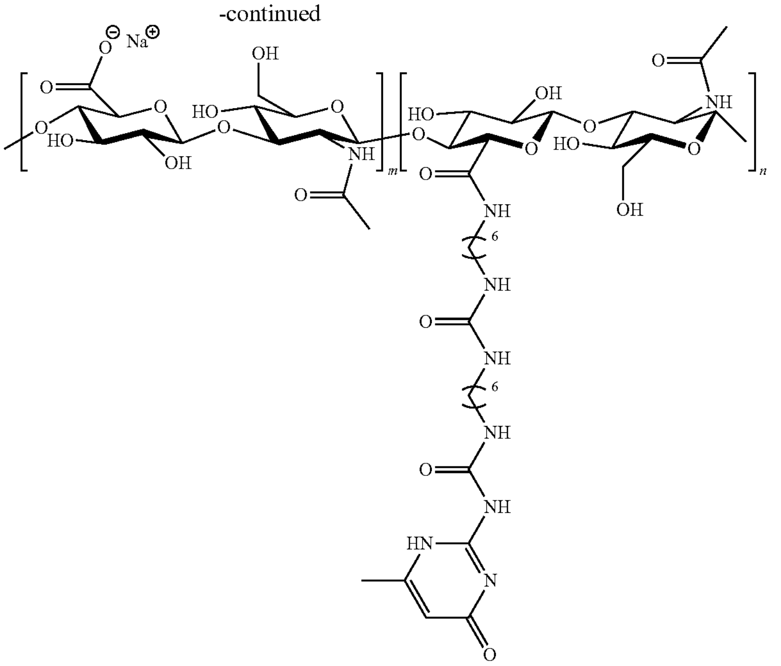

HA-UPy

Note that in Scheme 1, the product compound HA-UPy is illustrated as a block copolymer of unfunctionalized and functionalized repeat units. One skilled in the art will understand, however, that the actual product is a random copolymer of the indicated repeat units, and that the manner in which the product is shown in Scheme 1 is merely a convenient method of illustration.

A. Synthesis of UPy-bearing linker. A UPy-bearing linker was synthesized via a multi-step process (Dankers et al., *Biomaterials* 2006, 27, 5490; Hou et al., *Advanced Healthcare Materials* 2015, 4, 1491), illustrated in Scheme 1. Briefly, 2-amino-4-hydroxy-6-methylpyrimidine (Sigma, Cat. #A58003) (10 g, 0.08 mol) was dissolved in excess 1,6-diisocyanatohexane (Sigma, Cat. #52650) (107 g, 0.64 mol) and reacted at 100° C. overnight in argon environment. The product, termed Compound 1 in Scheme 1 (1-(6-isocyanatohexyl)-3-(6-methyl-4-oxo-1,4-dihydropyrimidin-2-yl) urea), was precipitated in n-pentane, filtered, and dried. Characterization data for Compound 1: $^1H$ NMR (DMSO-$d^6$): δ (ppm)=11.52 (s, 1H, —$(CH_3)C$—NH—), 9.69 (s, 1H, —$CH_2$—NH(CO)—NH—), 7.35 (s, 1H, —$CH_2$—NH(CO)—NH—), 5.77 (s, 1H, —CH═$C(CH_3)$—), 3.29-3.36 (m, 4H, —NH—(CO)—NH—$CH_2$—+—$CH_2$—NCO), 2.11 (s, 3H, —$CH_3$), 1.44-158 (m, 4H, —$CH_2$—$CH_2$—$(CH_2)_2$—$CH_2$—$CH_2$—NCO), 1.27-1.37 (m, 4H, —$CH_2$—$CH_2$—$(CH_2)_2$—$CH_2$—$CH_2$—NCO). FTIR (ATR): ν ($cm^{-1}$)=2271 (NCO stretch), 1696 (UPy), 1666 (UPy), 1576 (UPy), 1522 (UPy), 1464, 1357, 1312, 1252.

Compound 1 (5 g, 0.017 mol) was mixed with N-Boc-1,6-hexanediamine (TCI Chemicals, Cat. #A1375) (5.5 g, 0.025 mol) in anhydrous dichloromethane (~75 mL) and kept at 50° C. overnight to yield Compound 2 (tert-butyl(6-(3-(6-(3-(6-methyl-4-oxo-1,4-dihydropyrimidin-2-yl) ureido)hexyl) ureido)hexyl)carbamate), which was precipitated in chilled diethyl ether, filtered, and dried. NMR and FTIR spectra are provided in supplementary information (data summarized below). Characterization data for Compound 2: $^1H$ NMR (DMSO-$d^6$): δ (ppm)=11.57 (br.s, 1H, —$(CH_3)C$—NH—), 9.65 (s, 1H, —$CH_2$—NH(CO)—NH—), 7.40 (br. s, 1H, —$CH_2$—NH(CO)—NH—), 6.75 (m, 3H, —C(O)—NH$(CH_2)_6$NH—C(O)—+$(CH_3)_3$—(O)C═O—NH—), 5.77 (s, 1H, —CH═$C(CH_3)$—), 3.11-3.14 ($(CH_3)_3$—(O)C═O—NH—$CH_2$—), 2.86-2.97 (m, 6H, —NH—(CO)—NH—$CH_2$—+—$CH_2$—NH—(CO)—NH—), 2.10 (s, 3H, —$CH_3$), 1.21-1.46 (m, 25H, —NH—$CH_2$—$CH_2$—+—$CH_2$—$CH_2$—$(CH_2)_2$—$CH_2$—$CH_2$—+$(CH_3)_3$—(O)C═O—NH—). FTIR (ATR): ν ($cm^{-1}$)=1701 (UPy), 1665 (UPy), 1576 (UPy), 1520 (UPy), 1460, 1355, 1311, 1254.

Compound 2 (5 g) was dispersed in dichloromethane (90 mL). Trifluoroacetic acid (TCI Chemicals, Cat. #A12198) (10 mL) was added to the suspension and stirred vigorously at room temperature for ~6 h. Following the reaction, the dichloromethane and trifluoroacetic acid were removed using a rotavapor. The solid residue was dissolved in minimum amount of dichloromethane and precipitated in excess chilled acetone. The product, Compound 3 (1-(6-(3-(6-aminohexyl)ureido)hexyl)-3-(6-methyl-4-oxo-1,4-dihydropyrimidin-2-yl)urea trifluoro acetic acid) was filtered, washed repeatedly with acetone and dried in vacuum. Characterization data for Compound 3: $^1H$ NMR (DMSO-$d^6$): δ (ppm)=9.77 (br.s, 1H, Enol —CH═C(OH)—), 7.55-7.72 (br. m, 4H, —$CH_2$—NH(CO)—NH—+—$CH_2$—NH(CO)—NH—+—C(O)—NH$(CH_2)_6$NH—), 5.79 (s, 1H, —CH═$C(CH_3)$—), 3.10-3.14, —CONH—$(CH_2)_5$—$CH_2$—NHCO—), 2.94-2.97 (m, 4H, —CONH—$CH_2$—$(CH_2)_4$—$CH_2$—NHCO—), 2.73-2.80 (m, 2H, $N^+H_3$—$CH_2$—$(CH_2)_5$—NHCO—), 2.11 (s, 3H, —$CH_3$), 1.22-1.54 (m, 16H, —$CH_2$—$(CH_2)_4$—$CH_2$—). FTIR (ATR): ν ($cm^{-1}$)=1710 (UPy), 1670 (UPy), 1580 (UPy), 1520 (UPy), 1462, 1355, 1312, 1258, 1201 (TFA Salt), 1135 (TFA Salt).

The dried Compound 3 was treated with Amberlite IRA 400 chloride ion exchange resin (Sigma, Cat. #247669) in dimethylsulfoxide-water mixture (1:1) at room temperature for 2 h. The resin was filtered off to provide the solution of the UPy-bearing linker (Compound 4, 1-(6-(3-(6-aminohexyl)ureido)hexyl)-3-(6-methyl-4-oxo-1,4-dihydropyrimidin-2-yl)urea HCl). Characterization data for Compound 4: $^1$H NMR (DMSO-$d^6$): δ (ppm)=11.64 (m, 1H, —($CH_3$)C—NH—), 9.76 (s, 1H, —$CH_2$—NH(CO)—NH—), 7.82 (m, 2H, —$CH_2$—NH(CO)—NH—), 7.71-7.95 (m, 2H, —C(O)—NH($CH_2$)$_6$NH—C(O)—), 5.76 (s, 1H, —CH═C($CH_3$)—), 3.33 (m, 3H, $N^+H_3$—($CH_2$)$_5$—$CH_2$—NHCO—), 3.10-3.14, —CONH—($CH_2$)$_5$—$CH_2$—NHCO—), 2.94-2.97 (m, 4H, —CONH—$CH_2$—($CH_2$)$_4$—$CH_2$—NHCO—), 2.73-2.77 (m, 2H, $N^+H_3$—$CH_2$—($CH_2$)$_5$—NHCO—), 2.10 (s, 3H, —$CH_3$), 1.22-1.56 (m, 16H, —$CH_2$—($CH_2$)$_4$—$CH_2$—). FTIR (ATR): ν ($cm^{-1}$)=1699 (UPy), 1669 (UPy), 1575 (UPy), 1520 (UPy), 1466, 1357, 1312, 1256.

Figure 2A:
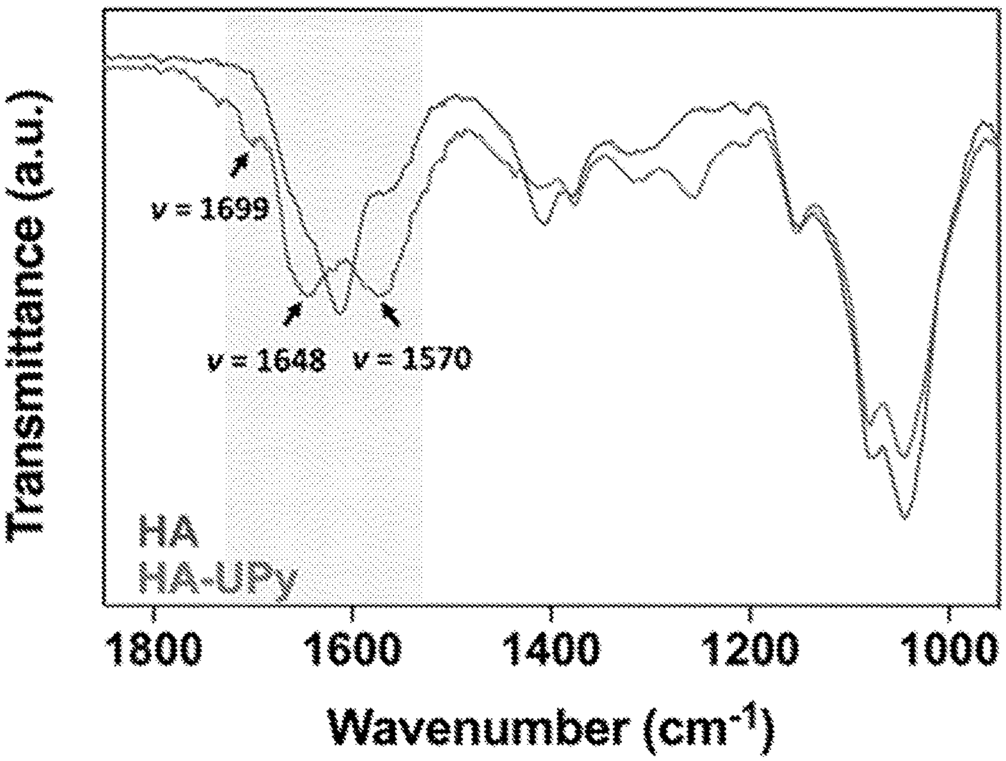
FIGS. 2A-2B show a Fourier transform infrared (FTIR) spectrum of HA and HA-UPy (FIG. 2A) and $^1H$ NMR spectra of HA and HA-UPy, with pyrimidinone protons of UPY at δ 6.41 ppm (=CH—) and δ 2.69 ppm (—$CH_3$) (FIG. 2B).
Figure 2B:
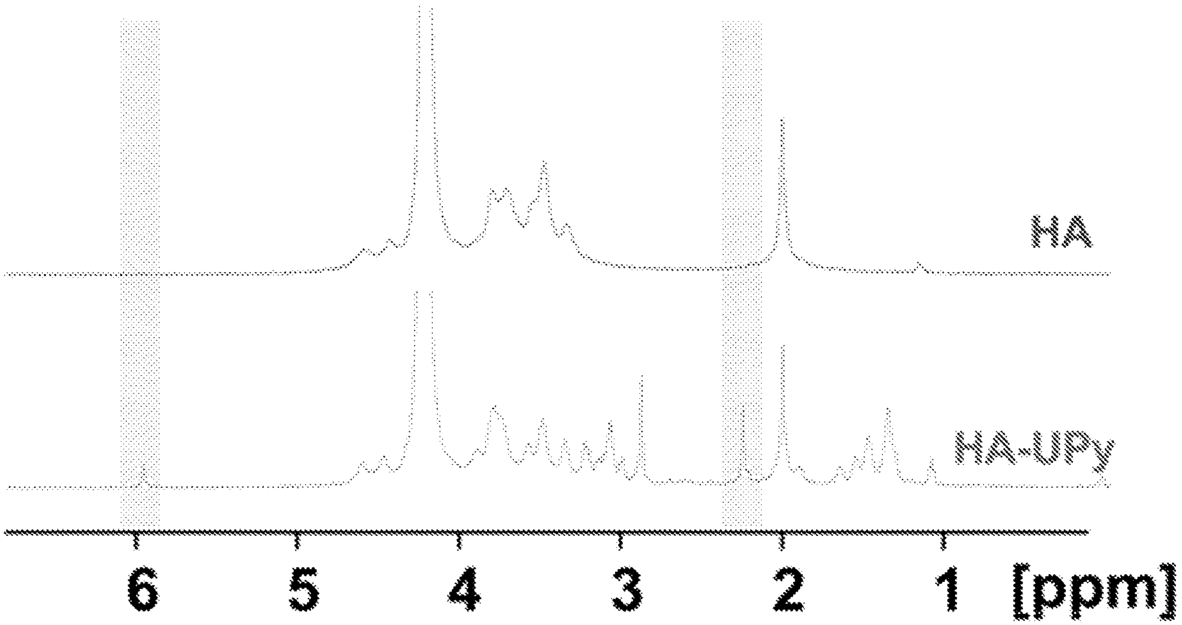

B. Synthesis of HA-UPy. To synthesize HA-UPy, the UPy-bearing linker was reacted with sodium hyaluronate (HA, MW 200 kDa; Lifecore Biomedical, Cat #HA200K) using EDC/NHS chemistry. Briefly, HA was dissolved in a mixture of deionized water and DMSO (1:1) at 5 mg/mL, to which 1-ethyl-3-(3-dimethylaminopropyl)carbodiimide hydrochloride (EDC, TCI Chemicals, Cat. #D1601), N-hydroxysuccinimide (NHS, Sigma, Cat. #130672), and Compound 4 (each 1 equivalent with respect to the carboxylic acid groups of HA) were sequentially added at 15 min intervals. The reaction was carried out at room temperature for 48 h, and the resulting HA-UPy product was purified via dialysis against water and lyophilized. Successful conjugation of UPy to HA was verified by a combination of FTIR and NMR spectroscopy (FIGS. 2A and 2B, respectively). The FTIR spectrum of the product confirmed UPy conjugation with new peaks appearing at 1699, 1648, and 1570 $cm^{-1}$, corresponding to pyrimidinone C═O stretching, urea C═O stretching, and pyrimidinone C═N stretching, respectively. The extent of UPy conjugation was quantified via $^1$H NMR spectroscopy by comparing the integrated peak area of the pyrimidinone protons in a UPy unit (—NH—C($CH_3$)—CH—CO—, 1H, δ 5.95; —NH—C($CH_3$)—CH—CO—, 3H, δ 2.23) to that of the acetyl protons in HA's N-acetyl-D-glucosamine unit (—NH—CO—$CH_3$, 3H, δ 1.98). A grafting density of ~24±1% per dimeric repeating unit of HA was determined.

C. Synthesis of HA-Cy7 and HA-UPy-Cy7. Cyanine 7 (Cy7, Lumiprobe, Cat. #55000) dye was conjugated onto HA and HA-UPy via amide coupling reaction. Briefly, HA or HA-UPy was dissolved in a mixture of deionized water and DMSO (1:1) at 5 mg/mL. EDC (1 equivalent with respect to the carboxylic acid group of HA or HA-UPy), NHS (1 equivalent with respect to the carboxylic acid group of HA or HA-UPy), and Cy7 (0.04 equivalent with respect to the carboxylic acid group of HA or HA-UPy) were subsequently added to the polymer solution. After 48 h of reaction at room temperature, the mixture was dialyzed extensively with water for 4 d. The solutions were then freeze-dried to obtain HA-Cy7 or HA-UPy-Cy7. The product was characterized by a combination of FTIR and NMR spectroscopy, and the extent of dye conjugation was quantified via UV/vis absorption spectroscopy.

Example 2

Characterization of HA-UPy Using 200 kDa HA

I. Materials and Methods

A. Gelation of HA and HA-UPy molecules. HA and HA-UPy solutions of various concentrations (2 wt %, 5 wt %, and 10 wt %) were prepared by dissolving the required weight of the molecules in phosphate-buffered saline (PBS). For visualizing gelation, food dye was added. Eppendorf tubes containing the solutions were inverted to visualize the flow under gravity, and images were taken both immediately following dissolution and after 24 h.

B. Rheological analysis. Both HA-UPy and HA were prepared in PBS and subjected to rheological measurements as a function of concentration by using a rotational rheometer (AR-G2, TA Instruments). Each sample was loaded on a parallel plate geometry (Al, diameter 8 mm), and the oscillatory frequency sweep measurements were conducted at 1% strain amplitude with frequencies ranging from 0.1 to 10 Hz. Strain sweep measurements were conducted at a frequency of 1 rad/s and over 1 to 1000% strain. To assess the shear-thinning behavior, the steady-state viscosities of HA-UPy and HA at 10 wt % were measured at 1% strain as a function of shear rate (0.1 to 100 $s^{-1}$). To evaluate the recovery of HA-UPy and HA at 10 wt %, step-strain measurements were recorded at 1 rad/s with a range of consecutive strains (1%, 100%, 1%, 1000%, and 1%) applied each for 180 s. To examine hysteresis of HA-UPy, 6 cycles of alternating low (1%) and high (500%) strain were applied. All samples were measured in triplicate.

C. Injectability of HA-UPy. 10 wt % HA-UPy molecules were generated in PBS, loaded into a Hamilton syringe, and extruded into different shapes through a 26G needle.

D. Self-healing of HA-UPy. To examine the self-healing phenomenon, hydrogel pieces were generated from HA-UPy (10 wt % and colored differently for visualization). Several pieces of the hydrogel were gently brought into contact with one another.

E. Enzymatic degradation. The stability of HA-UPy was evaluated in the presence of hyaluronidase (Sigma, Cat. #H3506). In brief, HA-UPy and HA were dissolved in 20 mM sodium acetate buffered solution (pH 6) at 2.5 mg/mL supplemented with 1 kU/mL hyaluronidase. Each sample was sealed in a benzoylated dialysis membrane (MWCO~2 kDa; Sigma, Cat. #D2272) and dialyzed against sodium acetate buffer at 37° C. for 48 h. The dialysate containing the degradation products was collected for uronic acid assay. The solution was mixed with 12.5 mm sodium tetraborate (Alfa Aesar, Cat. #A16176) in concentrated sulfuric acid at a volume ratio of 1:6 and heated at 100° C. for 10 mins. Upon cooling, 0.15% m-hydroxydiphenyl (Sigma, Cat.#262250) in 0.5% NaOH was added and its absorbance was measured at 520 nm using UV/vis spectroscopy. Known concentrations of HA (0-2.5 mg/mL) were used to generate the standard curve.

F. Free radical scavenging. The ability of HA-UPy to scavenge free radicals was analyzed by using 1,1-diphenyl-2-picrylhydrazyl (DPPH; Sigma, Cat. #D9132) or Fenton reagent as free radical sources. For the DPPH assay, 10 wt % HA-UPy or HA was fully soaked in ethanol containing 0.1 mM DPPH at 37° C. for 1 h in the dark. Saline of the same volume was used as the control. The absorbance of DPPH solution at 517 nm before ($Abs_0$) and after ($Abs_t$) the incubation was recorded using UV/vis. The DPPH scavenging effect was determined as $$\frac{Abs_0 - Abs_t}{Abs_0} \times 100\%.$$

The average reduction in absorbance in the saline group was subtracted from the HA and HA-UPy groups to normalize for dilution. All samples were measured in triplicate.

To examine the hydroxyl radical scavenging effect, the Fenton reagent was prepared as described elsewhere. Briefly, a reaction mixture consisting of 1 mm ferric chloride (Sigma, Cat.#157740), 30 mm deoxyribose (Sigma, Cat. #121649), 1 mM ascorbic acid (Sigma, Cat. #A92902), 1 mm EDTA (Sigma, Cat. #E9884) and 20 mM $H_2O_2$ was prepared in 0.2 M phosphate buffer. The reaction mixture (1 mL) was added to either 10 wt % HA-UPy or 0.2 M phosphate buffer control (100 μL). The gel or phosphate buffer was incubated at room temperature for 1 hon a shaker plate. Following the incubation period, the reaction mixture (500 μL) was taken from each tube and mixed with a solution of 0.25% thiobarbituric acid (500 μL; TBA; Sigma, Cat. #T5500) in 15% trichloroacetic acid (TCA; Sigma, Cat. #T6399). The mixtures were incubated in a silicon oil bath at 100° C. for 20 min. The absorbance was measured at 532 nm using a UV/Vis spectrophotometer, with a lower absorbance corresponding to fewer hydroxyl radicals. All samples were measured in triplicate.

Following exposure to the Fenton reaction mixture, the samples were washed in PBS, freeze dried, and reconstituted in saline at a concentration of 10 wt %. Corresponding HA-UPy samples were similarly incubated in phosphate buffer alone (controls), followed by washing in PBS, freeze drying, and reconstituting in saline. A frequency sweep was performed as previously described at 1% strain under oscillatory mode with frequency varying from 0.1 to 10 Hz. The storage moduli (G') at 1 Hz was compared for the free radical-treated HA-UPy and corresponding HA-UPy control.

G. Explant coculture. To examine the biocompatibility of HA-UPy, rat tibial condyles were harvested and cultured in chondrocyte medium with or without HA-UPy (10 wt %, 50 μL) for 7 d. The cartilage explants were then rinsed and incubated in PBS containing 0.05% calcein acetoxymethyl and 0.2% ethidium homodimer-1 from the Live/Dead Cell Viability Assays kit (Life technologies, Cat. #L3224) for 30 min. After thorough washing, the explants were sectioned and imaged using a Keyence (BZ-X710) microscope.

H. Coefficient of friction between cartilage explants. Two flat cartilage discs (8-mm diameter and 0.5-mm thickness, porcine, 3-year-old) were mounted on sandpaper-covered parallel plates using cyanoacrylate glue, with the articular surfaces facing each other. After equilibration in saline, HA, HA-UPy (10 wt %), or saline was introduced at the cartilage-cartilage interface, the discs were brought into contact and programmed to move against each other by using a rotational rheometer. Both normal stress and shear stress were recorded under shear rates ranging from 0.1 to 1 $s^{-1}$. The coefficient of friction (μ) at the cartilage-cartilage interface was calculated using the equation, μ=(Shear stress)/(Normal stress).

II. Results and Discussion

A. HA-UPy Molecules Form Supramolecular Networks and Exhibit Self-Healing

Figure 3:
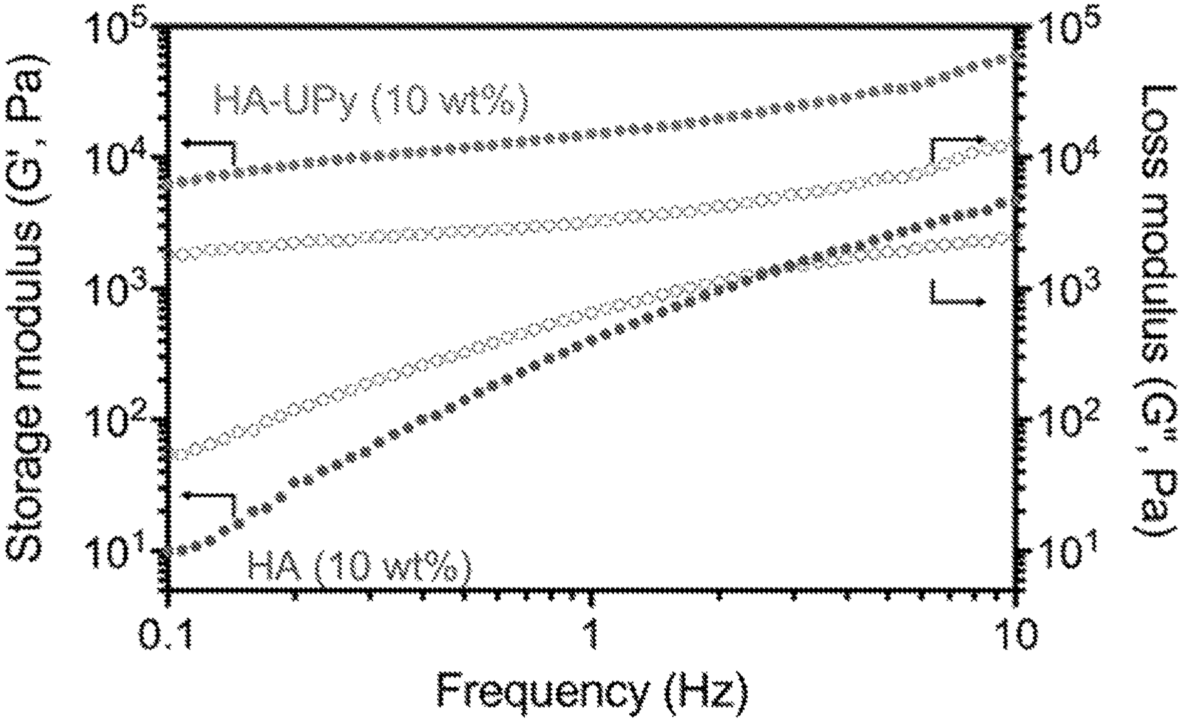
FIG. 3 shows data for storage (G') and loss (G") moduli of HA-UPy and HA in a frequency sweep measurement.
Figure 4:
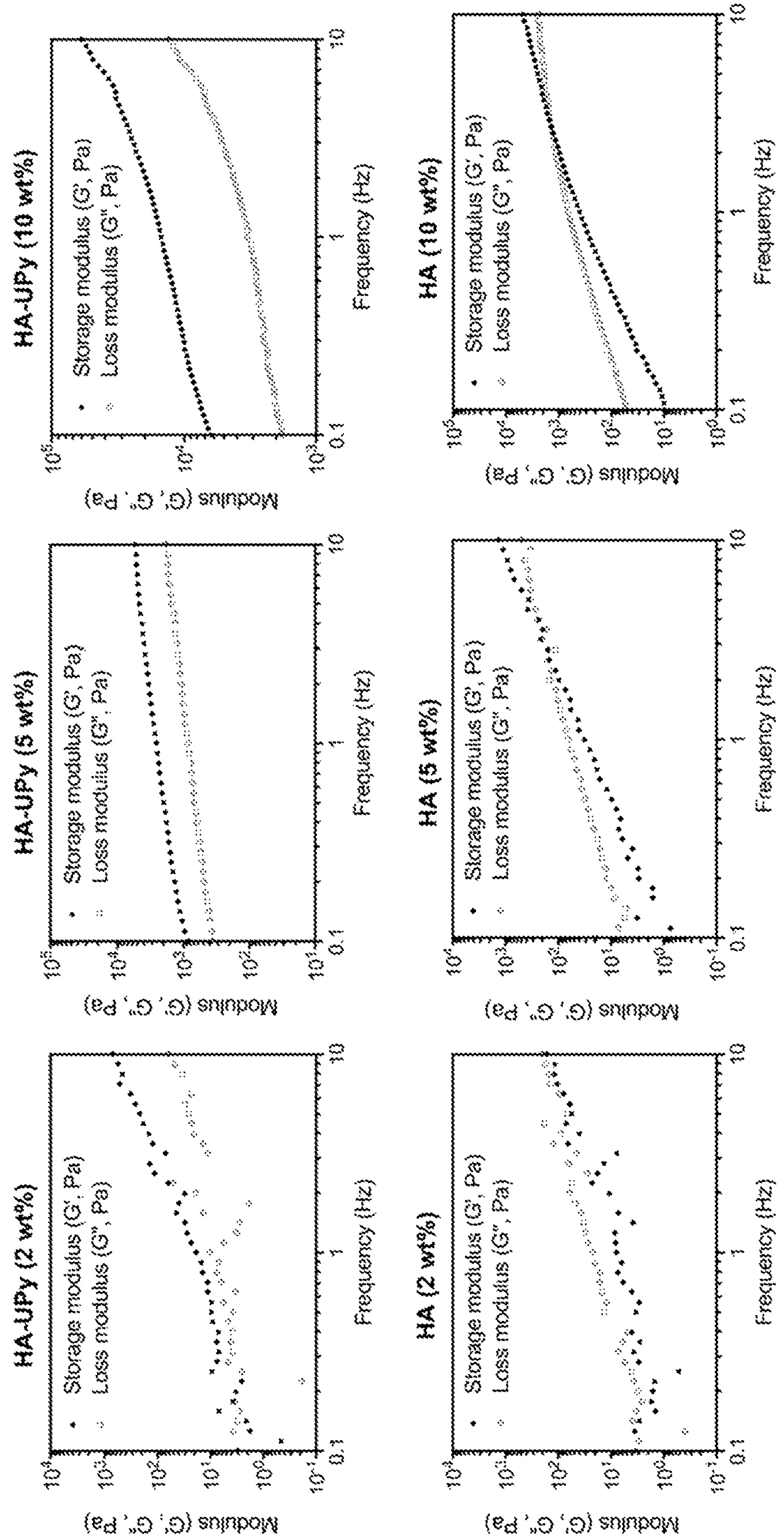
FIG. 4 shows data from frequency sweep measurements for HA and HA-UPy at different concentrations, showing the evolution of storage (G') and loss (G") moduli as a function of frequency.
Figure 5:
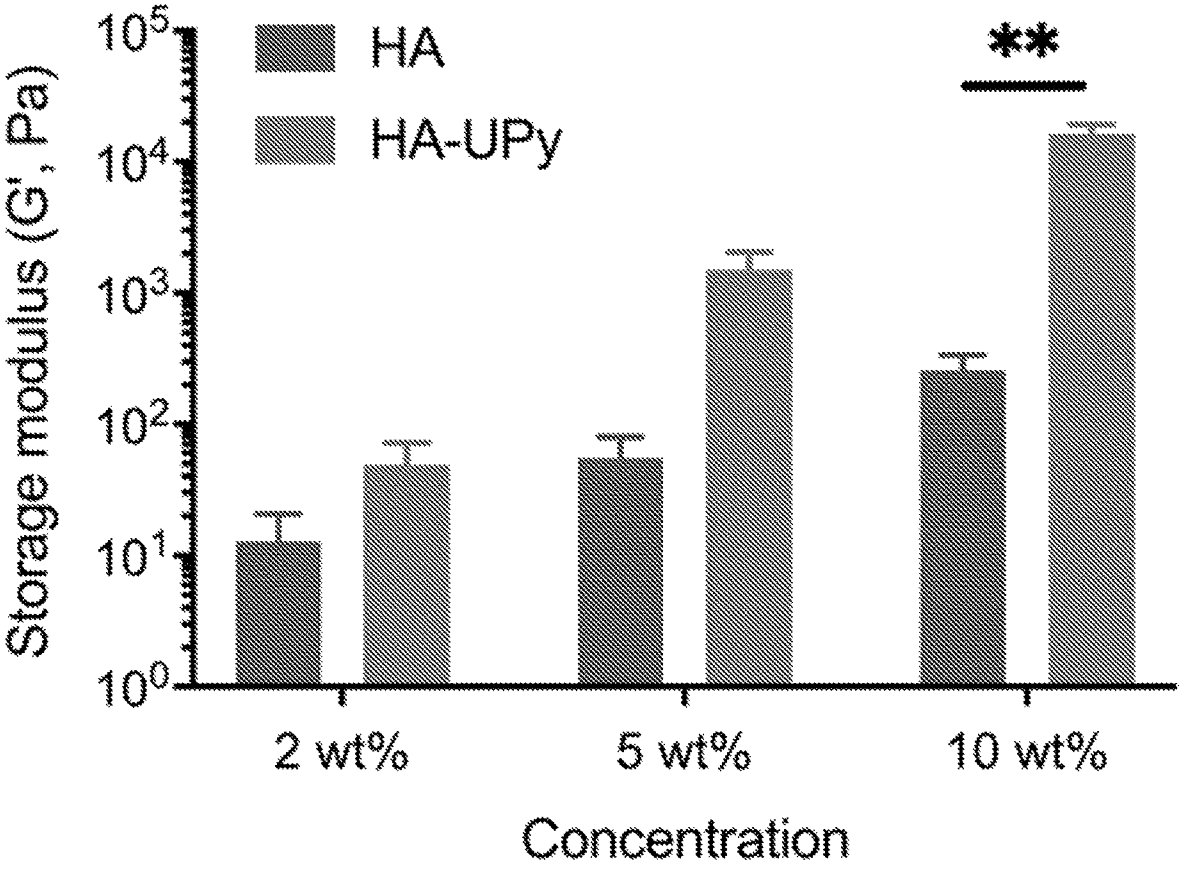
FIG. 5 shows data for storage modulus (G') of HA-UPy and HA at a frequency of 1 Hz and 1% strain as a function of concentration. Two-way ANOVA with Bonferroni multiple comparisons test was used for statistical analysis. **P<0.01.
Figure 6:
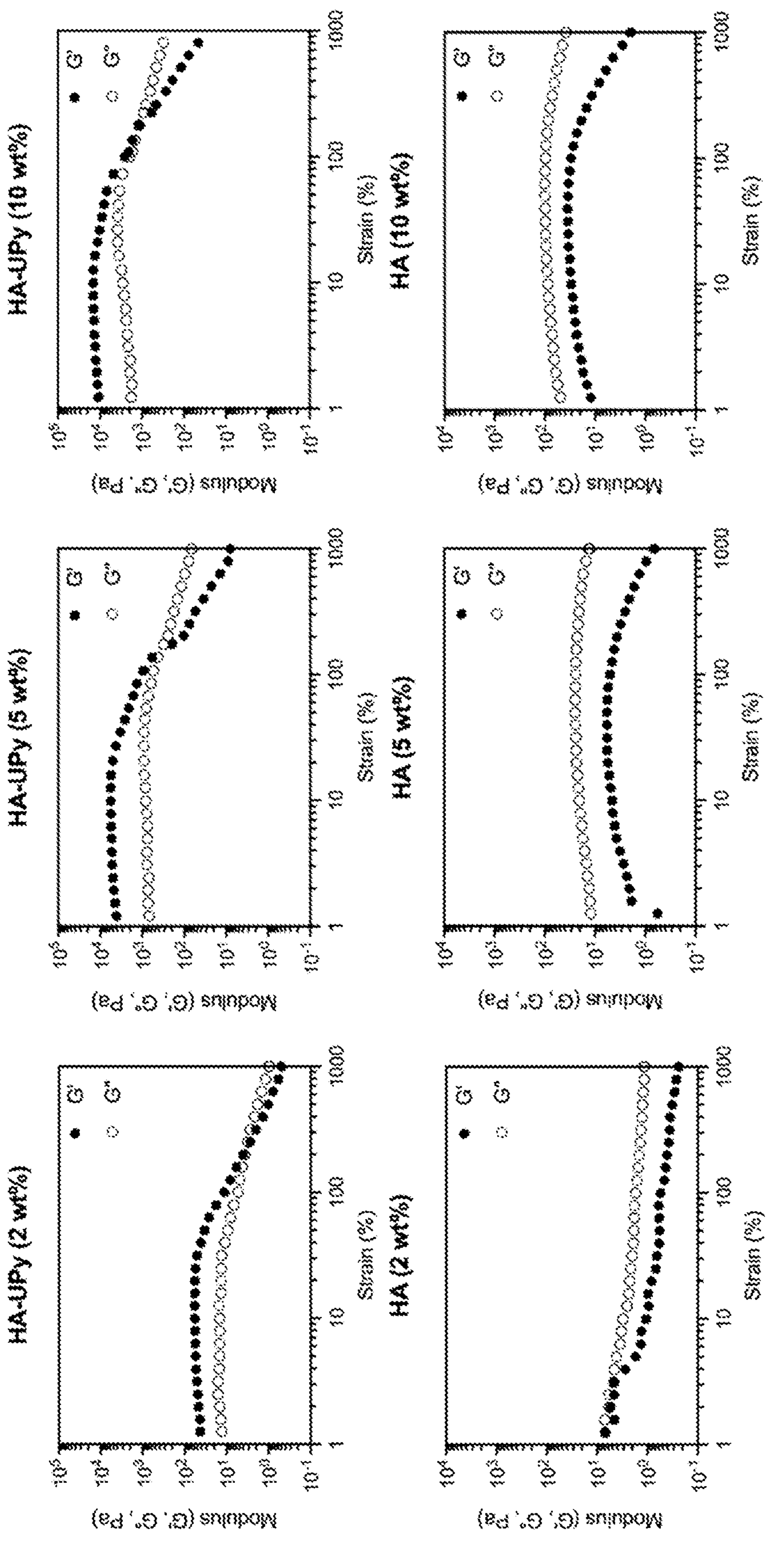
FIG. 6 shows data from strain sweep measurements for HA and HA-UPy at different concentrations showing storage (G') and loss (G") moduli as a function of strain.

The UPy-mediated non-covalent interactions among the polymer chains can facilitate self-assembly of HA molecules into dynamic networks (i.e., soft gels), which were characterized by rheological measurements. To study the effect of polymer concentration, solutions of HA-UPy and HA were prepared at three concentrations (2, 5, and 10 wt %) in phosphate-buffered saline (PBS). The frequency sweep (0.1-10 Hz) measurements of HA-UPy and unmodified HA showed that HA-UPy samples exhibited higher G' (storage modulus) and G" (loss modulus) at all frequencies while the HA samples behaved more like a viscous liquid (FIG. 3 and FIG. 4, and Table 1). Furthermore, the storage modulus, determined at 1 Hz, of the HA-UPy samples increased with increasing concentration (FIG. 5). The oscillation frequency of 1 Hz was chosen because it is within the range of typical walking frequencies. The strain sweep measurements of HA-UPy and unmodified HA at various concentrations are shown in FIG. 6. The concentration-dependent network formation was also visualized by inverting the tubes containing the polymer solutions. The samples containing HA-UPy showed solid-like behavior at higher concentrations and did not flow like a liquid. In contrast, the samples containing unmodified HA behaved like a viscous liquid at all concentrations, with the 10 wt % solution taking a longer time to flow. These observations for the HA-UPy samples are consistent with network formation, which arises from quadruple hydrogen bonding between the UPy moieties. Further experiments were carried out using 10 wt % HA and HA-UPy.

TABLE 1

G', G", and delta of HA and HA-UPy at different concentrations measured at 1 Hz

| Concentration | Sample | G' (Pa) | G" (Pa) | tan (delta) |
|---|---|---|---|---|
| 2 wt % | HA | 12 ± 9 | 16 ± 5 | N/A |
| | HA-UPy | 49 ± 20 | 27 ± 10 | 0.58 ± 0.05 |
| 5 wt % | HA | 51 ± 30 | 95 ± 50 | 1.9 ± 0.3 |
| | HA-UPy | 1500 ± 600 | 550 ± 200 | 0.38 ± 0.03 |
| 10 wt % | HA | 260 ± 80 | 470 ± 100 | 2.0 ± 0.2 |
| | HA-UPy | 16000 ± 3000 | 3500 ± 700 | 0.21 ± 0.004 |

Figure 7:
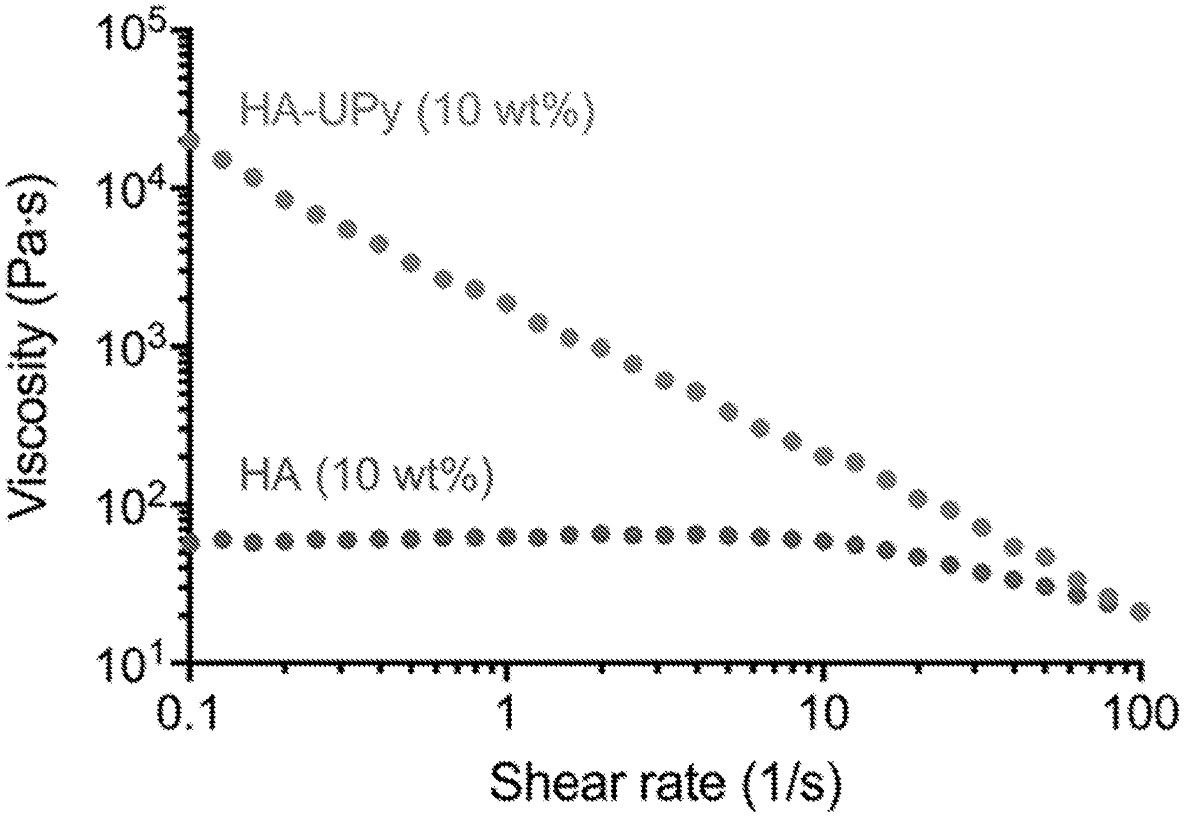
FIG. 7 shows viscosity changes of HA-UPy and HA as a function of shear rate.
Figure 8:
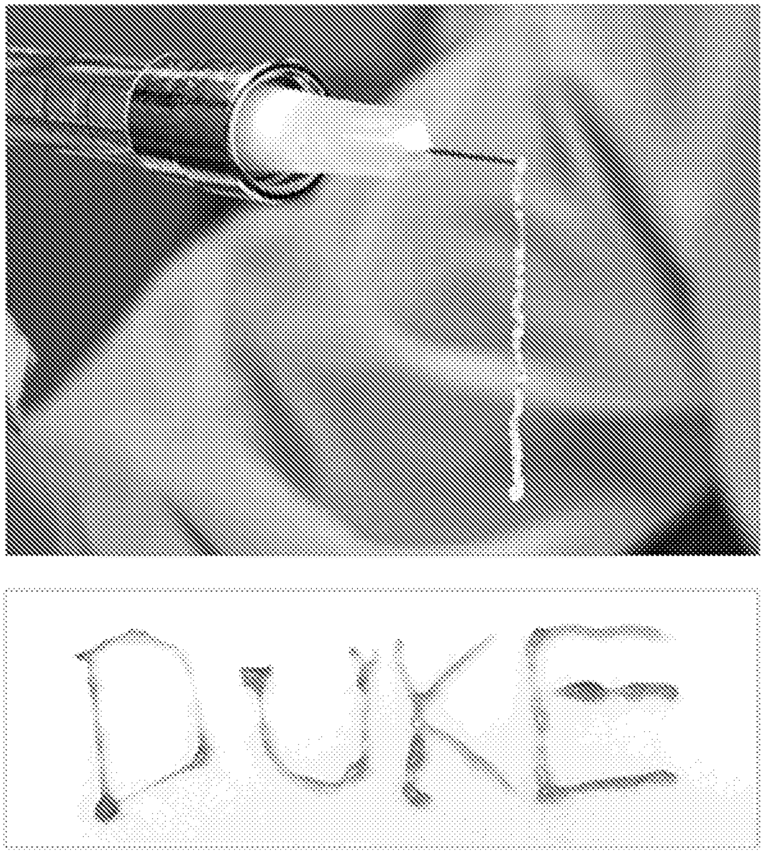
FIG. 8 shows that HA-UPy (10 wt %) was easily extruded through a 26G needle into "DUKE" letters.

Because the UPy-mediated network formation is dynamic, the HA-UPy samples should show shear-thinning and self-healing functions. As expected, the viscosity of the HA-UPy samples decreased with increasing shear rate, showing a characteristic shear-thinning behavior which results from destruction of the physical crosslinks by the applied shear stresses (FIG. 7). In contrast, the shear rate-dependent viscosity of the corresponding HA solution is consistent with that of a viscous liquid. The HA-UPy samples (10 wt %) were easily ejected through a 26G hypodermic needle with minimal resistance (FIG. 8). The extruded HA-UPy formed a stable network at rest, which enabled the "printing" of different shapes (FIG. 8).

Figure 9:
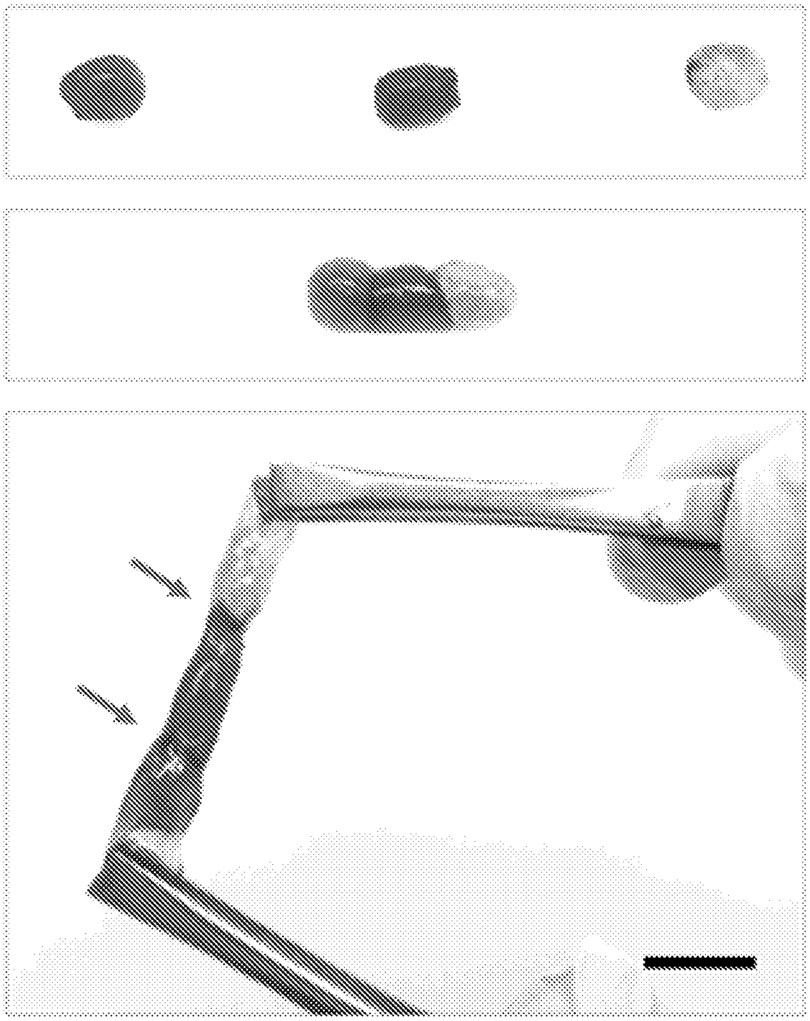
FIG. 9 shows separate pieces of 10 wt % HA-UPy hydrogels healed together with interfaces indicated with arrows. Scale bar: 1 cm.
Figure 10:
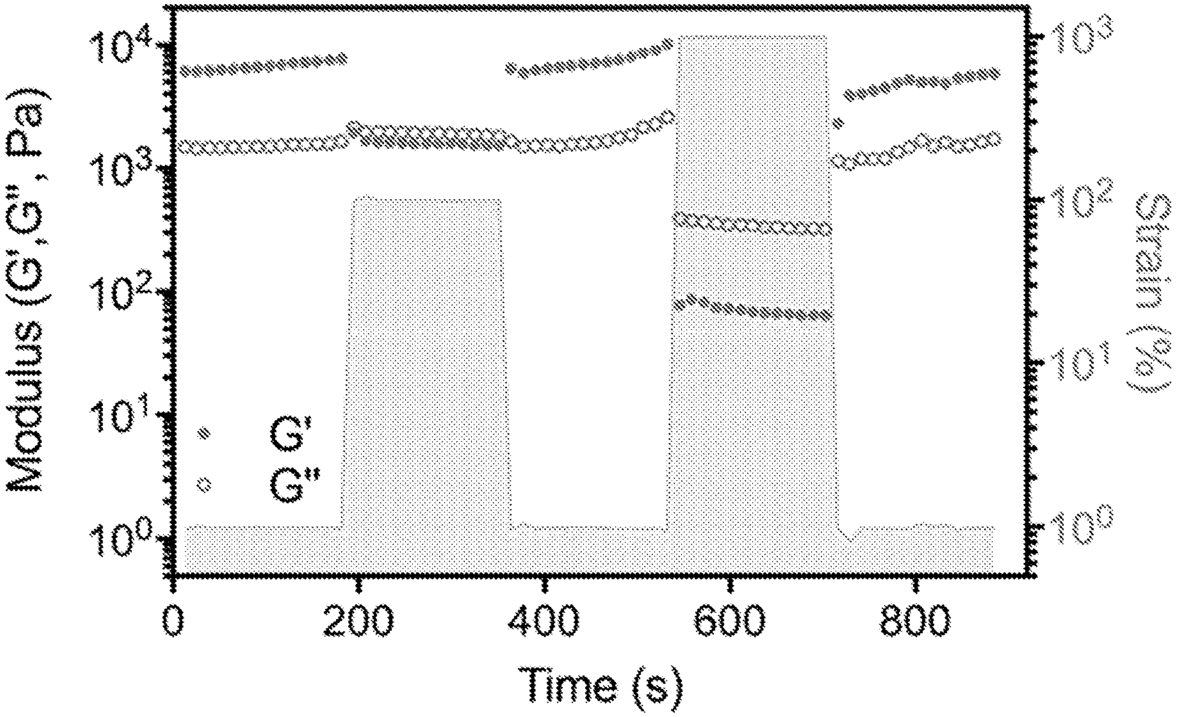
FIG. 10 shows data from step-strain measurements for 10 wt % HA-UPy.
Figure 11:
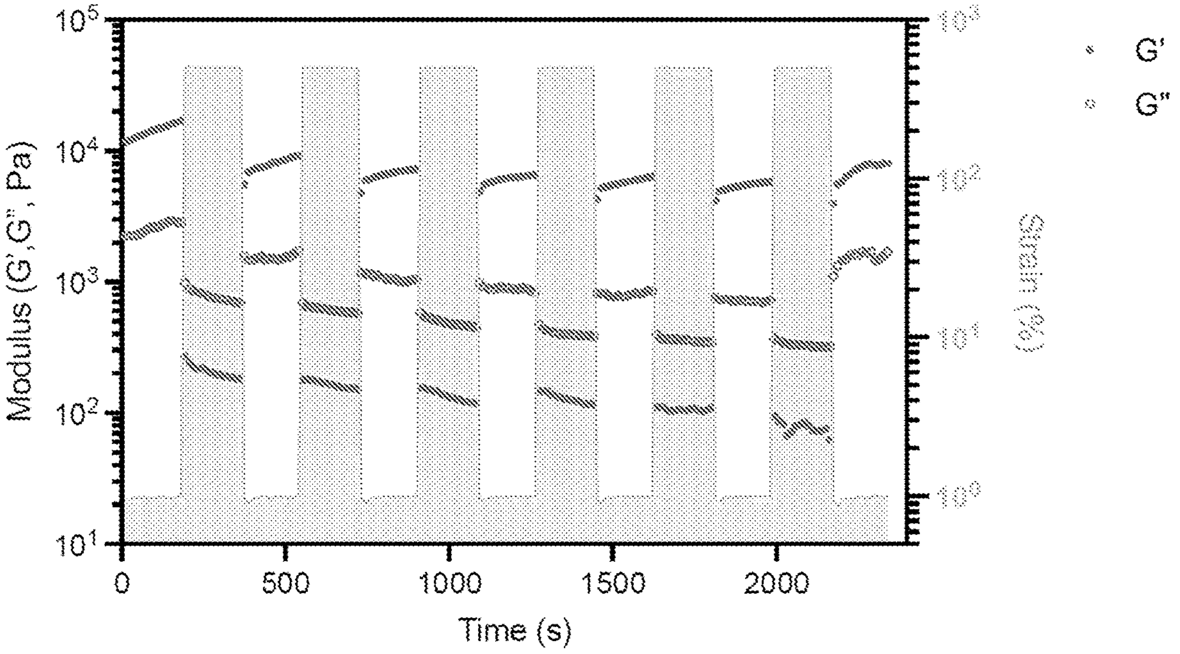
FIG. 11 shows data demonstrating that HA-UPy returns to original G' value following six cycles of low (1%) and high (500%) strains, indicating complete recovery of the network.

The self-healing of HA-UPy was examined by bringing multiple pieces of HA-UPy hydrogels into close contact, which showed instantaneous healing (FIG. 9). Furthermore, step-strain measurements were used to confirm the UPy-mediated self-healing of HA-UPy and dynamic networks, wherein 10 wt % HA-UPy samples were subjected to alternating step strains of 1 to 100% and 1 to 1000% (FIG. 9). The storage modulus (G') values of the HA-UPy samples dropped to that of the loss modulus (G") at a strain γ=100%, indicating network disruption (FIG. 10). When the strain was removed, the HA-UPy molecules re-organized and formed a new network structure instantaneously with a 100% recovery of G'. Increasing the strain rate to 1000% induced more network destruction as indicated by the drop of the storage modulus to ~100 Pa, with a corresponding inversion of G' and G", suggesting liquid-like flow behavior. Despite the large strain (γ=1000%), prompt recovery of the network structure was observed upon the removal of the strain. Additionally, experiments were performed in which a low (1%) and high (500%) strain were alternatingly applied over multiple cycles to determine whether the HA-UPy sample would recover its storage modulus after repeated network disruptions. These studies showed complete network formation without hysteresis as indicated by the G', which maintained its original value at 1% strain following repeated network disruption at $\gamma$=500% (FIG. 11).

B. Self-Healing HA Exhibits Enhanced Lubrication

Figure 12:
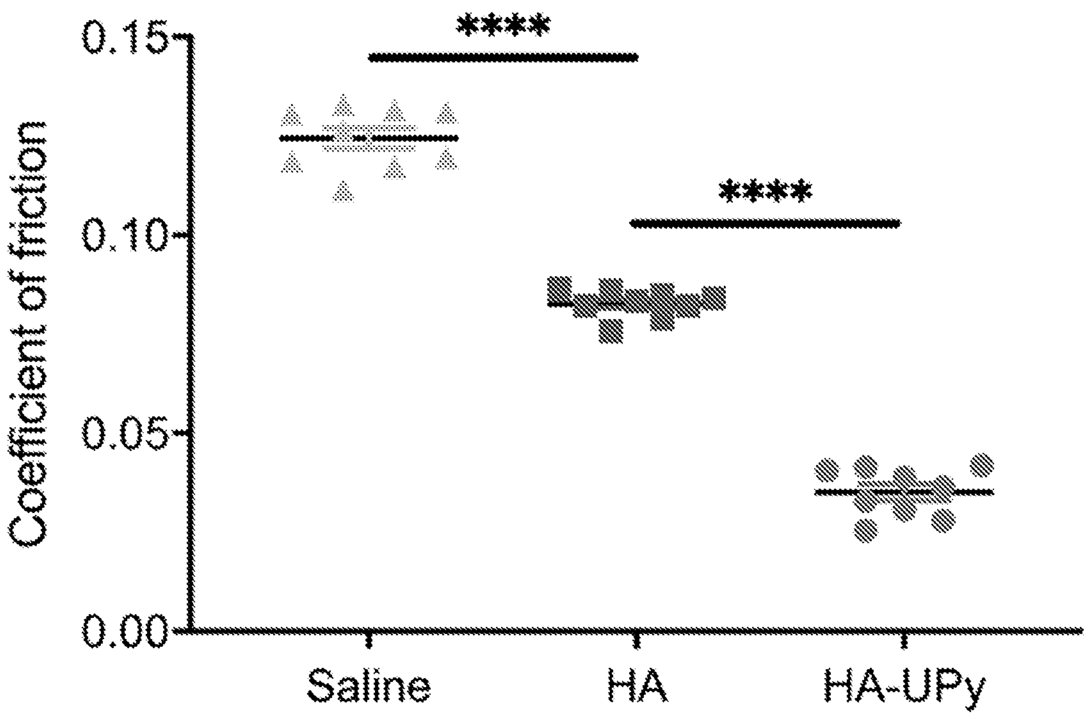
FIG. 12 shows coefficients of friction at the cartilage-cartilage interface in the presence of HA-UPy, HA, and saline. One-way ANOVA test was used for statistical analysis. ****P<0.0001.

Effectiveness of the biolubricant to reduce friction between the articular surfaces is key to its application in improving joint function. It was thus investigated whether UPy-mediated changes in the viscoelastic properties of HA-UPy would translate to its lubrication function. To this end, the coefficient of friction ($\mu$) between healthy porcine cartilage explants was determined in the presence of HA-UPy and compared the measured values with those obtained when using corresponding HA solutions and saline (negative control) by using a rotational rheometer. The coefficient of friction (COF), $\mu$, was determined at the cartilage-to-cartilage interface, using the equation, $\mu$=(Shear stress)/(Normal stress). FIG. 12 shows that the COF between the contacting articular surfaces decreased significantly in the presence of HA-UPy. Specifically, the HA-UPy molecules reduced friction by ~70% and 55% compared to saline and HA molecules, respectively.

C. Self-Healing HA Promotes Free Radical Scavenging

Figure 13:
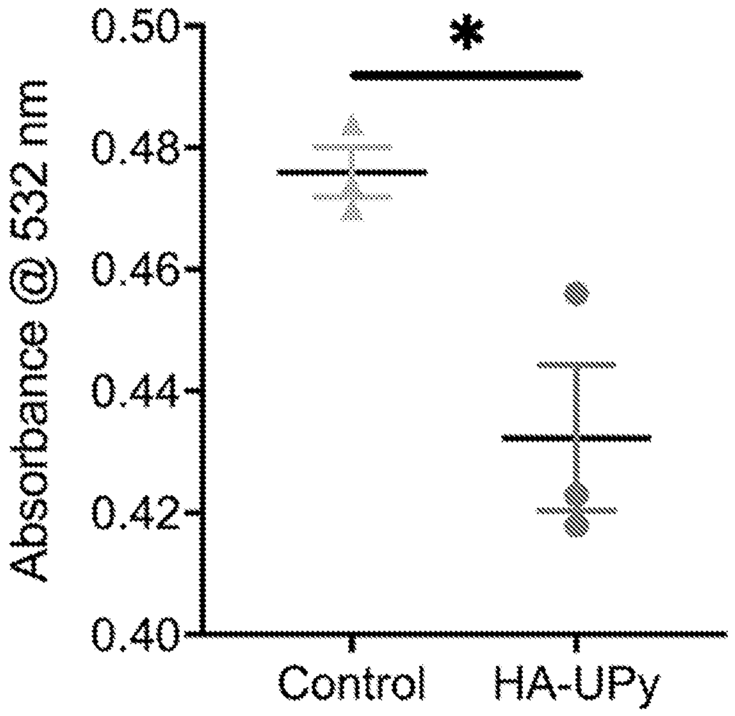
FIG. 13 shows free radical scavenging effect of HA-UPy exposed to Fenton reagent compared to the phosphate buffer control. Unpaired two-tailed t-test was used for statistical analysis. *P<0.05.
Figure 14:
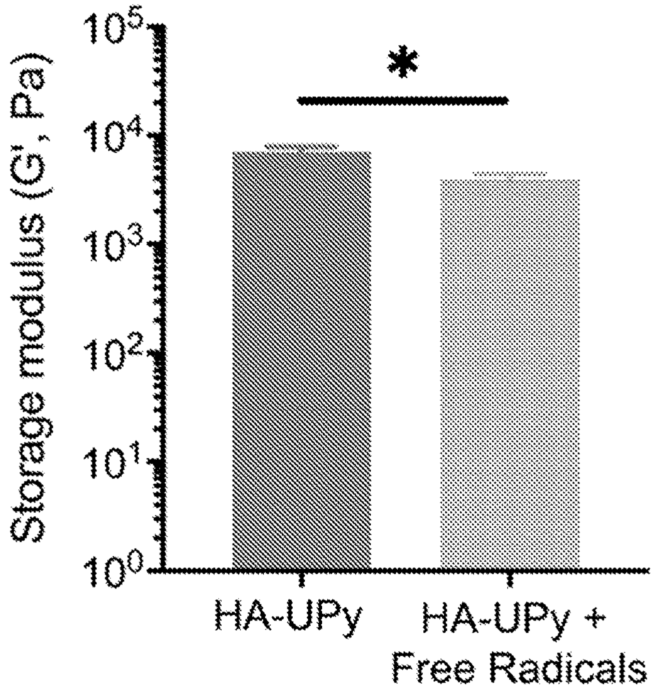
FIG. 14 shows storage modulus (G') of HA-UPy measured at a frequency of 1 Hz following exposure to hydroxyl radicals compared to non-exposed HA-UPy. Unpaired two-tailed t-test was used for statistical analysis. *P<0.05.
Figure 15:
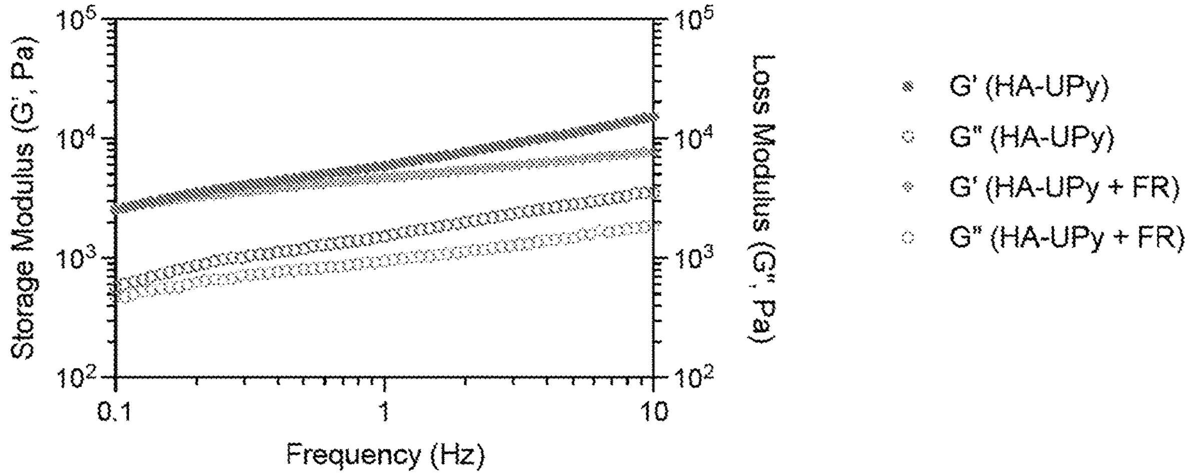
FIG. 15 shows data for storage (G') and loss (G") modulus of HA-UPy following exposure to hydroxyl radicals as a function of frequency. Minimal reduction in G' and G" are observed in the free radical-exposed HA-UPy (HAUPy+FR) compared to control HA-UPy.
Figure 16:
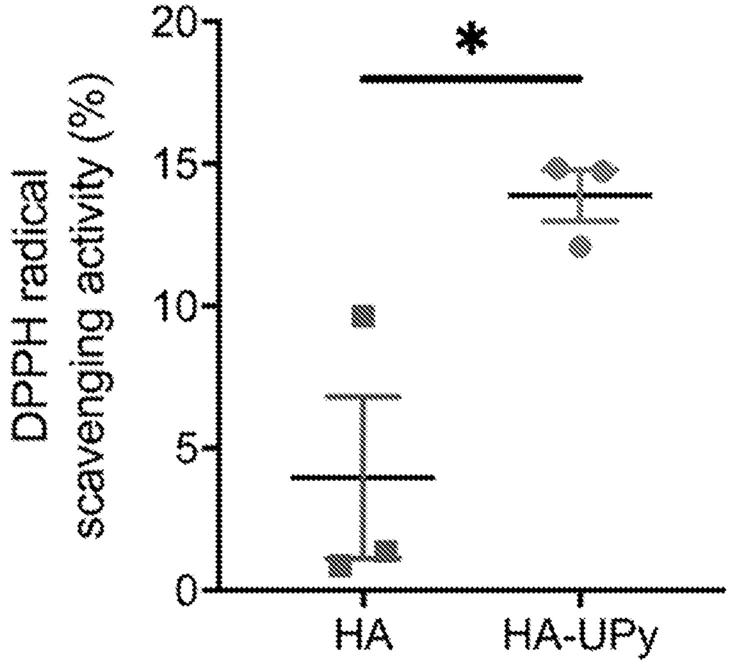
FIG. 16 shows DPPH radical scavenging of HA-UPy compared to HA. Unpaired two-tailed t-test was used for statistical analysis. *P<0.05.

HA has a number of biological functions, including serving as an antioxidant to reduce free radical damage to cells. The free radical scavenging effect of HA-UPy was investigated using deoxyribose/Fenton reagent and 1,1-diphenyl-2-picrylhydrazyl (DPPH) assays. In the deoxyribose/Fenton reagent assay, hydroxyl radicals are produced by the reaction of $Fe^{2+}$-EDTA with hydrogen peroxide. The hydroxyl radicals subsequently interact with deoxyribose and form a pink color chromogen with thiobarbituric acid upon heating. Following incubation with the Fenton reagent, the absorbance of the solution was measured. As seen in FIG. 13, the solution incubated with HA-UPy had a lower chromogen absorbance, corresponding to fewer hydroxyl radicals, suggesting free radical scavenging by HA-UPy molecules. Since free radicals cleave the glycosidic bonds in HA which could lead to the breakdown of polymer chains, the storage modulus of the HA-UPy exposed to the Fenton reagent was examined and compared to the storage modulus of untreated HA-UPy samples. FIG. 14 shows a slight reduction in the G' value, indicating some disruption of the network in the presence of free radicals (FIG. 15). Although the reaction was stopped after 1 h, ensuring the complete removal of free radicals from the solution is challenging. It is thus likely that free radicals continued to react with HA-UPy molecules. While the Fenton assay enables examination of the free radical scavenging effect of the HA-UPy in a physiologically relevant environment, a potential radical scavenging property of unmodified HA molecules cannot be determined because of the aqueous reaction environment. Hence, a DPPH assay was also used to examine the UPy-mediated changes in free radical scavenging, where the samples were exposed to a DPPH solution in ethanol. The solution containing HA-UPy molecules showed a significantly reduced DPPH free radical concentration as compared to that containing HA, which had a minimal scavenging effect (FIG. 16). The free radical scavenging ability of HA-UPy could be due to the network formation and/or the presence of UPy moieties. Prior studies have showed that the protective effect of HA against the free radical damage to the cells depends on HA molecular weight, with high molecular weight HA providing better protection. Furthermore, UPy moieties contain pyrimidine rings, which are known to scavenge free radicals. The minimal reduction in G' of HA-UPy following free radical exposure could be attributed to the UPy-mediated self-healing/self-generation of networks or by the UPy scavenging the free radical itself.

D. Self-Healing HA Molecules Showed Attenuated Enzymatic Degradation

Figure 17:
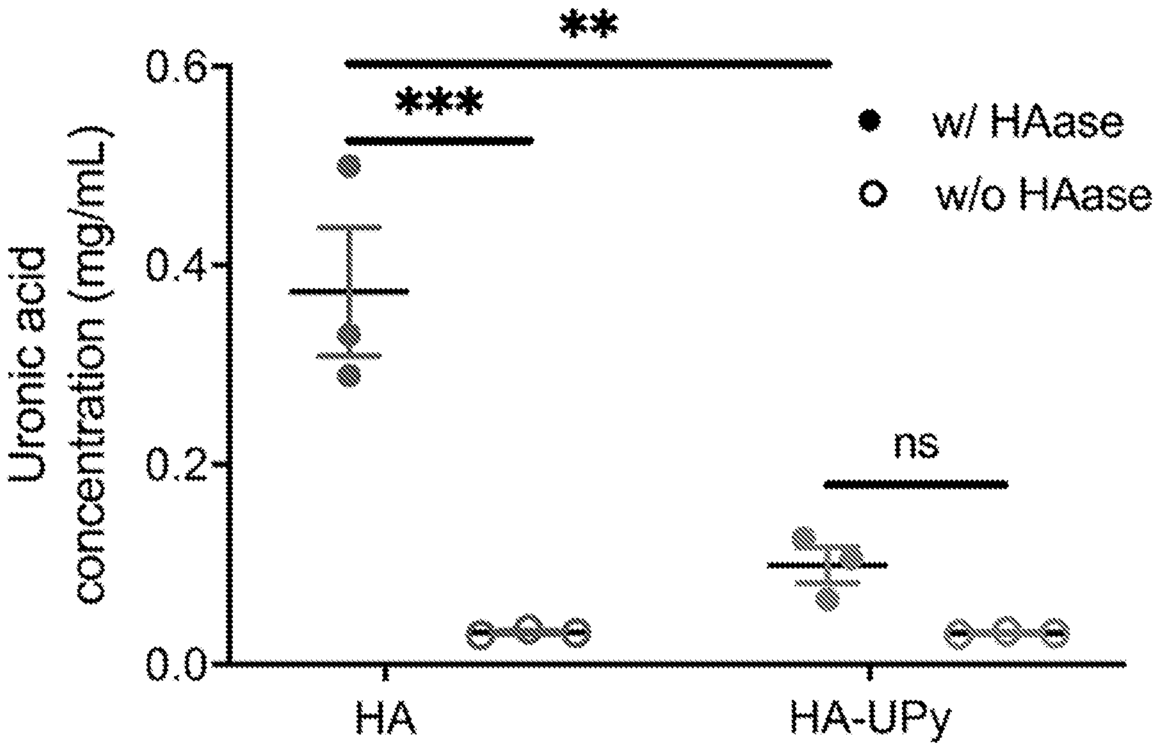
FIG. 17 shows degradation products of HA-UPy and HA with and without the presence of hyaluronidase (HAase). Two-way ANOVA with Tukey's multiple-comparisons test was used for statistical analysis. P<0.01, *P<0.001, and n.s. (not significant).

HA within the synovial fluid is subjected to enzymatic and free radical degradation, as well as lymphatic drainage, which are some of the key players contributing to its rapid clearance in the joint. The short residence time ($t_{1/2}$~24 h) of HA within the synovial joint has been thought to be one of the factors contributing to its limited clinical effectiveness following intraarticular injection, and chemically cross-linked HA derivatives have thus been generated to delay or slow the breakdown. The formation of supramolecular HA networks by UPy interactions may also slow the degradation of HA molecules. To test this, HA-UPy was incubated with hyaluronidase and quantified the resultant HA fragments by using a modified uronic acid assay. As demonstrated by the results, the HA-UPy experienced minimal degradation compared to the corresponding HA in the presence of hyaluronidase. Moreover, no statistical significance is observed between HA-UPy incubated with hyaluronidase and controls (i.e., HA and HA-UPy in the absence of hyaluronidase) (FIG. 17).

Figure 18:
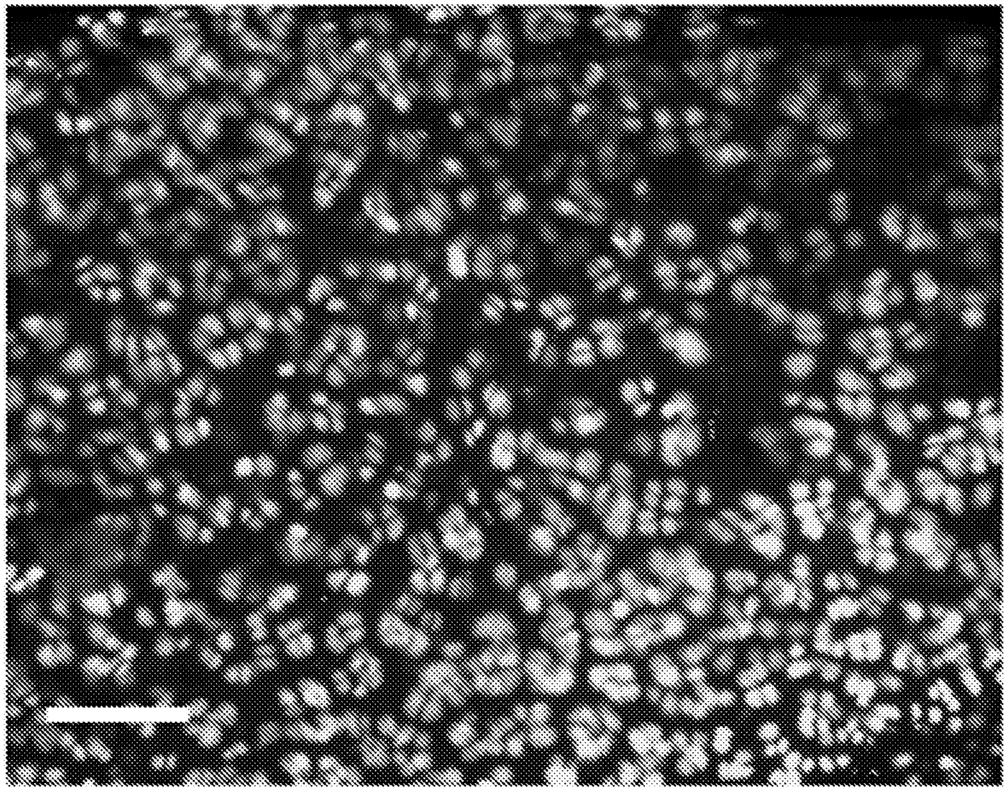
FIG. 18 shows chondrocyte viability in a rat cartilage explant after 7 d incubation with HA-UPy. Green: live cells; Red: dead cells. Scale bar: 100 μm.

Given the direct contact between HA-UPy and the cartilage surface, the cytocompatibility of HA-UPy was also evaluated by exposing rat cartilage explants to HA-UPy for a duration of 7 days. The live/dead analyses showed that nearly 100% of the chondrocytes were alive with no detrimental effect (FIG. 18).

Example 3

In Vivo Experiments Using 200 kDa HA-UPy

I. Materials and Methods

A. ACL injury models. All animal studies were approved by the Institutional Animal Care and Use Committee at Duke University in compliance with NIH guidelines for laboratory animal care. Both female mice (C57BL/6J, 3-month-old, Jackson Lab) and rats (Lewis, 3-month-old, Charles River) were used for unilateral anterior cruciate ligament transection (ACLT). Each animal was sedated using 2% isoflurane and injected with buprenorphine (1 mg/kg, sustained release, ZooPharm) as an analgesic prior to surgery.

For ACLT in mouse, each animal was placed in a supine position with the left hindlimb bent over a triangular cradle. After shaving and disinfecting the skin, a cut less than 0.5-cm-long was created from the medial side to expose the joint capsule. The ACL was fully extended by bending the knee to 90° C. and transected using spring scissors (FST, Cat. #15004-08). Bupivacaine (0.5%, Hospira) was then applied topically, and the incision was closed with Vicryl 5-0 sutures.

For mi-ACLT in rat, the left hindlimb was disinfected and flexed to approximately a 90° angle. An 18G needle was inserted perpendicularly into the joint on the lateral side of the patellar ligament, and the bevel of the needle was used to transect the ACL. To confirm the completion of ACLT, the clinical anterior drawer test was performed. In the anterior drawer test, the tibia easily moved out of the normal range of motion when pressure was applied behind the tibia while the femur was held in place. Following surgery, animals were placed on heating pads to aid in recovery from anesthesia and left unconstrained in cages.

B. Intra-articular injections. Sterile saline, HA (200 kDa, 10 wt % in saline), and HA-UPy (200 kDa, 10 wt % in saline) were prepared fresh and injected into the injured joints using a Hamilton syringe fitted with 26G needle. Animals were randomized to treatment groups following surgery. For mouse, injections were started one week following ACLT and performed weekly for four weeks with 5 μL of sample injected each time. For rat, injections were started one day following mi-ACLT and repeated weekly for another eight weeks with 50 μL of sample injected each time. One week after the last injection, animals were euthanized.

C. IVIS imaging. Calibration studies with varying extent of Cy7 modified HA molecules were carried out to identify optimal Cy7 concentration required to obtain the optical intensity. 50 μL of Cy7-containing HA or HA-UPy (10 wt %) was administered into the rat joint via intra-articular injection. At designated times after injection, rats were anesthetized under isoflurane inhalation and imaged by using an IVIS Kinetics system (excitation filter, 745 nm; emission filter, ICG; excitation time, 100 ms). The epi-fluorescence intensity of Cy7 in the joint was quantified by selecting an ROI from images taken at Day 0. The percent of initial fluorescence intensity was calculated after measuring the fluorescence intensity at each subsequent time point.

D. Histological analysis. Fixed joint samples were decalcified in 14% EDTA (pH 8.0, Sigma, Cat. #E5134) for 2-3 weeks at room temperature, rinsed with PBS, dehydrated, and embedded in paraffin blocks, and sliced into 8 μm-thick sections using a Leica rotary microtome. Each section was deparaffinized in CitriSolv (Decon Labs, Cat. #1601) and rehydrated through graded alcohols and deionized water. For Safranin-O staining, the rehydrated sections were incubated in hematoxylin solution (Ricca Chemical, Cat. #3536-16) for 1 min (for mouse) or 5 min (for rat), followed by 0.02% Fast Green (Sigma, Cat. #F7258) for 1 min (for mouse) or 1.5 min (for rat), and finally 1% Safranin-O (Sigma, Cat. #S8884) for 30 min (for mouse) or 1 h (for rat). The stained sections were rinsed, dehydrated, and covered with a mounting medium (Fisher Scientific, Cat. #SP15-100). Images were taken using a Keyence microscope.

E. OARSI scoring. Scoring of Safranin O-stained sagittal sections was performed by three blinded scorers in accordance with the OARSI histopathology initiative for evaluation of OA in mouse (Glasson et al. *Osteoarthritis Cartilage* 2010, 18 Suppl 3, S17) and rat (Gerwin et al. *Osteoarthritis and Cartilage* 2010, 18, S24). Scoring criteria for the mouse included the degree of degeneration of cartilage in both the tibia and femur, evaluated from 0-6: 0 means normal; 0.5 has loss of proteoglycan without structural changes; 1 shows limited fibrillation on the cartilage surface; 2 presents vertical clefts; 3 means vertical clefts or erosion covering <25% of surface area; 4 for 25-50% area being affected; 5 for 50-75%; and 6 for >75%. Scoring criteria for the rat included total tibial cartilage degeneration (0-5 for 3 zones, total 0-15), femoral cartilage degeneration (0-5), bone score (0-5), and osteophyte score (0-4), with total added score from 0-29. The osteophyte score was modified for sagittal joint sections based upon a histogram of osteophyte sizes for all samples in the mi-ACLT groups. ImageJ was used to quantify total cartilage degeneration, significant cartilage degeneration, and surface matrix loss (all expressed as the percentage of total cartilage width), as well as depth ratio of cartilage lesions (expressed as the depth of degenerated cartilage to the thickness of total cartilage). These measurements were completed for both the tibia and femur, the latter of which is a modification of the original scoring which only examines the tibia. A total of four sections, taken from two locations within the medial compartment of the joint, were evaluated. These four scores/measurements were averaged as technical replicates for each subject.

F. Immunohistochemical analysis. Immunohistochemical staining was used to detect MMP-13 and ADAMTS-5 expression in cartilage. Briefly, deparaffinized sections were subjected to heat-induced antigen retrieval in a vegetable steamer for 13 min and permeabilized with 0.1% Triton X-100 for 15 min. Tissue sections were blocked with 0.1% BSA and 0.26 M glycerol in TBS for 1 h, sequentially exposed to Dual Endogenous Enzyme Block (Dako, Cat. #S2003) for 30 min, and 5% and 1.5% normal goat serum for 30 min and 1 h, respectively, before incubation at 4° C. overnight with either anti-MMP13 (dilution 1:500, Abcam, Cat. #ab39012) or anti-ADAMTS5 (dilution 1:100, Abcam, Cat. #ab41037). VECTASTAIN® Elite ABC HRP Kit (Vector Laboratories, Cat. #PK-6100) kit and ImmPACT® DAB Peroxidase Substrate (Vector Laboratories, Cat. #SK-4105) were used to visualize the enzyme expression.

G. Statistical analysis. The means with standard error of mean (n≥3) are presented in the results. All animal studies included at least 6 animals per group. All the data were subjected to two-tailed Student's t-test, one-way analysis of variance (ANOVA) with post-hoc Tukey's multiple comparisons test, or two-way repeated measures ANOVA with Tukey's multiple comparisons test using GraphPad Prism 8. Specific statistical analyses performed for each data set are detailed in the figure captions. Any p-value of less than 0.05 was indicated with an asterisk and was considered statistically significant. All experiments were reproduced independently.

II. Results and Discussion

Figure 19A:
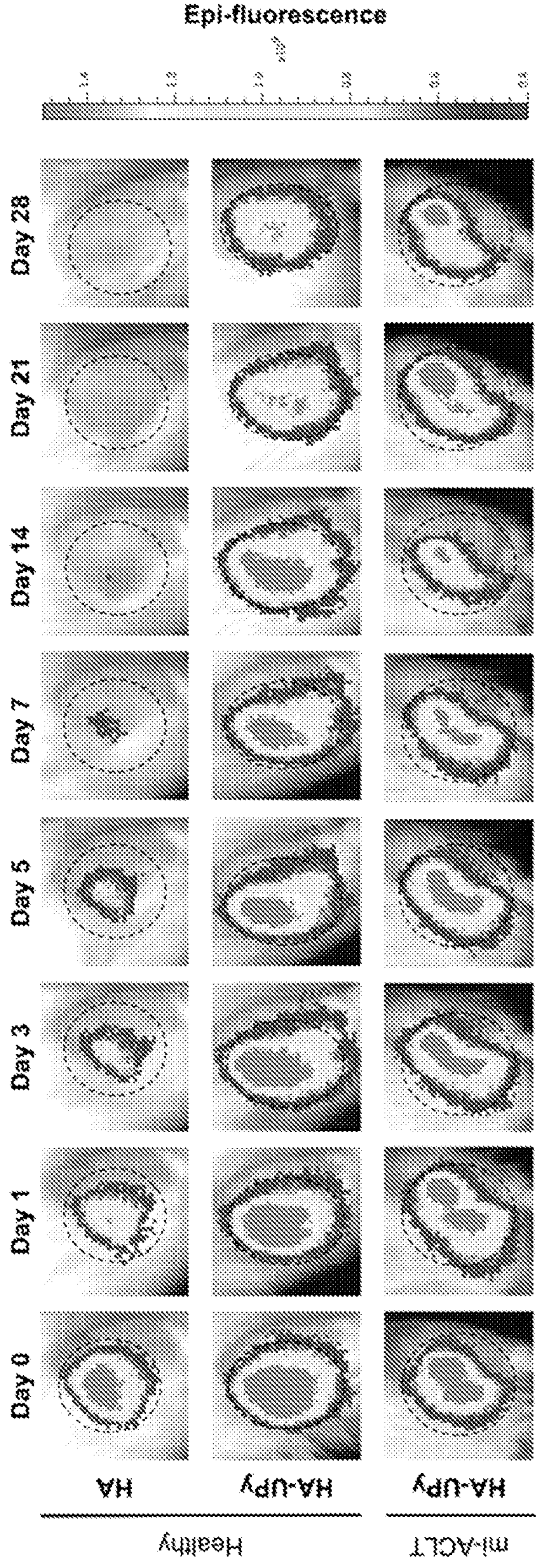
FIGS. 19A-19B data demonstrating in vivo retention of self-healing HA.
Figure 19B:
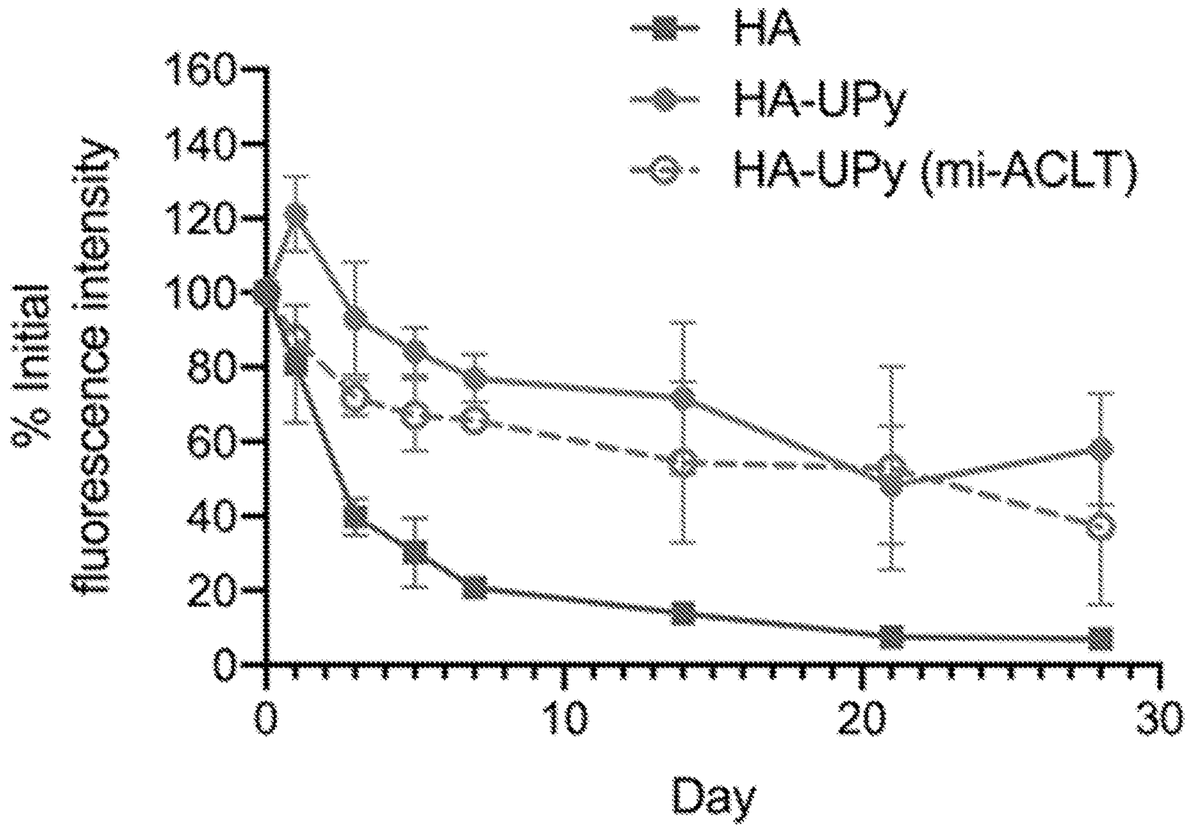

A. Self-healing functionality improved the in vivo retention of HA. The in vivo retention of HA-UPy following intraarticular injection was studied as a function of time by live imaging of rat knees and compared against corresponding HA. Cy7-conjugated HA-UPy and HA molecules were injected into rat knees and monitored using IVIS for 28 days. Calibration studies were performed to ensure that both cohorts received similar levels of Cy7 molecules. The animals were imaged immediately and 24 h post-injection for the initial reading, which showed clear positive signals from the joints administered with HA-UPy and HA. Longitudinal imaging indicated that a majority (>60%) of the HA was cleared from the joint by ~3 days (FIGS. 19A-19B). In contrast, strong positive signals were present in the HA-UPy group even at 28 days, the maximum experimental time point, with a ~40% reduction in fluorescence intensity compared to the initial reading (i.e., immediately after administration) (FIG. 19B). The values are presented as a percentage of initial fluorescence intensity to account for variability among the animals.

The effect of injury on lubricant clearance was examined by comparing the retention of HA-UPy in rat joints which underwent minimally invasive anterior cruciate ligament transection (miACLT), where the HA-UPy was administered two days post-mi-ACLT. Similar to the healthy group, a significant amount of the administered HA-UPy was retained within the mi-ACLT joints, albeit less than that in the uninjured joints. Given that a molecular weight of 200 kDa is well below the permeability barrier of the synovial membrane, the increased residence time of HA-UPy within the joint synovial space is attributed to self-healing of HA molecules.

Figure 20A:
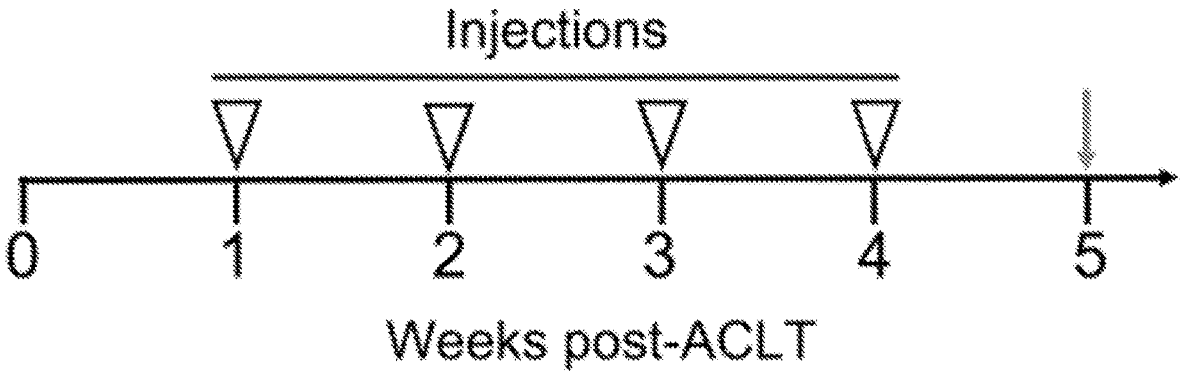
FIGS. 20A-20C show data demonstrating chondroprotection of HA-UPy in a mouse surgical ACLT model.
Figure 20B:
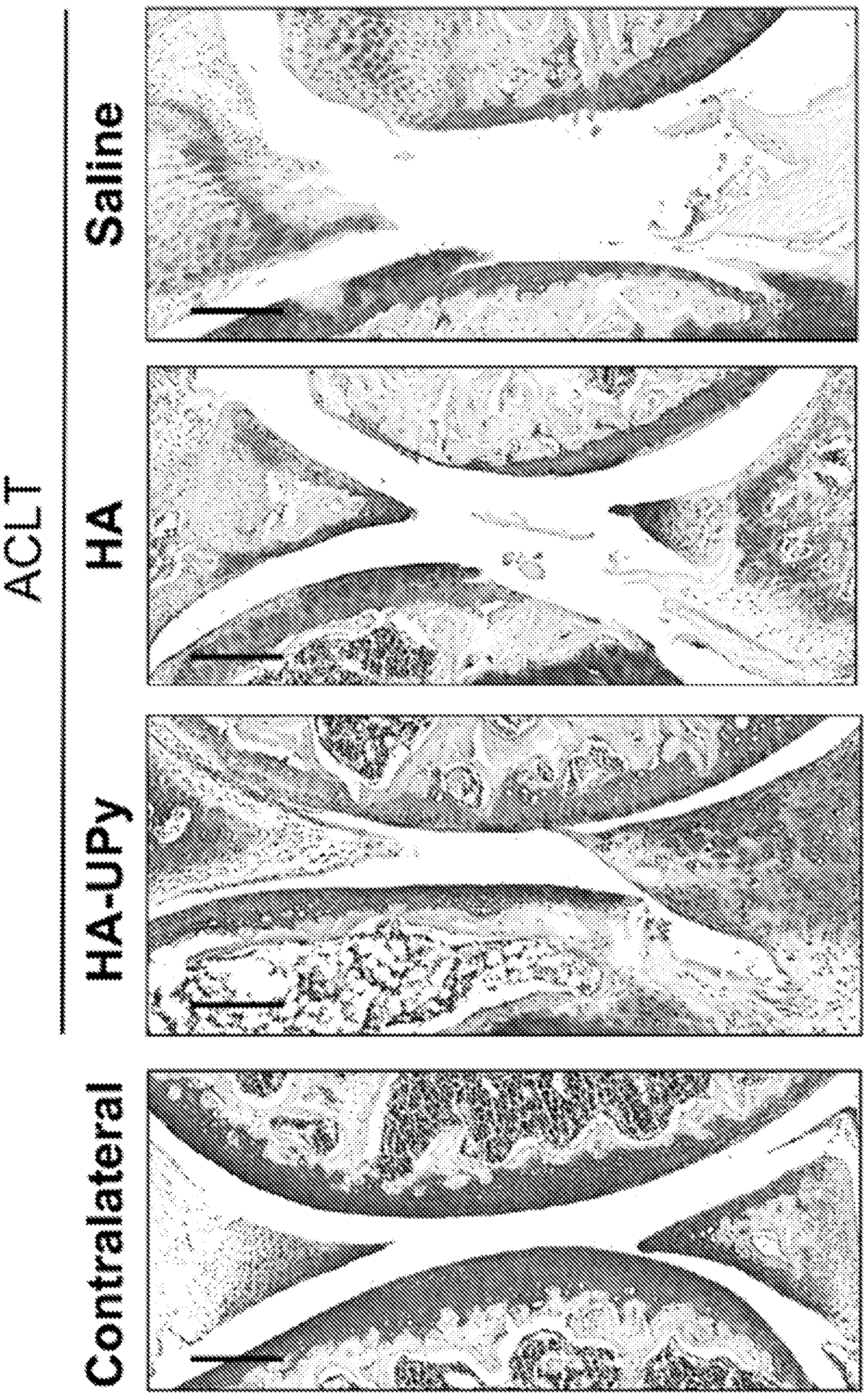
Figure 20C:
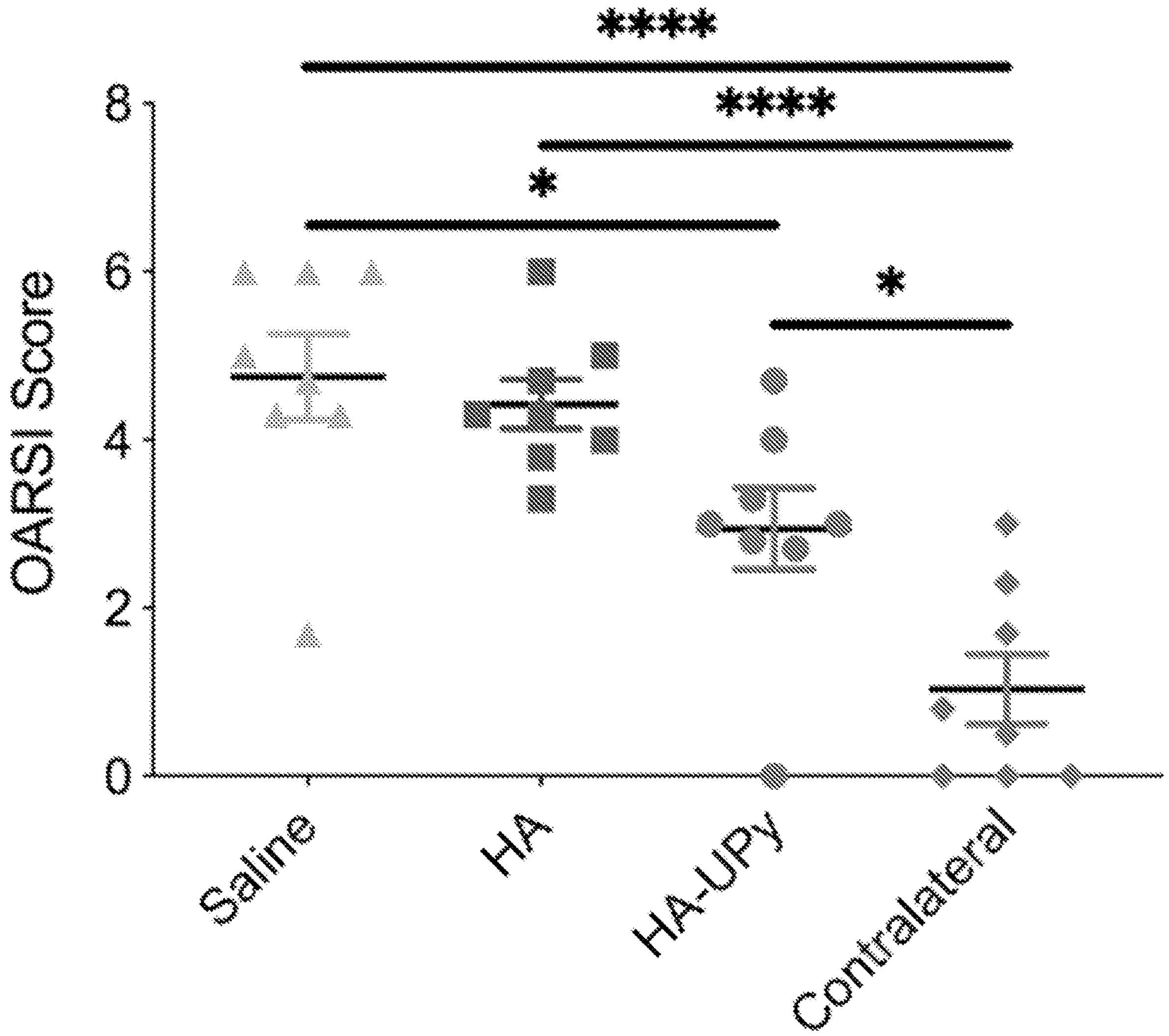

B. Self-healing HA provides improved chondroprotection. The enhanced lubrication along with its improved retention in the joint suggests that the self-healing HA-UPy could offer chondroprotection following joint injury. To assess the in vivo chondroprotective function, we have used mouse and rat ACL transection models. The surgical ACL transection model is widely used to represent articular cartilage degeneration consistent with ACL injuries, which cause joint instability, chronic inflammation, and degeneration. The ACL-transected mice received weekly intraarticular injections of HA-UPy, HA, or saline for four weeks beginning one week post-surgery as shown in the experimental timeline (FIG. 20A). Weekly injections were chosen based on prior reports and in vivo imaging which showed complete clearance of HA by day 7. Safranin O staining of the knee joints at week 5 showed significant damage to the articular surfaces of the cohorts that received saline (FIG. 20B). Similar to the saline group, the animals that received HA injections showed significant cartilage degeneration. In contrast, the cohort that received HA-UPy maintained better cartilage integrity with significant positive staining for glycosaminoglycans. We used a semi-quantitative score of cartilage degeneration (OARSI) to assess the matrix loss, surface fibrillation, and erosion of the cartilage, which corroborated the histological findings (FIGS. 20B-20C). The lower scoring value for the animals that received HA-UPy suggests improved chondroprotective function of the parent HA following modification (i.e., HA-UPy).

Figure 21A:
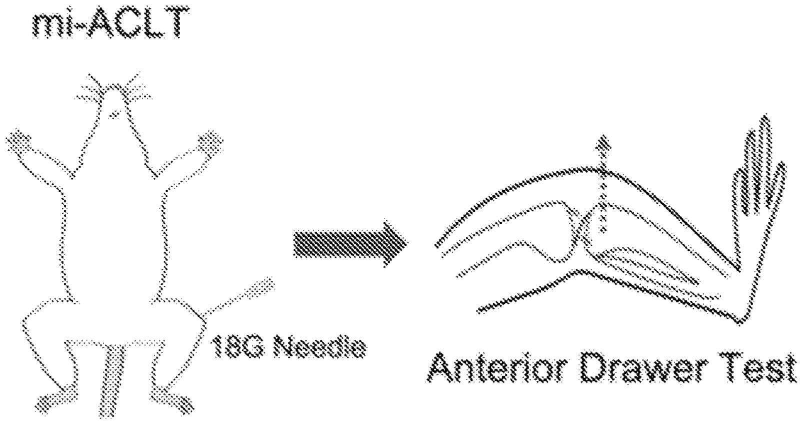
FIGS. 21A-21I show data from a minimally invasive ACLT (mi-ACLT).
Figure 21B:
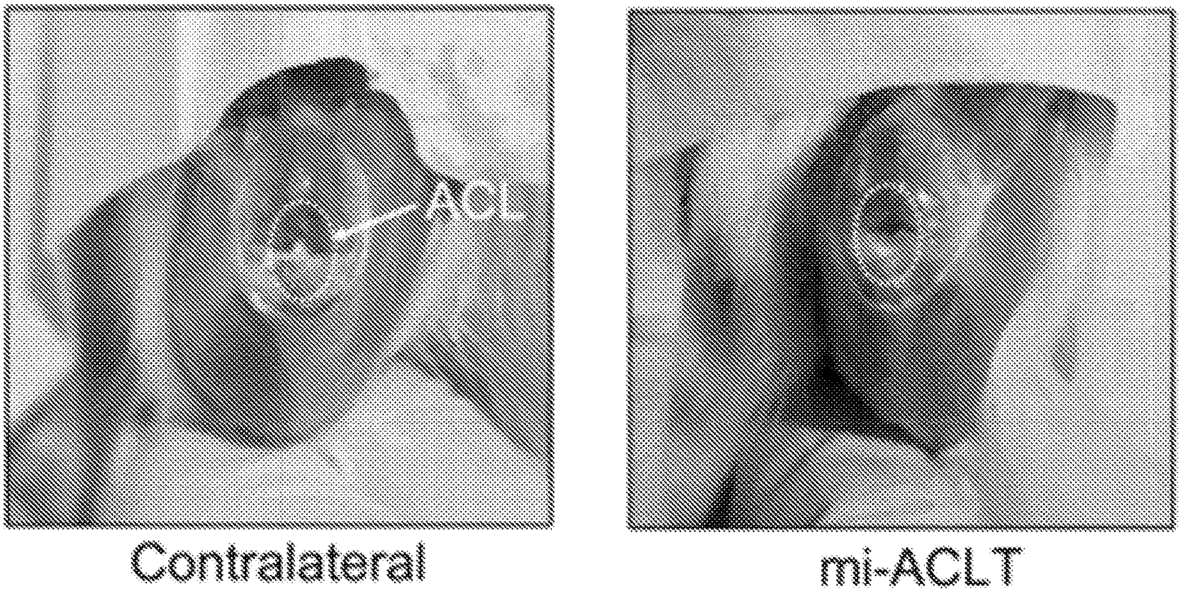
Figure 21C:
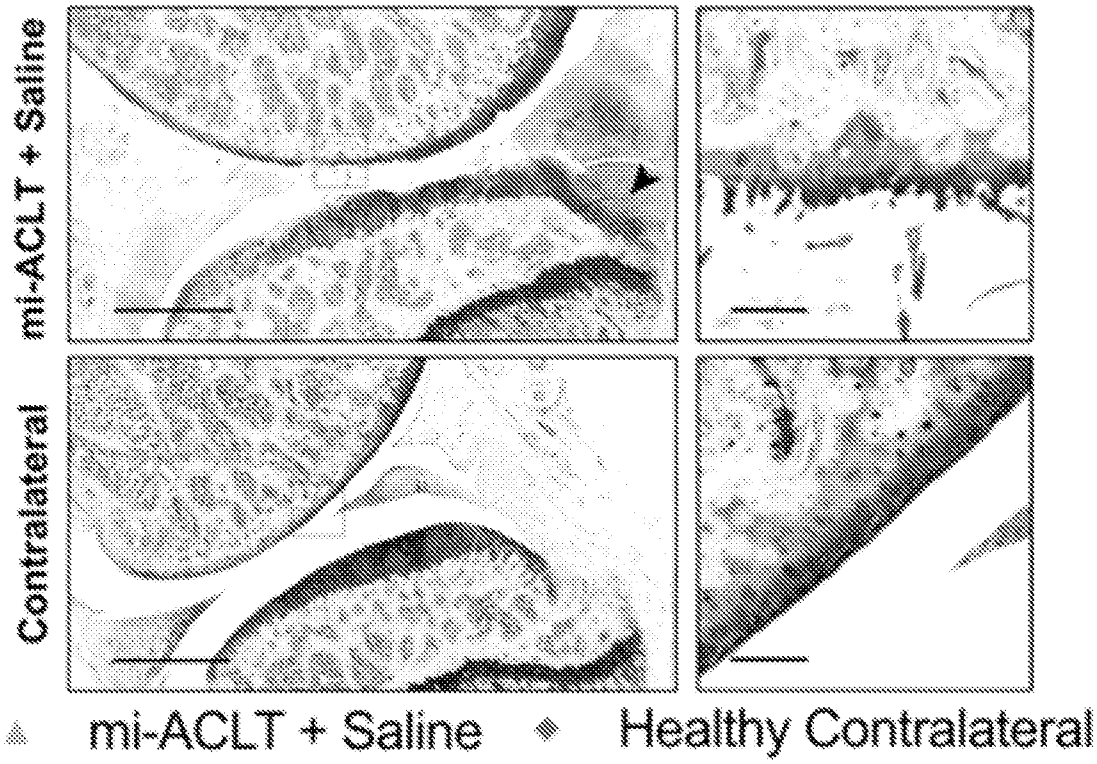
Figure 21D:
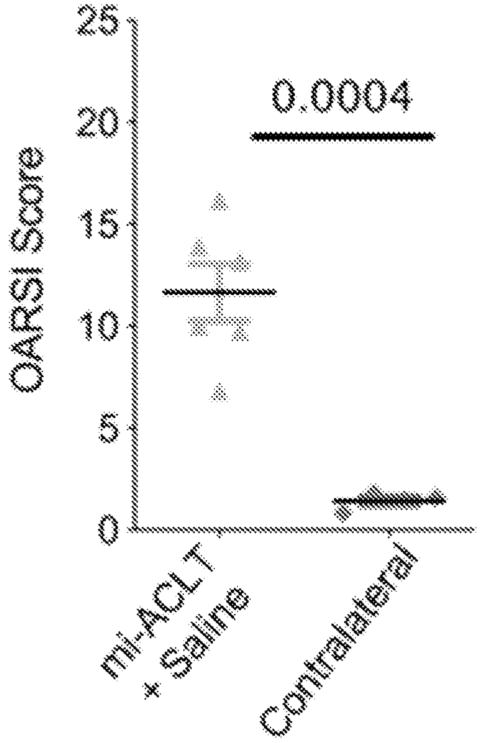

Because mouse joints only permit intraarticular injections of small volumes (~5 μL), a rat knee injury model was employed to determine the chondroprotection of self-healing HA-UPy. By using a minimally invasive, percutaneous procedure, an ACL injury (mi-ACLT) was developed in the rat knee without surgically opening the joint. Specifically, the ACL was transected with an 18G needle which was inserted into the knee joint lateral to the patellar tendon while the knee was flexed at a ~90° angle (FIG. 21A). Successful ACL rupture was confirmed by using the anterior drawer test, which exhibited abnormal subluxation of the tibia. The dissected knee joints post-mortem showed that the ACL had been successfully transected (FIG. 21B). The mi-ACLT-mediated cartilage degeneration was assessed at week 9 following weekly saline injections over eight weeks. Safranin 0/Fast Green staining of sagittal sections of the articular joints showed severe fibrillation and erosion of both the tibial and femoral cartilage (FIG. 21C). The formation of osteophytes was also visible on the posterior region of the tibia. In contrast, the cartilage surfaces of the uninjured contralateral limbs were smooth with no significant degeneration, and no osteophytes were present. The degree of degeneration was quantified using the rat OARSI score (Gerwin et al. *Osteoarthritis and Cartilage* 2010, 18, S24), which showed that the mi-ACLT group had a significantly higher score than that of the unoperated control, consistent with greater cartilage degeneration (FIG. 21D).

Figure 21E:
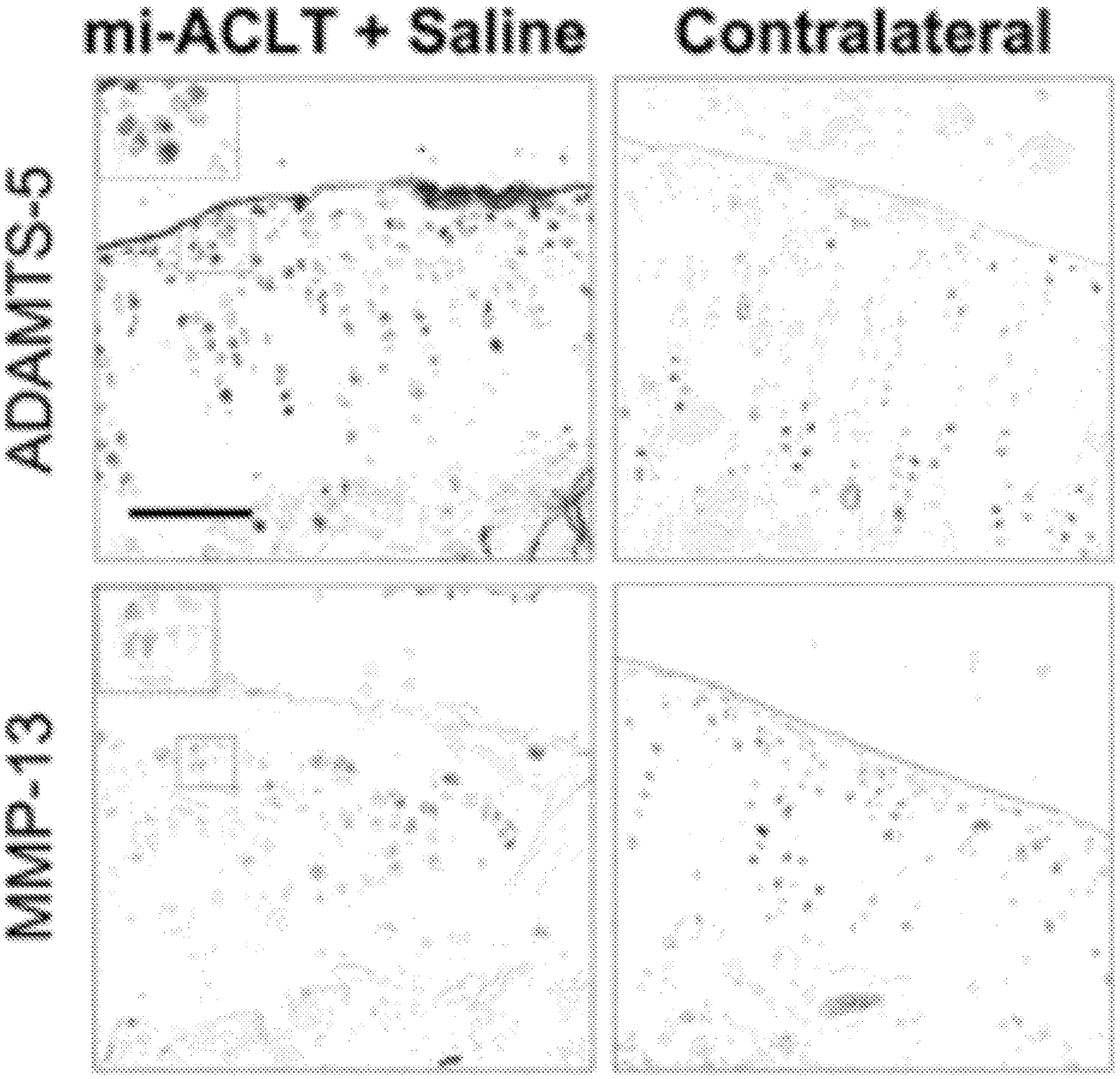
Figure 21F:
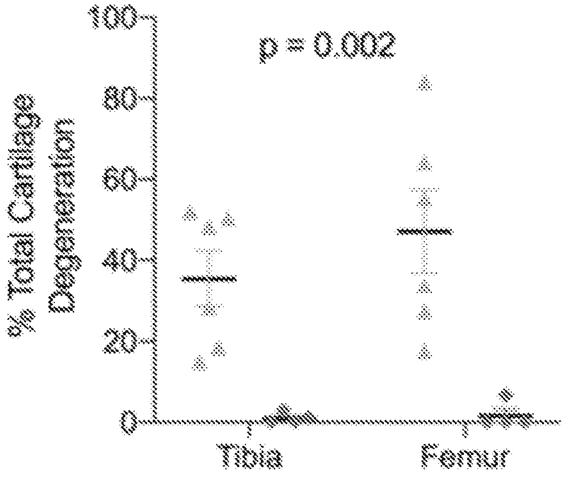
Figure 21G:
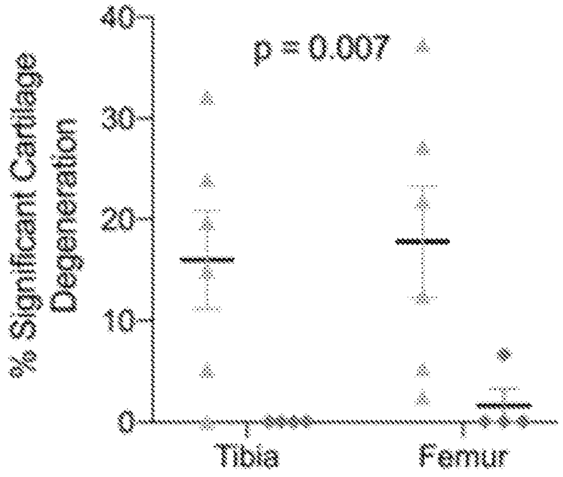
Figure 21H:
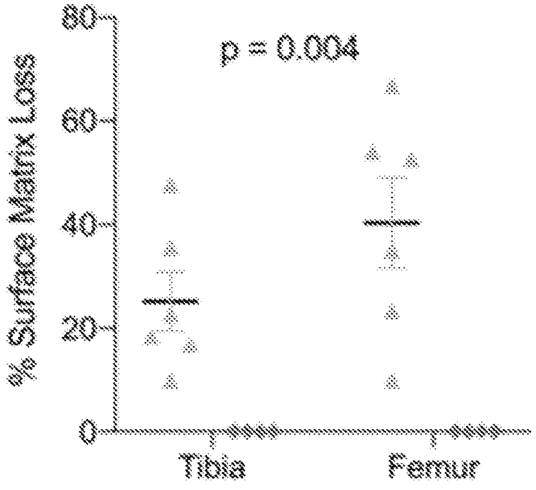
Figure 21I:
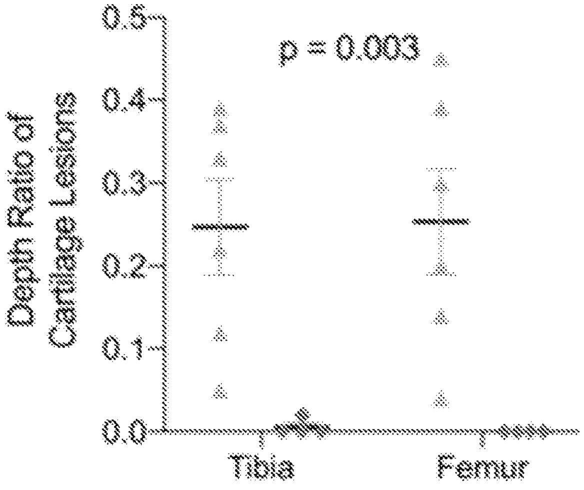

The extent of cartilage degeneration was further examined by immunohistochemical (IHC) staining for catabolic markers—matrix metalloproteinase-13 (MMP-13) and a disintegrin and metalloproteinase with thrombospondin motifs 5 (ADAMTS-5), which are shown to be highly active during cartilage degeneration. Cartilage in the mi-ACLT group showed a higher expression of both ADAMTS-5 and MMP-13 than the contralateral group, indicating greater degeneration (FIG. 21E). Furthermore, clustering of the chondrocytes, a hallmark of osteoarthritic cartilage, was clearly present in the mi-ACLT group but not in the healthy contralateral group. In addition to the semi-quantitative scoring (OARSI score), total cartilage degeneration (matrix, proteoglycan, or chondrocyte loss), significant cartilage degeneration (degeneration >50% of cartilage thickness), surface matrix loss (matrix fibrillation), and the depth ratio of cartilage lesions (ratio of depth of cartilage degeneration to total cartilage thickness, measured at three zones) were quantified as described elsewhere (Gerwin et al. *Osteoarthritis and Cartilage* 2010, 18, S24). In addition to the tibia (which is commonly the focus for rat OARSI scoring), the femur was also analyzed, as recent studies have shown that the medial femoral condyle exhibits severe degeneration with ACL injury, both in animals and humans. The mi-ACLT procedure was shown to significantly increase total cartilage degeneration (FIG. 21F), significant cartilage degeneration (FIG. 21G), surface matrix loss (FIG. 21H), and depth ratio of cartilage lesions (FIG. 21I) as compared to the healthy contralateral group. Together, the data demonstrate significant cartilage degeneration following mi-ACLT.

Figure 22A:
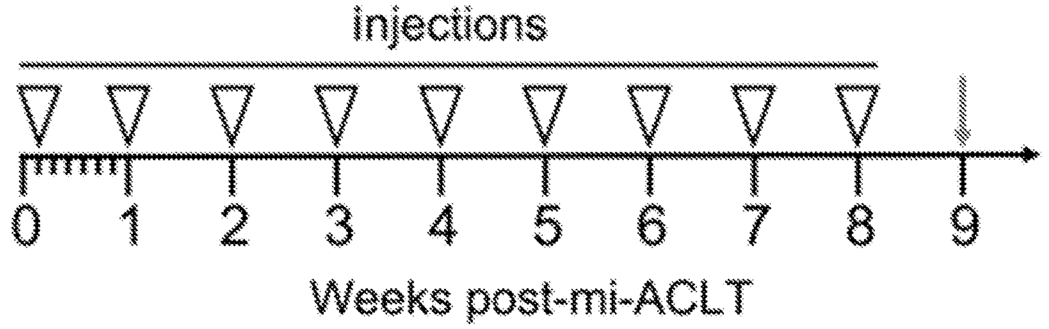
FIGS. 22A-22H show data demonstrating chondroprotection of self-healing HA in a minimally invasive rate ACLT model.
Figure 22B:
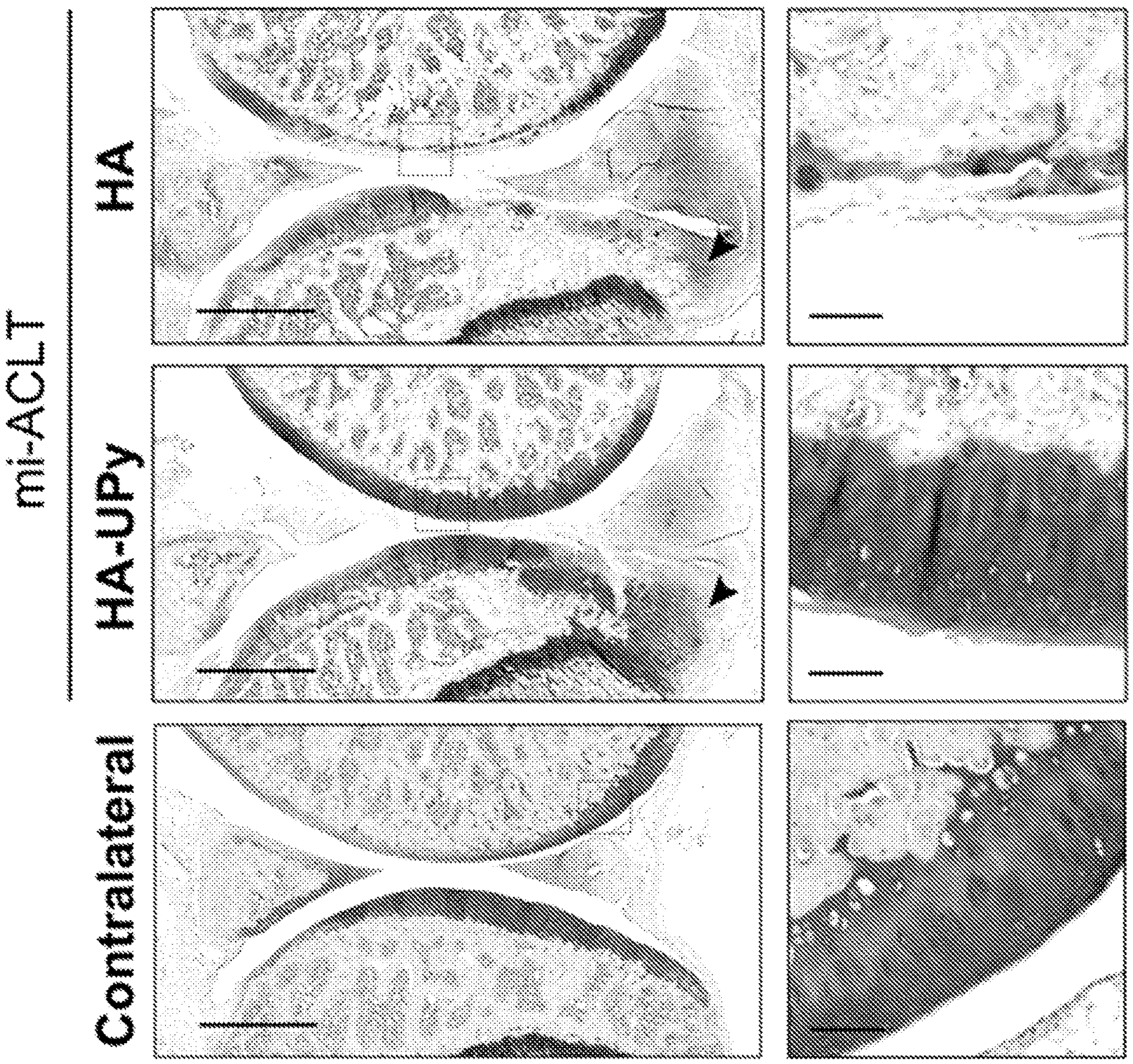
Figure 22C:
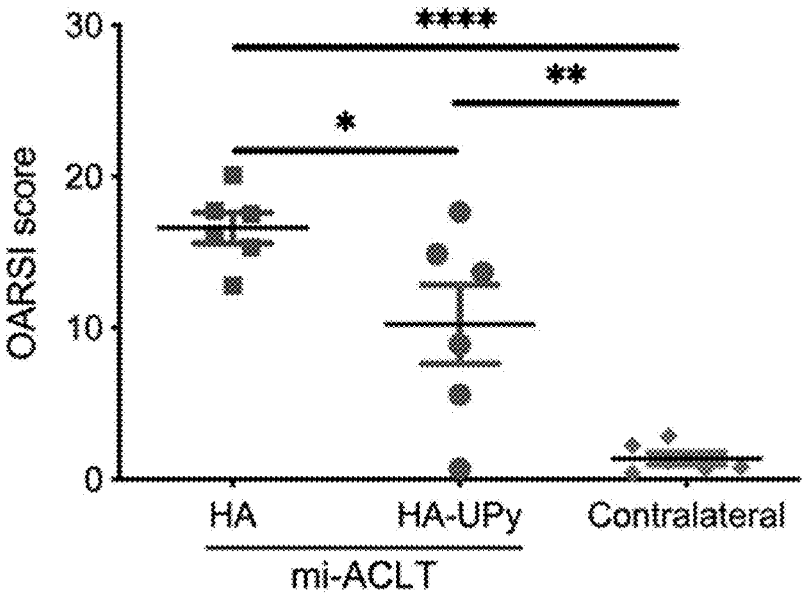

The chondroprotective function of self-healing HA in the rat mi-ACLT model was also examined. Because the HA- and saline-treated animals exhibited similar cartilage degeneration, the HA-UPy-treated rat joints were compared to those treated with corresponding HA. As described in FIG. 22A, the animals received weekly injections starting one day post-mi-ACLT for a total of eight weeks. At week 9, animals were euthanized, and their joints were examined histologically. The cohorts treated with HA showed significant cartilage degeneration compared to those treated with HA-UPy. Specifically, cartilage erosion, proteoglycan loss, and osteophytes in the tibia were clearly observed in the HA group and were similar to features observed in the saline group (FIG. 22B). On the contrary, joints treated with HA-UPy showed higher Safranin O staining intensity with minimal cartilage thinning but displayed some degree of cartilage fibrillation and osteophyte formation. In comparing the OARSI scores, HA-UPy, while higher than the contralateral group, had a significantly lower score than the corresponding HA group (FIG. 22C).

Figure 22D:
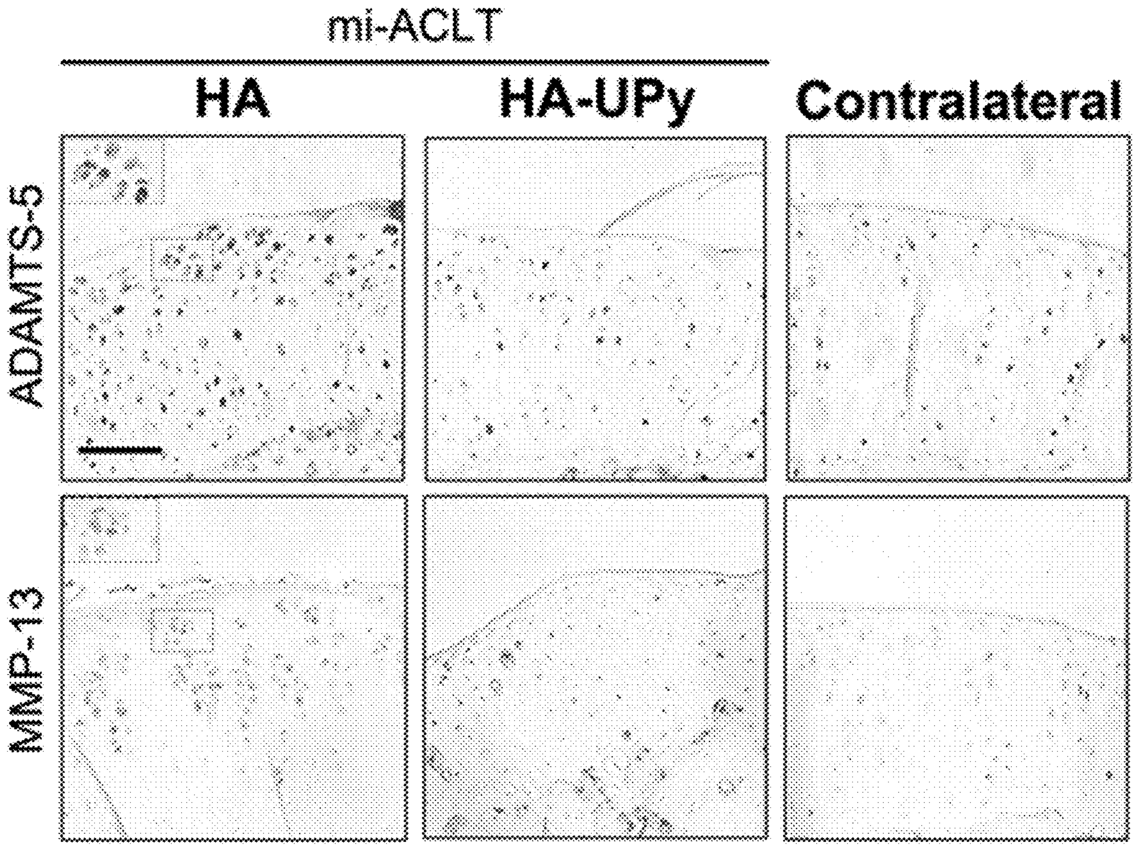
Figure 22E:
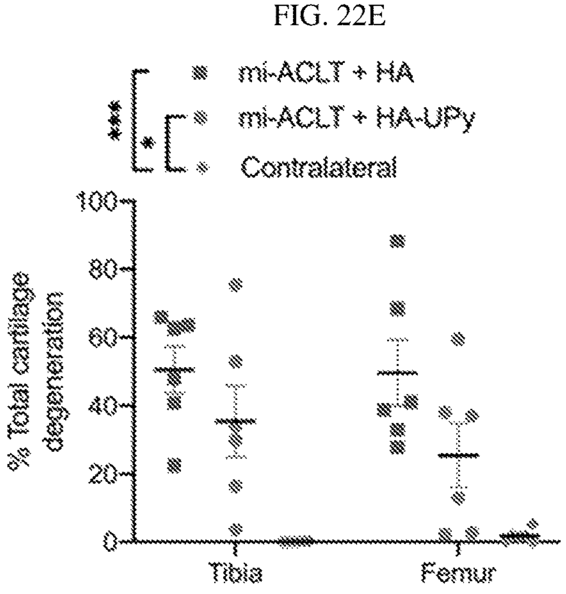
Figure 22F:
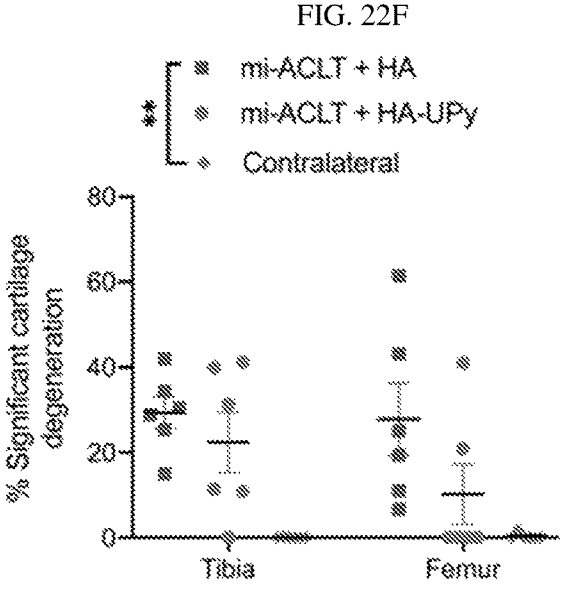
Figure 22G:
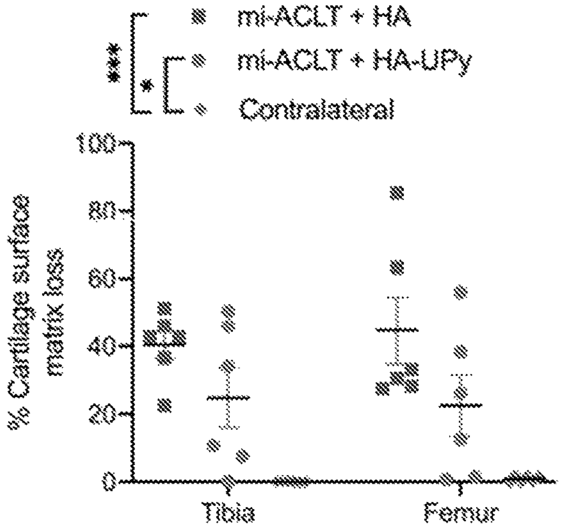
Figure 22H:
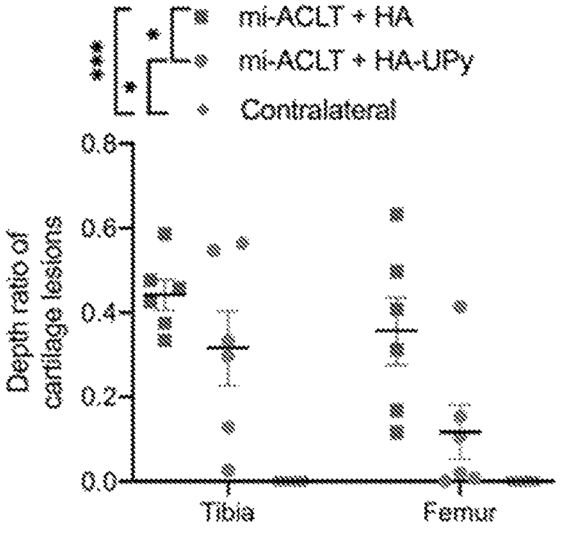

Furthermore, MMP-13 and ADAMTS-5 IHC staining showed higher expression of these catabolic enzymes in the HA group, as seen by greater staining (both in intensity and the number of stained cells), compared to the HA-UPy and contralateral groups (FIG. 22D). Furthermore, the joints treated with HA showed evidence of chondrocyte clustering, similar to those treated with saline. A majority of the HA-UPy-treated joints showed minimal cartilage degeneration, and no chondrocyte clustering was observed in these animals similar to the unoperated contralateral groups. Moreover, the organization and distribution of chondrocytes within the cartilage of cohorts treated with the HA-UPy molecules was found to be similar to that of the uninjured contralateral groups. We also quantitively assessed the total cartilage degeneration, significant cartilage degeneration, surface matrix loss, and the depth ratio of cartilage lesions. These parameters were lower in the HA-UPy group than the HA group for both the femur and tibia (FIG. 22E-22H). Despite the high variability among the treated animals, the total tibial degeneration was ~30% less in animals treated with HA-UPy compared to those treated with HA (as a percentage of total cartilage width: 35±10% for HA-UPy vs. 51±7% for HA). Similarly, joints treated with HA-UPy displayed half as much total cartilage degeneration in the femur (as a percentage of total cartilage width: 25±9% for HA-UPy vs. 50±10% for HA) compared to those treated with HA. The HA-UPy group also showed a reduced amount of significant cartilage degeneration, which consists of the width of cartilage in which 50% or more of the cartilage thickness is degenerated. The cartilage lesions in the HA-UPy group also spanned significantly less of the cartilage thickness as compared to those in the HA group, indicating that self-healing HA was more chondroprotective than unmodified HA. The high variability observed in the HA-UPy-treated group could be attributed to the presence of minimally modified or unmodified HA molecules. It is also likely that the high variability is due to differences in the initial cartilage damage that may result from the needle during the mi-ACLT procedure. Because the injury is performed on a closed knee, there is risk of unintentionally damaging the cartilage or other joint tissues, increasing the severity of the injury. While the potential for this variability is high, we have randomized the animals to each treatment to ensure that differences due to the mi-ACLT procedure are spread amongst groups.

Example 4

Synthesis and Characterization of 1M Da HA-UPy

Figure 23A:
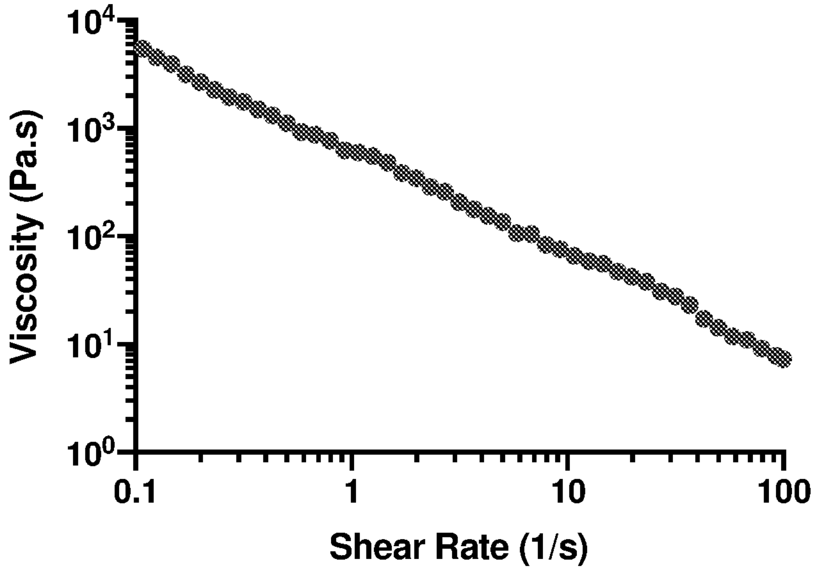
FIGS. 23A-23C show: viscosity changes of 1M Da HA-UPy as a function of shear rate (FIG. 23A); data from frequency sweep measurements for 1M Da HA-UPy, showing the evolution of storage (G') and loss (G") moduli as a function of frequency (FIG. 23B); and data from step-strain measurements of 1M Da HA-UPy (FIG. 23C).
Figure 23B:
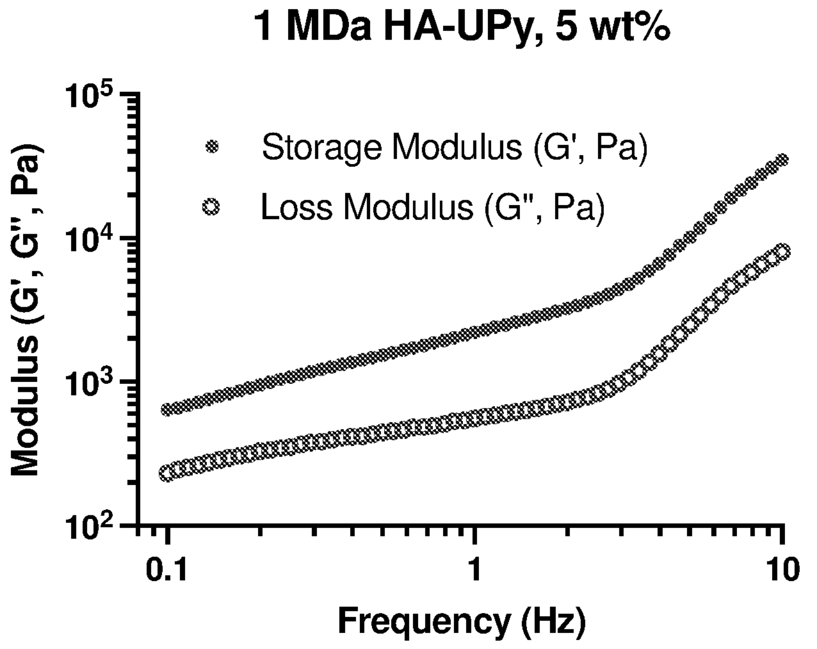
Figure 23C:
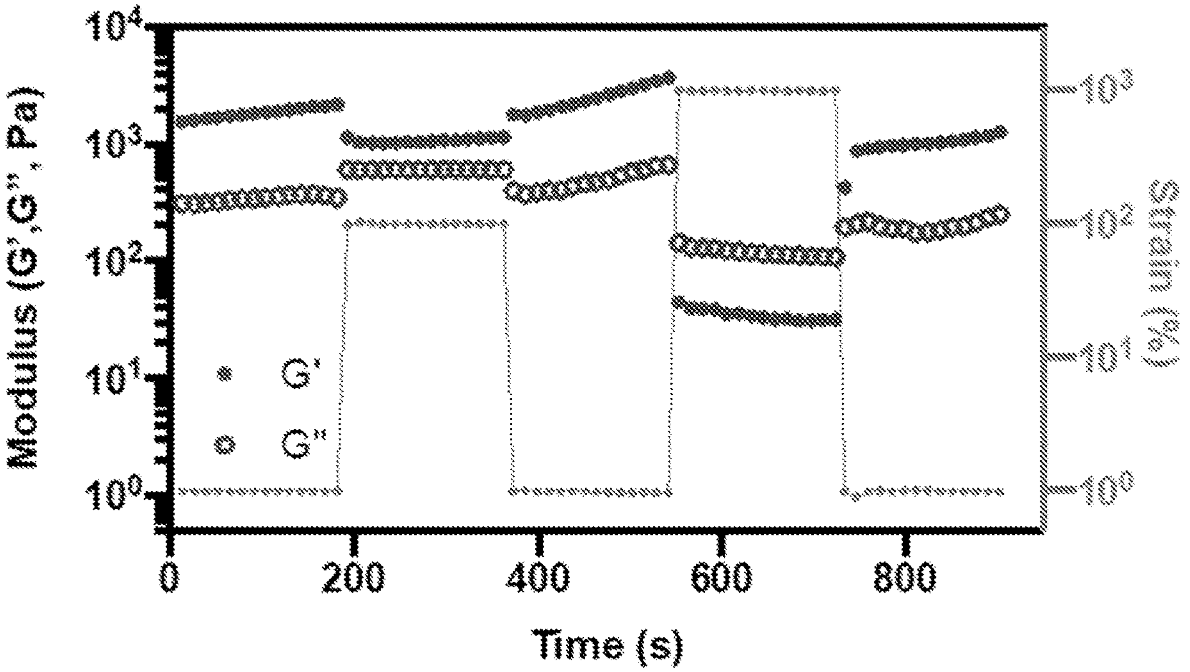
Figure 24:
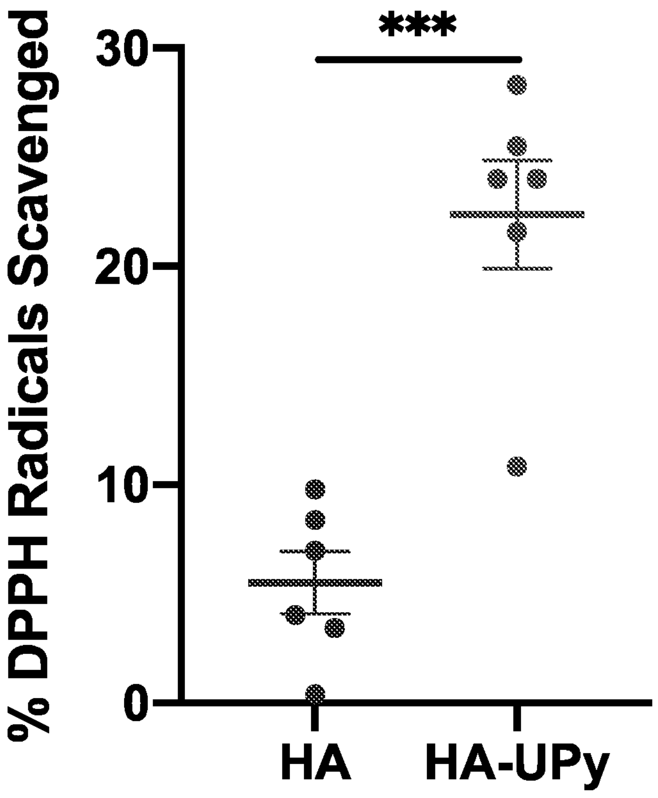
FIG. 24 shows free radical scavenging of 1M HA-UPy compared to HA. ***P<0.001. The measurements were carried out by a DPPH assay.

A 1M Da (1000 kDa) HA-UPy compound was prepared in an analogous manner to the 200 kDa HA-UPy compound described in Example 1, using a starting sodium hyaluronate compound having a molecular weight of 1000 kDa. The product was characterized by similar methods. The rheological characterization of the resultant HA-UPy molecules showed that they exhibited a shear thinning behavior (FIG. 23A). The frequency sweep measurements of HA-UPy samples exhibited higher G' (storage modulus) at all frequencies suggesting network formation (FIG. 23B). Step-strain measurements suggested healing of the polymer chains and the formation of dynamic networks (FIG. 23C). The step-strain measurements involved exposing the molecules to a constant strain in a stepwise manner over a period of 900 s at an interval of 180 s. A decrease in storage modulus indicates that the applied force is sufficient in overcoming the interactions between the polymer chains. Once the high strain is removed, the HA-UPy exhibited recovery of its storage/loss moduli. FIG. 24 shows the free-radical scavenging ability of HA-UPy molecules, which was measured by using a DPPH assay as discussed above.

Figure 25:
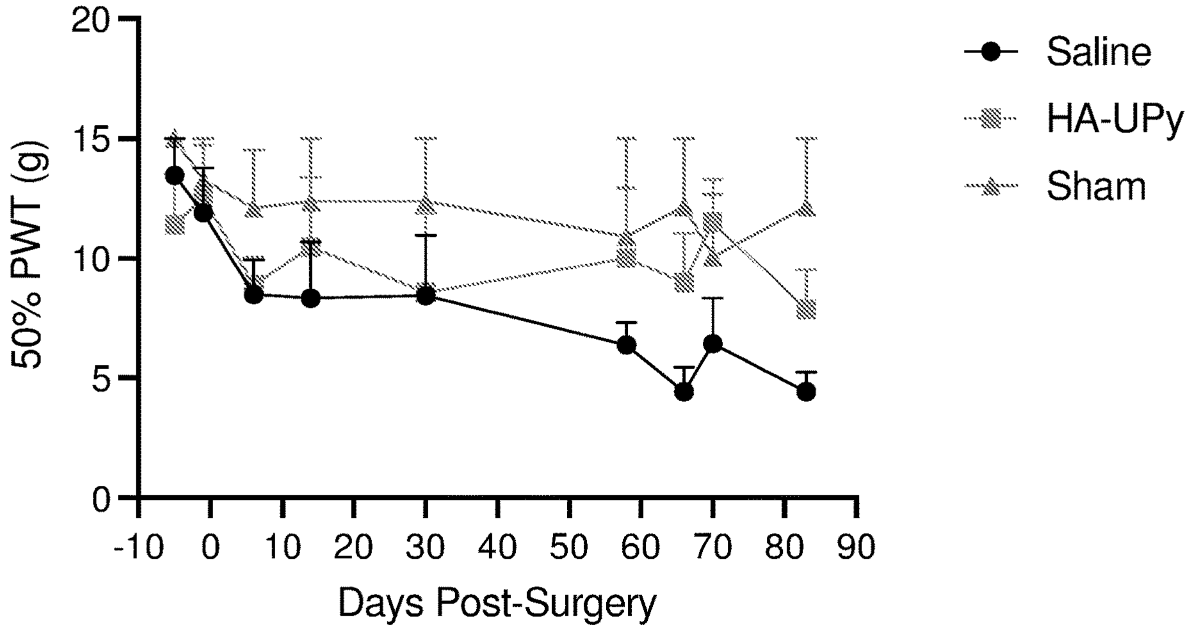
FIG. 25 shows data from a Von Frey test for 1M Da HA-UPy, which measures pain, as described in Example 4.
Figure 26:
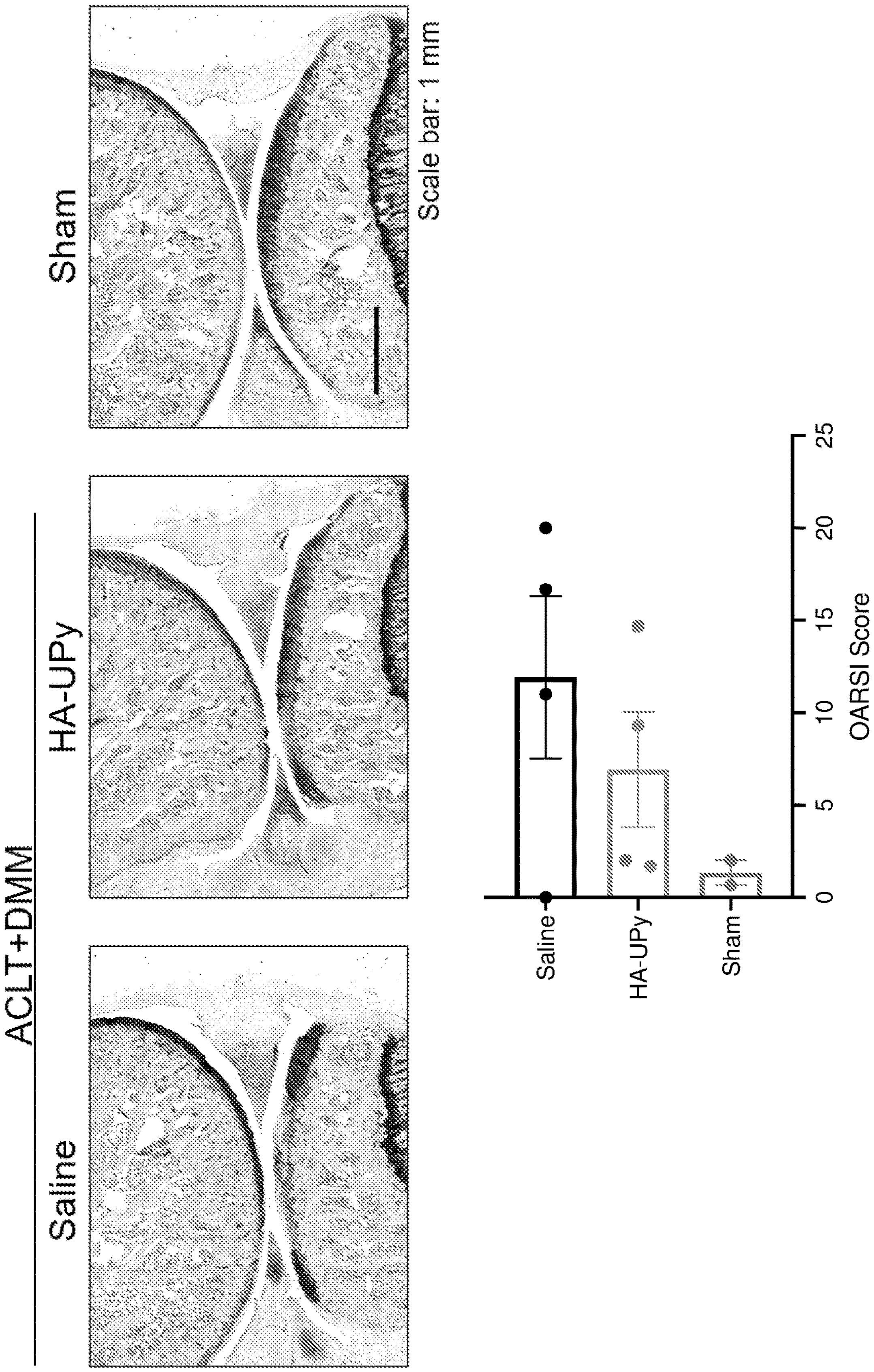
FIG. 26 shows images from a joint injury model (anterior cruciate ligament transection with destabilization of the medial meniscus (ACLT+DMM)) model in rat, demonstrating that the 1M Da HA-UPY reduced cartilage degeneration.
Figure 27:
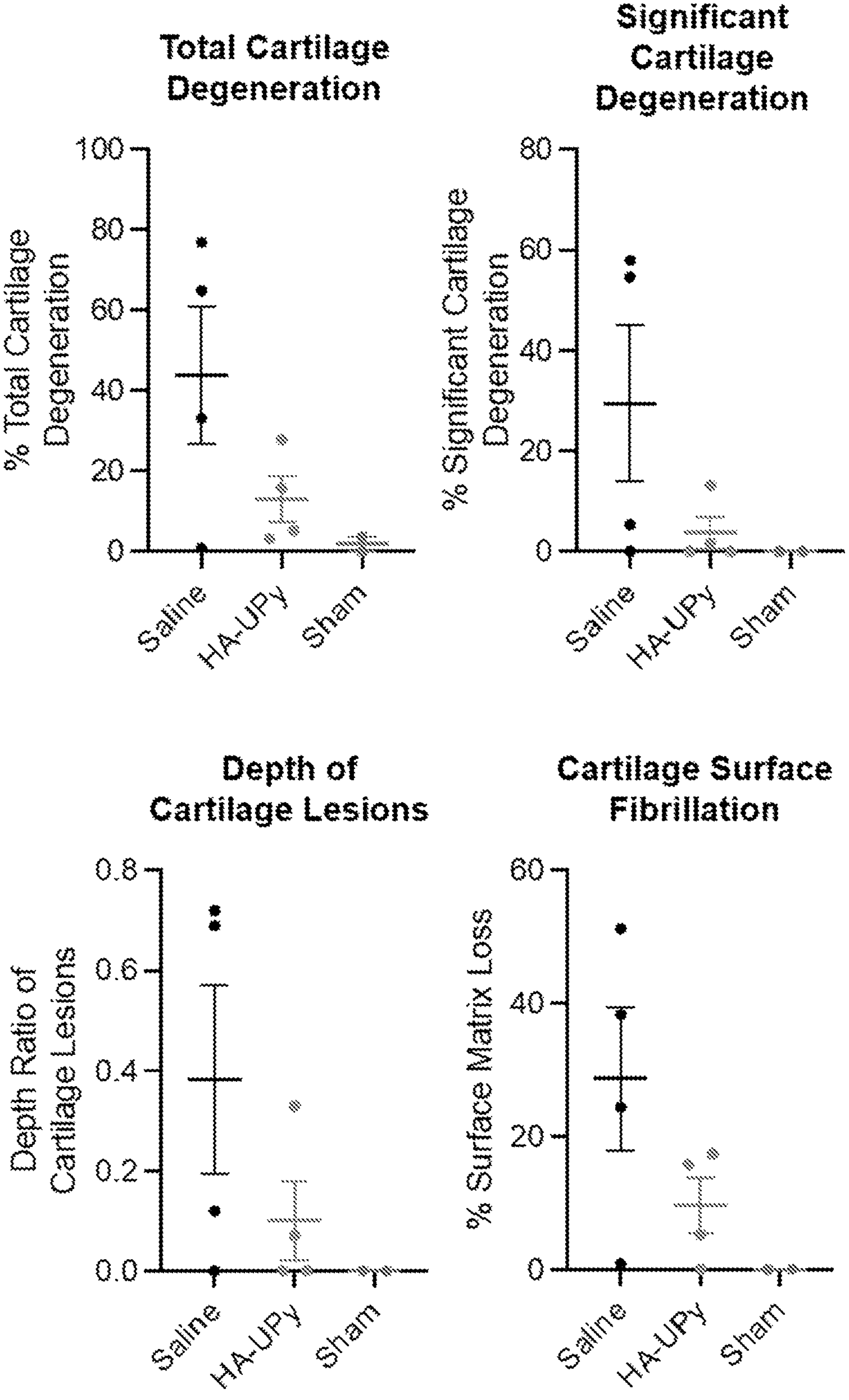
FIG. 27 shows data from quantitative measures of total cartilage degeneration, significant cartilage degeneration, depth of cartilage lesions, and cartilage surface fibrillation, and thickness of cartilage lesions for the tibia, following treatment with 1M Da HA-UPy or controls.
Figure 28:
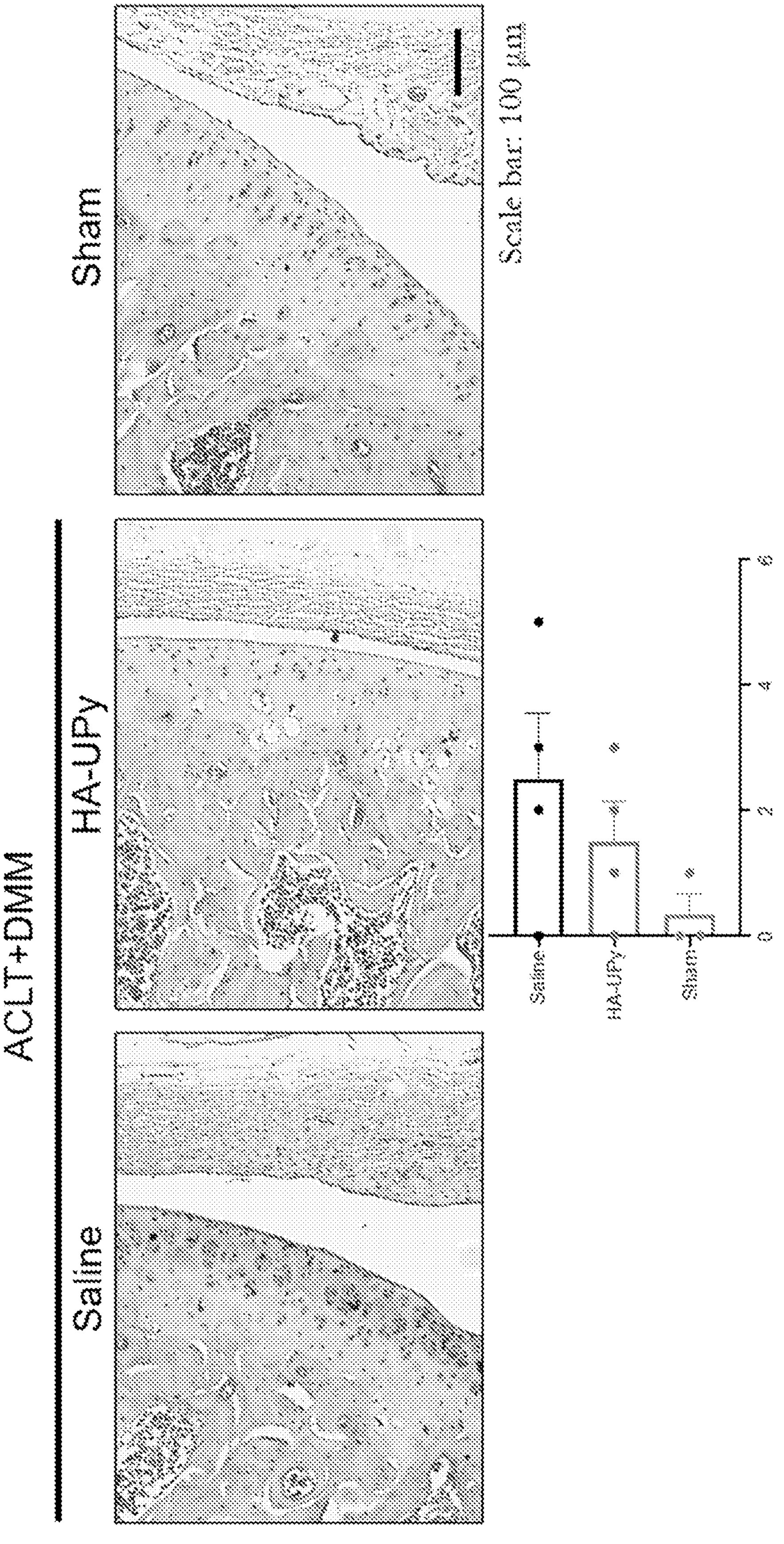
FIG. 28 shows data from the ACLT+DMM model in rat, demonstrating that the 1M Da HA-UPy group exhibited less severe synovitis. This indicates less joint inflammation with the HA-UPy treatment.

To examine the lubrication and chondroprotective function of the modified HA, a joint injury model (anterior cruciate ligament transection with destabilization of the medial meniscus (ACLT+DMM)) model was used in rat. The animals were treated with intra-articular injection of the 1 MDa HA-UPy, or saline. The frequency of injection was once a month. A sham surgery control was also used for these studies; this involved opening up the knee, but no injury was made to the ACL or the meniscus. These studies show that intra-articular injection of HA-UPy mitigated pain (FIG. 25) and maintained cartilage health (FIGS. 26-28). In particular, FIG. 25 shows 50% paw withdrawal threshold (PWT) measurements, which represents the force at which the rat will respond to (i.e., withdraw its paw in response to) 50% of the time (the Von Frey test). A greater paw withdrawal threshold corresponds to less sensitivity of the injured limb in response to a normally innocuous stimulus (less mechanical allodynia). The HA-UPy group showed greater PWT in this test. The data in FIGS. 26, 27, and 28 show that HA-UPy reduced cartilage degeneration following ACLT+DMM, that HA-UPy reduced ameliorated severe cartilage lesion formation in the tibia, and that the HA-UPy group exhibited less severe synovitis, respectively. For the synovitis score in FIG. 28, scoring was performed as described in Lewis et al. *Osteoarth. Cartilage* 2011, 19, 864, and in Ierna et al. *BMC Musculoskel. Dis.* 2010, 11:136.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The invention claimed is:

1. A method of promoting and/or improving chondroprotection in a joint of a subject, the method comprising administering to the joint a therapeutically effective amount of a functionalized hyaluronic acid compound comprising repeat units of formula (I):

(I)

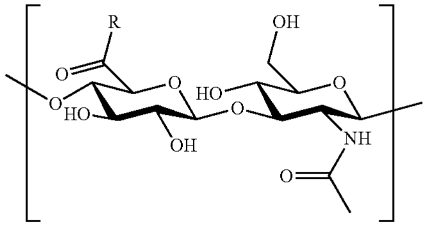

wherein each R is independently selected from —OH, —$O^-M^+$, and a moiety of formula (II):

(II)

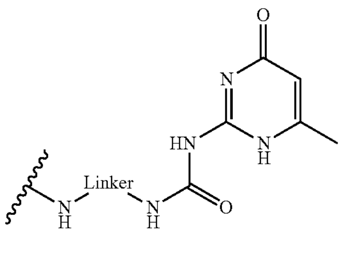

, wherein each M is independently a monovalent cation, and wherein at least one R is a moiety of formula (II).

2. The method of claim 1, wherein the joint is a knee joint.

3. The method of claim 1, wherein the linker comprises one or more methylene (—$CH_2$—), ether (—O—), amine (—NH—), thioether (—S—), or carbonyl (—C(O)—) moieties, or any combination thereof.

4. The method of claim 1, wherein the linker comprises a combination of urea (—NH—C(O)—NH—) and $C_1$-$C_8$ alkylene moieties.

5. The method of claim 1, wherein the linker has formula:

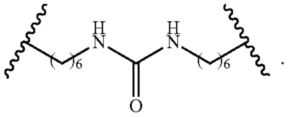

6. The method of claim 1, wherein about 10% to about 30% of the R groups are a moiety of formula (II).

7. The method of claim 6, wherein about 15% to about 25% of the R groups are a moiety of formula (II).

8. The method of claim 1, wherein the hyaluronic acid backbone has a molecular weight of about 40 kDa to about 2000 kDa.

9. The method of claim 8, wherein the hyaluronic acid backbone has a molecular weight of about 100 kDa to about 1000 kDa.

* * * * *